US008290596B2

(12) United States Patent
Wei et al.

(10) Patent No.: US 8,290,596 B2
(45) Date of Patent: Oct. 16, 2012

(54) THERAPY PROGRAM SELECTION BASED ON PATIENT STATE

(75) Inventors: Xuan Wei, Plymouth, MN (US); Richard T. Stone, Minneapolis, MN (US); Timothy J. Denison, Minneapolis, MN (US); Gregory F. Molnar, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 461 days.

(21) Appl. No.: 12/238,025

(22) Filed: Sep. 25, 2008

(65) Prior Publication Data

US 2009/0105785 A1    Apr. 23, 2009

Related U.S. Application Data

(60) Provisional application No. 61/023,522, filed on Jan. 25, 2008, provisional application No. 61/049,166, filed on Apr. 30, 2008, provisional application No. 60/975,372, filed on Sep. 26, 2007, provisional application No. 61/025,503, filed on Feb. 1, 2008, provisional application No. 61/083,381, filed on Jul. 24, 2008.

(51) Int. Cl.
    *A61N 1/36*    (2006.01)
(52) U.S. Cl. ......................................................... 607/45
(58) Field of Classification Search ................... 607/45; 600/378
    See application file for complete search history.

(56) References Cited

U.S. PATENT DOCUMENTS

| 3,780,725 | A |  | 12/1973 | Goldberg |
| 4,013,068 | A |  | 3/1977 | Settle et al. |
| 4,138,649 | A |  | 2/1979 | Schaffer |
| 4,279,258 | A |  | 7/1981 | John |
| 4,579,125 | A |  | 4/1986 | Strobl et al. |
| 4,610,259 | A |  | 9/1986 | Cohen et al. |
| 5,205,285 | A | * | 4/1993 | Baker, Jr. ........................ 607/45 |
| 5,458,117 | A |  | 10/1995 | Chamoun et al. |
| 5,619,536 | A |  | 4/1997 | Gourgue |
| 5,725,558 | A |  | 3/1998 | Warnke |
| 5,840,040 | A |  | 11/1998 | Altschuler et al. |
| 6,011,990 | A |  | 1/2000 | Schultz et al. |
| 6,024,700 | A |  | 2/2000 | Nemirovski et al. |
| 6,066,163 | A |  | 5/2000 | John |

(Continued)

FOREIGN PATENT DOCUMENTS

CN            10199670 A        1/2008

(Continued)

OTHER PUBLICATIONS

Office Action for U.S. Appl. No. 11/974,931, mailed Sep. 16, 2010, 11 pages.

(Continued)

*Primary Examiner* — Carl H Layno
*Assistant Examiner* — Paula J Stice
(74) *Attorney, Agent, or Firm* — Shumaker & Sieffert, PA

(57) ABSTRACT

A therapy program is selected based on a patient state, where the patient state comprises at least one of a movement state, sleep state or speech state. In this way, therapy delivery is tailored to the patient state, which may include specific patient symptoms. The therapy program is selected from a plurality of stored therapy programs that comprise therapy programs associated with a respective one at least two of the movement, sleep, and speech states. Techniques for determining a patient state include receiving volitional patient input or detecting biosignals generated within the patient's brain. The biosignals are nonsymptomatic and may be incidental to the movement, sleep, and speech states or generated in response to volitional patient input.

29 Claims, 16 Drawing Sheets

U.S. PATENT DOCUMENTS

| | | | |
|---|---|---|---|
| 6,129,681 | A | 10/2000 | Kuroda et al. |
| 6,331,160 | B1 | 12/2001 | Bardy |
| 6,463,328 | B1 | 10/2002 | John |
| 6,876,842 | B2 | 4/2005 | Davie |
| 6,993,380 | B1 | 1/2006 | Modarres |
| 7,110,820 | B2 * | 9/2006 | Tcheng et al. ............ 607/45 |
| 7,120,486 | B2 | 10/2006 | Leuthardt et al. |
| 7,299,088 | B1 | 11/2007 | Thakor et al. |
| 7,684,867 | B2 * | 3/2010 | Jaax et al. ............ 607/45 |
| 2002/0002390 | A1 | 1/2002 | Fischell et al. |
| 2002/0177882 | A1 | 11/2002 | DiLorenzo |
| 2003/0046254 | A1 | 3/2003 | Ryu et al. |
| 2004/0077967 | A1 | 4/2004 | Jordan |
| 2004/0249422 | A1 * | 12/2004 | Gliner et al. ............ 607/58 |
| 2005/0007091 | A1 | 1/2005 | Makeig et al. |
| 2005/0081847 | A1 | 4/2005 | Lee et al. |
| 2005/0240242 | A1 | 10/2005 | DiLorenzo |
| 2006/0041221 | A1 | 2/2006 | Stypulkowski |
| 2006/0133550 | A1 | 6/2006 | Bolton et al. |
| 2006/0135879 | A1 | 6/2006 | Liley |
| 2006/0149338 | A1 | 7/2006 | Flaherty et al. |
| 2006/0169282 | A1 | 8/2006 | Izumi et al. |
| 2006/0212093 | A1 * | 9/2006 | Pless et al. ............ 607/45 |
| 2006/0293604 | A1 | 12/2006 | Carlson et al. |
| 2007/0010755 | A1 | 1/2007 | Sarkela et al. |
| 2007/0016095 | A1 | 1/2007 | Low et al. |
| 2007/0032737 | A1 | 2/2007 | Causevic et al. |
| 2007/0032834 | A1 | 2/2007 | Gliner et al. |
| 2007/0150025 | A1 | 6/2007 | Dilorenzo et al. |
| 2008/0071314 | A1 * | 3/2008 | John ............ 607/2 |
| 2008/0077191 | A1 | 3/2008 | Morrell |
| 2008/0243005 | A1 | 10/2008 | Jung et al. |
| 2009/0118786 | A1 | 5/2009 | Meadows et al. |
| 2009/0118787 | A1 | 5/2009 | Moffitt et al. |
| 2009/0131995 | A1 | 5/2009 | Sloan et al. |

FOREIGN PATENT DOCUMENTS

| | | |
|---|---|---|
| DE | 19649991 A1 | 6/1998 |
| EP | 0438945 A1 | 7/1991 |
| EP | 1943944 A1 | 7/2008 |
| GB | 2447640 A | 9/2008 |
| JP | 2008154681 | 7/2008 |
| KR | 20010096372 | 11/2001 |
| RU | 2144310 C1 | 1/2000 |
| WO | WO 97/10747 | 3/1997 |
| WO | WO 2005/089646 A1 | 9/2005 |
| WO | WO 2006/121455 A1 | 11/2006 |
| WO | WO 2006/126186 A2 | 11/2006 |
| WO | WO 2007/112092 A2 | 10/2007 |
| WO | WO 2009/059041 A1 | 5/2009 |

OTHER PUBLICATIONS

Responsive Amendment to Office Action for U.S. Appl. No. 11/974,931, filed Dec. 16, 2010, 15 pages.

Notification of Transmittal of the International Preliminary Report on Patentability for patent application No. PCT/US2008/011107, mailed Dec. 18, 2009, 14 pages.

Avestruz et al., "A 5 µW/Channel Spectral Analysis IC for Chronic Bidirectional Brain-Machine Interfaces," IEEE Journal of Solid-State Circuits, vol. 43, No. 12, Dec. 2008, 19 pages.

Foffani et al., "Analysis of local field potentials from the human subthalamic nucleus," Proceedings of the $25^{th}$ Annual International Conference of the IEEE EMBS, Sep. 17-21, 2003, 3 pages.

Office action for U.S. Appl. No. 11/974,931, mailed Apr. 4, 2011, 10 pages.

Office action for U.S. Appl. No. 12/237,799, mailed Apr. 14, 2011, 12 pages.

Office Action from U.S. Appl. No. 12/431,167, dated Aug. 18, 2011, 16 pages.

Response to Office Action dated Aug. 18, 2011, from U.S. Appl. No. 12/431,167, filed Nov. 17, 2011, 15 pages.

Masui, "A 0.6 V Supply CMOS Amplifier Using Noise Reduction Technique of Autozeroing and Chopper Stabilization," 21st Century COE Program, Hiroshima University, Proceedings of the Fifth Hiroshima International Workshop, 2007, 5 pages.

Abidi, "CMOS wireless transceivers: the new wave," IEEE Communications Magazine 37, 119-124 (1999).

Rauscher, "Practical Realization of an Analyzer Operating on the Heterodyne Principle," Chapter 4 (partial) of Fundamentals of Spectrum Analysis (Rohde & Schwarz, 2001 ). pp. 34-64. With 2 pages of front matter and 2 pages of diagrams.

Yates, "An ultra low power low noise chopper amplifier for wireless EEG". In 49th IEEE International Midwest Symposium on Circuits and Systems, 2006. MWSCAS '06., vol. 2, 449-452 (IEEE, 2006).

Jianping et al.,"Study on Feature Extraction of the Sleep-Multigraph", Journal of Biomedical Engineering, Issue 5, vol. 22, p. 906-909, Dec. 31, 2005, translation of abstract and substantial portions mentioned in the First Office Action dated Aug. 17, 2011, from SIPO for Chinese application No. 200880125611.1 (the Chinese counterpart of copending U.S. Appl. No. 12/238,105).

Jianping et al.,"Study on Feature Extraction of the Sleep-Multigraph", Journal of Biomedical Engineering, Issue 5, vol. 22, p. 906-909, Dec. 31, 2005, English translation of abstract only.

Office Action from Chinese application No. 200880125611.1 (the Chinese counterpart of copending U.S. Appl. No. 12/238,105), dated Aug. 17, 2011, 10 pages.

Office Action from U.S. Appl. No. 12/431,167, dated Jan. 31, 2012, 20 pages.

Response to Office Action dated Jan. 31, 2012, from U.S. Appl. No. 12/431,167, filed Mar. 30, 2012, 17 pages.

* cited by examiner

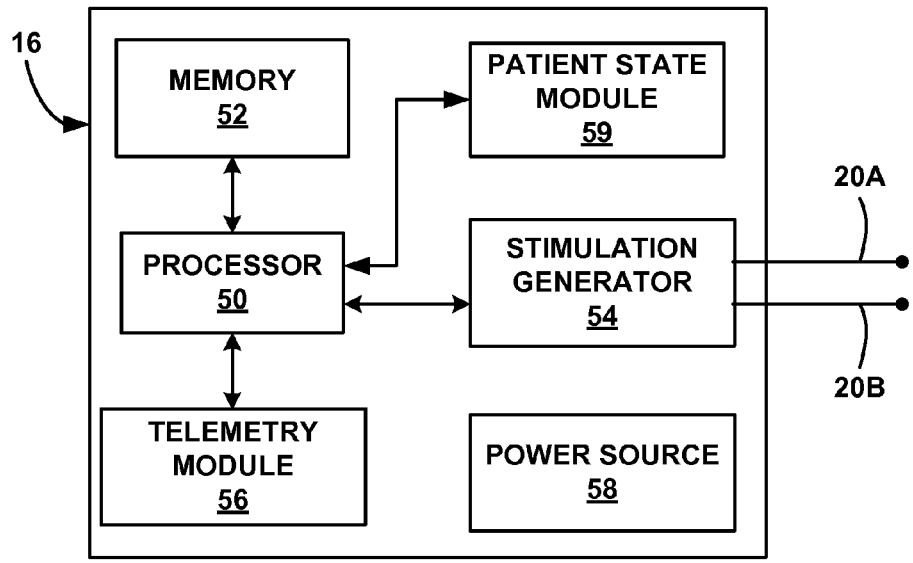
FIG. 3
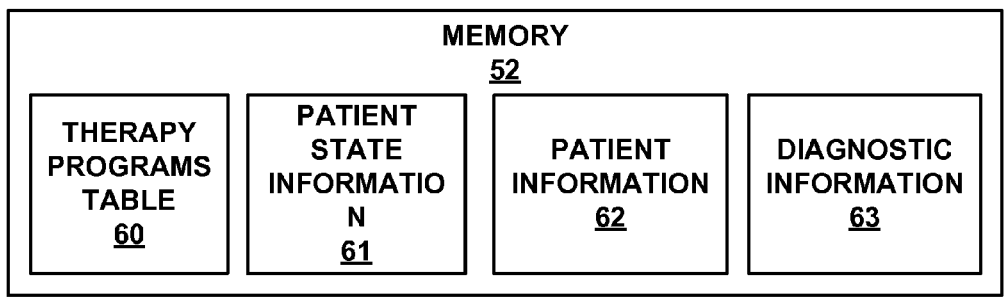
FIG. 4
| Program Table Record | Patient State | Amplitude (V) | Pulse Width (μs) | Frequency (Hz) | Electrode Configuration |
|---|---|---|---|---|---|
| 1 | MOVEMENT | 2.0 | 150 | 130 | 3+ 3- |
| 2 | MOVEMENT | 2.5 | 200 | 150 | 5+ 5- |
| 3 | SLEEP | 1.0 | 100 | 40 | 3- 2+ |
| 4 | SPEECH | 6.6 | 100 | 10 | 1- 3+ |
FIG. 5

THERAPY PROGRAM SELECTION BASED ON PATIENT STATE

This application claims the benefit of U.S. Provisional Application No. 61/023,522 to Stone et al., entitled, "THERAPY PROGRAM SELECTION" and filed on Jan. 25, 2008, U.S. Provisional Application No. 61/049,166 to Wu et al., entitled, "SLEEP STAGE DETECTION" and filed on Apr. 30, 2008, U.S. Application No. 60/975,372 to Denison et al., entitled "FREQUENCY SELECTIVE MONITORING OF PHYSIOLOGICAL SIGNALS" and filed on Sep. 26, 2007, U.S. Provisional Application No. 61/025,503 to Denison et al., entitled "FREQUENCY SELECTIVE MONITORING OF PHYSIOLOGICAL SIGNALS" and filed on Feb. 1, 2008, and U.S. Provisional Application No. 61/083,381 to Denison et al., entitled, "FREQUENCY SELECTIVE EEG SENSING CIRCUITRY" and filed on Jul. 24, 2008. The entire contents of above-identified U.S. Provisional Application Nos. 61/023,522, 61/049,166, 60/975,372, 61/025,503, and 61/083,381 are incorporated herein by reference.

TECHNICAL FIELD

The disclosure relates to medical therapy systems, and, more particularly, control of medical therapy systems.

BACKGROUND

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) to one or more sites within a patient, such as a brain, spinal cord, leg muscle or arm muscle, may help alleviate, and in some cases, eliminate symptoms associated with movement disorders. Similarly, delivery of electrical stimulation and/or a fluid to one or more sites within a patient may help alleviate other patient conditions, such as impairment of speech (e.g., verbal fluency).

SUMMARY

In general, the disclosure is directed to methods and systems for managing multiple symptoms of a patient's condition. A therapy program selection technique includes selecting a therapy program based on whether a patient is in a movement, sleep or speech state ("patient states"). Selecting a therapy program comprises at least one of choosing a stored therapy program or modifying a stored therapy program. A movement state may include a state in which the patient is intending on moving, is attempting to initiate movement or has initiated movement. A sleep state may include a state in which the patient is intending on sleeping, is attempting to sleep or has initiated sleep. A speech state may include a state in which the patient is intending on speaking, is attempting to speak or has initiated speech.

Many patient conditions, such as Parkinson's disease or other neurological disorders, include impaired movement, sleep, and speech states, or combinations of impairment at least two of the movement, sleep, and speech states. Different therapy parameter values may provide efficacious therapy for the patient's movement, sleep and speech states. For example, in some examples, deep brain stimulation may be delivered to the patient at a relatively high frequency when a movement state is detected compared to when the speech state is detected. In addition, within each of the movement, sleep, and speech states, different therapy parameter values may provide efficacious therapy for the particular patient condition associated with the movement, sleep or speech states. For example, in some examples, a first therapy program (including a set of therapy parameter values, such as an electrode combination and/or the frequency, amplitude, and pulse width of electrical stimulation) may be selected if a first symptom of the movement state is detected (e.g., akinesia) and a second therapy program may be selected if a second symptom of the movement state is detected (e.g., gait freeze).

The therapy systems and methods described herein provide relevant therapy for the different patient states by determining a patient state and selecting a stored therapy program, or adjusting therapy program parameter values, based on the determined patient state. Hence, therapy is tailored to the patient's current state. The current state may be the state of the patient at approximately the same time at which the state is detected and, in some cases, approximately the same time at which a therapy program is selected. In some examples, the current patient state may also be a near-term anticipated patient state, e.g., upcoming patient states. The therapy systems described herein store a plurality of therapy programs for at least two of the movement, sleep or speech states and associate the therapy programs with the respective patient state.

A patient's current state may be determined via various techniques. In some examples, the patient state may be determined based on volitional patient input received by a programmer, a sensing device incorporated into the medical device or separate from the therapy delivery device or by biosignals generated within the patient's brain. In other examples, the patient state may also be determined based on biosignals generated within the patient's brain that are incidental to the patient's movement, sleep, and speech states. In addition or alternatively, the patient state may be determined based on patient activity or posture that is incidental to the patient's movement, sleep, and speech states.

In one aspect, the disclosure is directed to a method comprising determining a patient state, wherein the patient state comprises at least one of a movement state, sleep state or speech state, and selecting a therapy program from a plurality of stored therapy programs based on the determined patient state. The plurality of stored programs comprises therapy programs associated with a respective one of at least two of the movement, sleep, and speech states. For example, the plurality of stored programs may comprise therapy programs associated with a respective one of the movement and sleep states, a respective one of the movement and speech states, a respective one of the sleep and speech states, or a respective one of the movement, sleep, and speech states.

In another aspect, the disclosure is directed to a system comprising a memory that stores a plurality of therapy programs or instructions for modifying a baseline therapy program, and associates each therapy program or instruction with a patient state, the patient state comprising at least one of a movement state, sleep state or a speech state, wherein the memory stores therapy programs associated with at least two of the movement, sleep, and speech states, and a processor that determines a patient state and selects a therapy program from the memory based on the determined patient state.

In another aspect, the disclosure is directed to a computer-readable medium comprising instructions. The instructions cause a programmable processor to determine a patient state, wherein the patient state comprises at least one of a movement state, sleep state or speech state, and select a therapy program from a memory storing a plurality of stored therapy programs based on the determined patient state. Each of the therapy programs are associated with a respective one at least two of the movement, sleep, and speech states.

In another aspect, the disclosure is directed to a system comprising means for determining a patient state, wherein the patient state comprises at least one of a movement state, sleep state or speech states, and means for selecting a therapy program from a plurality of stored therapy programs based on the determined patient state. The plurality of stored programs comprises therapy programs associated with a respective one of at least two of the movement, sleep, and speech states.

In another aspect, the disclosure is directed to a method comprising determining whether a patient is in a movement state, determining whether the patient is a speech state, and selecting a first therapy program if the patient is in the movement state and selecting a second therapy program different than the first therapy program if the patient is in the speech state. The first therapy program and second therapy program are different. For example, the first and second therapy programs may comprise at least one different therapy parameter value.

In another aspect, the disclosure is directed to a computer-readable medium comprising instructions. The instructions cause a programmable processor to perform any of the techniques described herein.

The details of one or more examples are set forth in the accompanying drawings and the description below. Other features, objects, and advantages of the systems, devices, and techniques of the disclosure will be apparent from the description and drawings, and from the claims.

BRIEF DESCRIPTION OF DRAWINGS

FIG. 3 is functional block diagram illustrating components of an example electrical stimulator.

FIG. 4 is a block diagram illustrating an example configuration of a memory of the medical device of FIG. 1.

FIG. 5 illustrates an example therapy programs table stored within the memory of FIG. 4.

DETAILED DESCRIPTION

Figure 1:
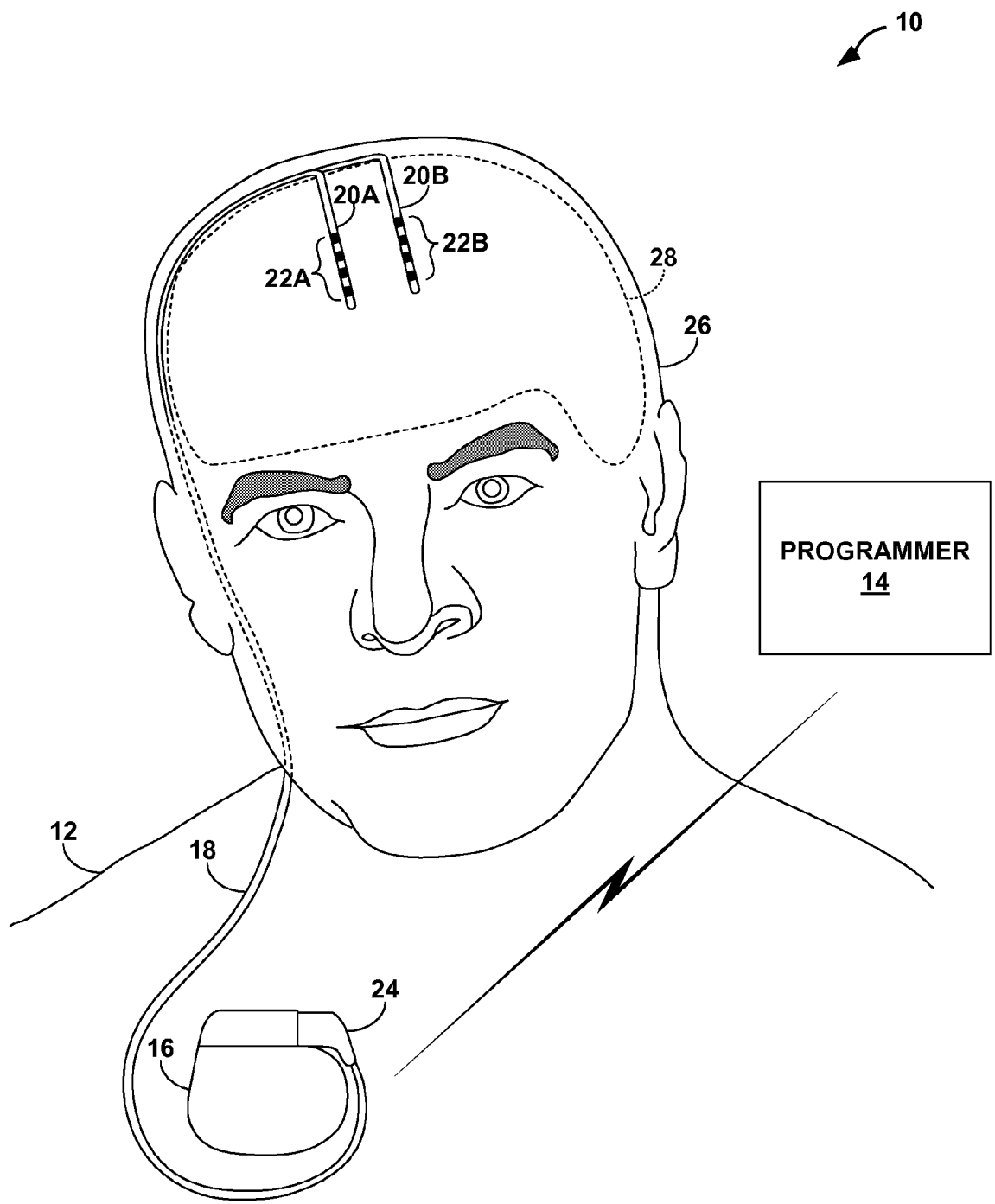
FIG. 1 is a conceptual diagram illustrating an example deep brain stimulation (DBS) system that manages multiple symptoms of a patient condition.

FIG. 1 is a conceptual diagram illustrating an example deep brain stimulation (DBS) system 10 that manages multiple symptoms of a condition of patient 12. Patient 12 ordinarily will be a human patient. In some cases, however, DBS system 10 may be applied to other mammalian or non-mammalian non-human patients. Some patient conditions, such as Parkinson's disease and other neurological conditions, result in impaired movement, speech, and sleep states or at least two of the impaired movement, speech or sleep states. DBS system 10 is useful for managing such patient conditions. In particular, DBS system 10 stores a plurality of therapy programs, and where at least one of stored therapy program is associated with a respective one of the movement, sleep, and speech states. In the example shown in FIG. 1, DBS system 10 includes a processor that determines whether patient 12 is in a movement state, sleep state or speech state, and selects stored therapy parameter values (e.g., a therapy program defining a set of therapy parameter values) based on the determined state of patient 12. In this way, therapy delivery to patient 12 may be dynamically changed based on a detected patient state.

Different therapy parameter values may provide efficacious therapy for the movement, sleep, and speech states. Accordingly, DBS system 10 is useful for managing a patient condition that results in impaired movement, sleep, and speech states or at least two of the impaired movement, sleep or speech states. For example, in some cases, therapy programs that relieve movement symptoms may deteriorate verbal fluency. DBS system 10 may help alleviate deterioration in verbal fluency that may result from therapy delivered to manage the movement state.

Rather than delivering therapy according to one or more therapy programs regardless of the patient's current state, DBS system 10 selectively delivers a therapy program that addresses a detected state of patient 12. DBS system 10 may "select" a therapy program based on a determined patient state by choosing and loading a stored therapy program to control therapy delivery or by modifying at least one therapy parameter value of a stored therapy program (or therapy program group including more than one therapy program) based on instructions that are associated with the determined patient state. In this way, DBS system 10 is configured to adapt therapy parameter values to a current patient state and deliver responsive therapy to the patient's current state. The current state may be the state of patient 12 at approximately the same time at which the state is detected and, in some cases, approximately the same time at which a therapy program is selected. In addition, in some examples, the current patient state may also be a near-term anticipated patient state, e.g., upcoming patient states.

A movement state may include a state in which patient 12 is intending to move (e.g., initiating thoughts relating to moving a body part, e.g., a limb or a leg to initiate movement), is attempting to initiate movement or has successfully initiated movement and is currently moving. In some cases when patient 12 is attempting to initiate movement, patient 12 may be unable to initiate movement or may initiate movement, but failed to move properly. For example, patient 12 may subtly move his arm toward a target due to an intent to move toward the target, but may fail in maintaining the movement toward the target.

If patient 12 is afflicted with a movement disorder or other neurodegenerative impairment, therapy delivery, such as delivery of electrical stimulation therapy (FIG. 1), a fluid delivery therapy (e.g., delivery of a pharmaceutical agent), fluid suspension delivery, or delivery of an external cue (FIG. 2) may improve the performance of motor tasks by patient 12 that may otherwise be difficult. These tasks may include, for example, at least one of initiating movement, maintaining movement, grasping and moving objects, improving gait associated with narrow turns, handwriting, and so forth. Symptoms of movement disorders include, for example, limited muscle control, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions. Accordingly, by determining when patient 12 is in a movement state, DBS system 10 may provide "on demand" therapy to help manage symptoms of the patient's movement disorder.

A sleep state may include a state in which patient 12 is intending on sleeping (e.g., initiating thoughts of sleep), is attempting to sleep or has initiated sleep and is currently sleeping. Within a sleep state, patient 12 may be within one of a plurality of sleep stages. Example sleep stages include, for example, Stage 1 (also referred to as Stage N1 or S1), Stage 2 (also referred to as Stage N2), Deep Sleep (also referred to as slow wave sleep), and rapid eye movement (REM). The Deep Sleep stage may include multiple sleep stages, such as Stage N3 (also referred to as Stage S3) and Stage N4 (also referred to as Stage S4). In some cases, patient 12 may cycle through the Stage 1, Stage 2, Deep Sleep, REM sleep stages more than once during a sleep state. The Stage 1, Stage 2, and Deep Sleep stages may be considered non-REM (NREM) sleep stages.

During the Stage 1 sleep stage, patient 12 may be in the beginning stages of sleep, and may begin to lose conscious awareness of the external environment. During the Stage 2 and Deep Sleep stages, muscular activity of patient 12 may decrease, and conscious awareness of the external environment may disappear. During the REM sleep stage, patient 12 may exhibit relatively increased heart rate and respiration compared to Sleep Stages 1 and 2 and the Deep Sleep stage. In some cases, the Stage 1, Stage 2, and deep sleep stages may each last about five minutes to about fifteen minutes, although the actual time ranges may vary between patients. In some cases, REM sleep may begin about ninety minutes after the onset of sleep, and may have a duration of about five minutes to about fifteen minutes or more, although the actual time ranges may vary between patients.

When patient 12 attempts to sleep, patient 12 may successfully initiate sleep, but may not be able to maintain a certain sleep stage (e.g., a nonrapid eye movement (NREM) sleep state). As another example, when patient 12 attempts to sleep, patient 12 may not be able to initiate sleep or may not be able to initiate a certain sleep state. In some cases, a patient condition, such as Parkinson's disease, may affect the quality of a patient's sleep. For example, neurological disorders may cause patient 12 to have difficulty falling asleep and/or may disturb the patient's sleep, e.g., cause patient 12 to wake periodically. Further, neurological disorders may cause the patient to have difficulty achieving deeper sleep stages, such as one or more of the NREM sleep stages.

Some patients that are also afflicted with a movement disorder suffer from sleep disturbances, such as daytime somnolence, insomnia, disturbances in rapid eye movement (REM) sleep. Epilepsy is an example of a neurological disorder that may affect sleep quality. Other neurological disorders that may negatively affect patient sleep quality include movement disorders, such as tremor, Parkinson's disease, multiple sclerosis, or spasticity. The uncontrolled movements associated with such movement disorders may cause a patient to have difficulty falling asleep, disturb the patient's sleep, or cause the patient to have difficulty achieving deeper sleep stages. Further, in some cases, poor sleep quality may increase the frequency or intensity of symptoms experienced by patient 12 due to a neurological disorder. For example, poor sleep quality may be linked to increased movement disorder symptoms in movement disorder patients.

Therapy delivery to patient 12 during a sleep state may help alleviate at least some sleep disturbances. For example, in some examples, DBS system 10 may deliver stimulation to certain regions of brain 28 of patient 12, such as the locus coeruleus, dorsal raphe nucleus, posterior hypothalamus, reticularis pontis oralis nucleus, nucleus reticularis pontis caudalis, or the basal forebrain, during a sleep state in order to help patient 12 fall asleep, maintain the sleep state or maintain deeper sleep stages (e.g., REM sleep). In addition to or instead of electrical stimulation therapy, a suitable pharmaceutical agent, such as acetylcholine, dopamine, epinephrine, norepinephrine, serotonine, inhibitors of noradrenaline or any agent for affecting a sleep disorder or combinations thereof may be delivered to brain 28 of patient 12. By alleviating the patient's sleep disturbances, patient 12 may feel more rested, and, as a result, DBS system 10 may help improve the quality of patient's life.

Patients with Parkinson's disease or other movement disorders associated with a difficulty moving (e.g., akinesia, bradykinesia or rigidity) may have a poor quality of sleep during the Stage 1 sleep stage, when patient 12 is attempting to fall asleep. For example, an inability to move during the Stage 1 sleep stage may be discomforting to patient 12, which may affect the ability to fall asleep. Accordingly, during a sleep stage associated with the Stage 1 sleep stage, a processor of IMD 16 or programmer 14 may select a therapy program that helps improve the motor skills of patient 12, such that patient 12 may initiate movement or maintain movement, e.g., to adjust a sleeping position.

In some patients with movement disorders, the patient may become more physically active during the REM sleep stage. For example, patient 12 may involuntarily move his legs during the REM sleep stage or have other periodic limb movements. The physical activity of patient 12 may be disruptive to the patient's sleep, as well as to others around patient 12 when patient 12 is in the REM sleep stage. Accordingly, IMD 16 may deliver stimulation therapy to patient 12 during the sleep state to help minimize the patient's movement.

A speech state may include a state in which patient 12 is intending on speaking, is attempting to speak or has initiated speech. In the speech state, patient 12 may generate volitional thoughts related to initiating speech. Similarly, in the speech state, patient 12 may successfully initiate speech, but may not be able to maintain the verbal fluency, e.g., may unintentionally stop speaking or may have difficulty speaking. As another example, in the speech state, patient 12 may attempt to initiate speech without success. Some patients that are also afflicted with a movement disorder suffer from speech disorder, such as impaired laryngeal function or articulatory dysfunction. For example, patients with Parkinson's disease may be afflicted with hypokinetic dysarthria, which is a general difficulty speaking. Hypokinetic dysarthria may be caused by dysfunction in the pallidal-cortical and/or thalamocortical circuitries, which may result in rigidity and dyskinesia in the respiratory, phonatory, and/or articulatory musculature. Therapy delivery to patient 12 during a speech state may help alleviate at least some symptoms of a speech disorder. For example, in some examples, DBS system 10 may deliver stimulation to certain regions of brain 28, such as bilateral stimulation of the subthalamic nucleus or globus pallidus. In addition to or instead of electrical stimulation therapy, a suitable pharmaceutical agent may be delivered to brain 28 of patient 12 or other tissue sites within patient 12 to help manage speech impairment.

DBS system 10 includes medical device programmer 14, implantable medical device (IMD) 16, lead extension 18, and leads 20A and 20B with respective electrodes 22A, 22B. IMD 16 includes a therapy module that delivers electrical stimulation therapy to patient 12 via electrodes 22A, 22B of leads 20A and 20B, respectively, as well as a processor that selects therapy parameter values based on whether the patient's movement state, sleep state or speech state is detected. In some examples, as described in further detail below, a processor of IMD 16 may determine the state of patient 12 based on biosignals, such as bioelectrical brain signals, detected within brain 28 of patient 12 via electrodes 22A, 22B of leads 20A and 20B, respectively, or a separate electrode array. Examples of bioelectrical signals include an electroencephalogram (EEG) signal, an electrocorticogram (ECoG) signal, a signal generated from measured field potentials within one or more regions of brain 28 or action potentials from single cells within brain 28 (referred to as "spikes" or single cell recordings). Determining action potentials of single cells within brain 28 may require resolution of bioelectrical signals to the cellular level and provides fidelity for fine movements, i.e., a bioelectrical signal indicative of fine movements (e.g., slight movement of a finger).

In other examples, patient 12 may provide volitional input to indicate the movement, sleep or speech states. Different inputs may be provided to indicate the different states. In some examples, patient 12 may provide a volitional input via an accelerometer (e.g., tapping the accelerometer in a particular pattern) or voice detector. The accelerometer may be, for example, disposed within IMD 16 or another implanted or external device. In other examples, patient 12 may provide the volitional input via programmer 14, which may include dedicated buttons by which the patient may selectively indicate each of the movement, sleep, and speech states. In other examples, DBS system 10 may detect volitional patient input via biosignals that are unrelated to the patient's symptoms, as described in further detail below.

While the description of DBS system 10 is primarily directed to examples in which IMD 16 determines a state of patient 12 and selects a therapy program based on the determined patient state, in other examples, a device separate from IMD 16, such as programmer 14, a sensing device or another computing device, may determine the state of patient 12 and provide the indication to IMD 16. Furthermore, although IMD 16 may select a therapy program or parameter values based on the determined patient state, in other examples, another device may select a therapy program or parameter values based on the determined patient state, whether the patient state is determined by IMD 16 or a separate device, and input the therapy parameter values of the program to IMD 16. A therapy program may include a set of therapy parameter values, which may include, for example, an electrode combination for delivering stimulation to patient 12, the therapy delivery site within patient 12, and stimulation parameter values (e.g., respective values for a stimulation signal frequency, pulse width, and/or amplitude of stimulation).

IMD 16 may be implanted within a subcutaneous pocket above the clavicle, or, alternatively, the abdomen or back of patient 12. Implanted lead extension 18 is coupled to IMD 16 via connector 24. In the example of FIG. 1, lead extension 18 traverses from the implant site of IMD 16 and along the neck of patient 12 to cranium 26 of patient 12 to access brain 28. Leads 20A and 20B (collectively "leads 20") are implanted within the right and left hemispheres, respectively, of patient 12 in order deliver electrical stimulation to one or more regions of brain 28, which may be selected based on the patient condition or disorder controlled by DBS system 10. Other lead 20 implant sites are contemplated. External programmer 14 wireless communicates with IMD 16 as needed to provide or retrieve therapy information.

Although leads 20 are shown in FIG. 1 as being coupled to a common lead extension 18, in other examples, leads 20 may be coupled to IMD 16 via separate lead extensions or directly to connector 24 of IMD 16. Connector 24 may include electrical contacts that electrically connect electrodes 22A, 22B of leads 20A, 20B, respectively, to a stimulation generator within IMD 16. Leads 20 may deliver electrical stimulation to manage patient symptoms associated with the movement, sleep or speech states. In the example shown in FIG. 1, leads 20 are positioned to provide therapy to patient 12 to manage movement disorders, speech impairment, and sleep impairment. Example locations for leads 20 within brain 28 may include the pedunculopontine nucleus (PPN), thalamus, basal ganglia structures (e.g., the globus pallidus, substantia nigra or subthalamic nucleus), zona inserta, fiber tracts, lenticular fasciculus (and branches thereof), ansa lenticularis, and/or the Field of Forel (thalamic fasciculus).

Leads 20 may be implanted to position electrodes 22A, 22B (collectively "electrodes 22") at desired location of brain 28 through respective holes in cranium 26. Leads 20 may be placed at any location within brain 28 such that electrodes 22 are capable of providing electrical stimulation to target tissue sites within brain 28 during treatment. In the example shown in FIG. 1, electrodes 22 are positioned to deliver stimulation to deep brain sites within brain 28, such as tissue sites under the dura mater surrounding brain 28. For example, in examples, electrodes 22 may be surgically implanted under the dura matter of brain 28 or within the cerebral cortex of brain 28 via a burr hole in cranium 26 of patient 12, and electrically coupled to IMD 16 via one or more leads 20.

Electrodes 22 of leads 20 are shown as ring electrodes. Ring electrodes may be used in DBS applications because they are relatively simple to program and are capable of delivering an electrical field to any tissue adjacent to electrodes 22. In other examples, electrodes 22 may have different configurations. For examples, in some examples, electrodes 22 of leads 20 may define a complex electrode array geometry that is capable of producing shaped electrical fields. The complex electrode array geometry may include multiple electrodes (e.g., partial ring or segmented electrodes) around the perimeter of each lead 20, rather than one ring electrode. In this manner, electrical stimulation may be directed to a specific direction from leads 20 to enhance therapy efficacy and reduce possible adverse side effects from stimulating a large volume of tissue. In some examples, a housing of IMD 16 may include one or more stimulation and/or sensing electrodes. In alternative examples, leads 20 may be have shapes other than elongated cylinders as shown in FIG. 1. For example, leads 20 may be paddle leads, spherical leads, bendable leads, or any other type of shape effective in treating patient 12.

IMD 16 includes a stimulation generator that generates the electrical stimulation delivered to patient 12 via leads 20. Electrical stimulation generated from the stimulation generator may be configured to manage a variety of disorders and conditions. The stimulation generator produces the stimulation in the manner defined by the therapy program selected based on the determined patient condition. In some examples, the stimulation generator may be configured to generate and deliver electrical pulses to treat patient 12. In other examples, the stimulation generator of IMD 16 may be configured to generate and deliver a continuous wave signal, e.g., a sine wave or triangle wave, to brain 28. In either case, IMD 16 generates the electrical stimulation therapy for DBS according to therapy parameter values selected at that given time in therapy based on a detected patient state.

In the example shown in FIG. 1, IMD 16 includes a memory to store a plurality of therapy programs (or parameter sets) defining a set of therapy parameter values. In the case of DBS system 10, the therapy program includes values for a number of parameters that define the stimulation therapy. For example, the therapy parameters may include voltage or current pulse amplitudes, pulse widths, pulse rates, pulse frequencies, electrode combinations, and the like. Upon determining a current state of patient 12, such as by receiving input indicating the current patient state or determining the current patient state based on biosignals, IMD 16 selects a therapy program and generates the electrical stimulation to manage the patient symptoms associated with the determined patient state in order to manage the symptoms associated with the determined patient state, such as symptoms of movement disorders, sleep disorders or speech disorders. Each patient state may be associated with a different therapy program because different therapy programs may provide more effective therapy for a certain patient condition compared to other therapy programs. Accordingly, IMD 16 may store a plurality of programs or programmer 14 may store a plurality of programs that are provided to IMD 16 via wireless telemetry.

During a trial stage in which IMD 16 is evaluated to determine whether IMD 16 provides efficacious therapy to patient 12, a plurality of therapy programs may be tested and evaluated for efficacy relative to the movement, sleep and speech states. Therapy programs may be selected for storage within IMD 16 based on the results of the trial stage. During chronic therapy in which IMD 16 is implanted within patient 12 for delivery of therapy on a non-temporary basis, different therapy programs may be delivered to patient 12 based on a determined state of patient 12. As previously described, in some examples, patient 12 may select the programs for delivering therapy by providing input indicative of the movement state, sleep state or speech state. In other examples, IMD 16 may automatically determine the current state of patient 12 or may receive input from another device that automatically determines that state of patient 12, i.e., without input from patient 12. In addition, patient 12 may modify the value of one or more therapy parameters within a single given program or switch between programs in order to alter the efficacy of the therapy as perceived by patient 12 with the aid of programmer 14 or via volitional patient input detected via an accelerometer, biosignals, voice detector, and the like.

As previously described, IMD 16 may include a memory to store one or more therapy programs. In addition, the memory may associate one or more therapy programs with different patient states, instructions defining the extent to which patient 12 may adjust therapy parameter values, switch between programs, or undertake other therapy adjustments. Patient 12 may generate additional programs for use by IMD 16 via external programmer 14 at any time during therapy or as designated by the clinician.

Generally, IMD 16 is constructed of a biocompatible material that resists corrosion and degradation from bodily fluids. IMD 16 may be implanted within a subcutaneous pocket close to the stimulation site. Although IMD 16 is implanted within a subcutaneous pocket above the clavicle of patient 12 in the example shown in FIG. 1, in other examples, IMD 16 may be implanted within cranium 26, within the patient's back, abdomen or any other suitable place within patient 12.

Programmer 14 is an external computing device that the user, i.e., the clinician and/or patient 12, uses to communicate with IMD 16. For example, programmer 14 may be a clinician programmer that the clinician uses to communicate with IMD 16 and program IMD 16 or run diagnostics on IMD 16. Alternatively, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent the untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that provides information to the user. In addition, programmer 14 may include a keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device may run an application that enables the computing device to operate as medical device programmer 14. A wireless adapter coupled to the computing device may enable communication between the computing device and IMD 16.

When programmer 14 is configured for use by the clinician, programmer 14 may be used to transmit initial programming information to IMD 16. This initial information may include hardware information, such as the type of leads 20 and the electrode arrangement, the position of leads 20 within brain 28, the configuration of electrode array 22, initial programs having therapy parameters, and any other information the clinician desires to program into IMD 16. Programmer 14 may also be capable of completing functional tests (e.g., measuring the impedance of electrodes 26 or the electrodes of leads 20A and 20B).

The clinician also may also store therapy programs within IMD 16 with the aid of programmer 14. During a programming session, the clinician may determine one or more therapy programs that may provide effective therapy to address symptoms associated with the different patient states, i.e., a movement state, sleep state, and speech state of patient 12. Patient 12 may provide feedback to the clinician as to the efficacy of the specific program being evaluated. Once the clinician has identified one or more programs that may be beneficial to each of the movement, sleep, and speech states of patient 12, patient 12 may continue the evaluation process and identify the one or more programs that best mitigate symptoms associated with the movement state, the one or more programs that best mitigate symptoms associated with the sleep state, and the one or more programs that best mitigate symptoms associated with the speech state. In some cases, the same therapy program may be applicable to two or more patient states. Programmer 14 may assist the clinician in the creation/identification of therapy programs by providing a methodical system of identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust certain therapy parameter values or set an available range for a particular therapy parameter. In addition, in some examples, patient 12 may provide input via the user interface of programmer 14 to indicate a patient state, and programmer 14 may subsequently select a therapy program that is associated with the selected patient state or provide an indication to IMD 16, which may select a therapy program. In some examples, programmer 14 includes dedicated buttons for each of the movement, sleep, and speech states. In other examples, buttons of programmer 14 (e.g., defined by a physical keypad or a touch screen) may include multifunctional buttons, and in one function, patient 12 may indicate the current patient state via the multifunction buttons.

Programmer 14 may also provide an indication to patient 12 when therapy is being delivered, when patient input or automatic detection of a patient state has triggered a change in therapy or when IMD 16 or when the power source within programmer 14 or IMD 16 need to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 14 may also communicate with another programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

DBS system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for long-term treatment.

Figure 2:
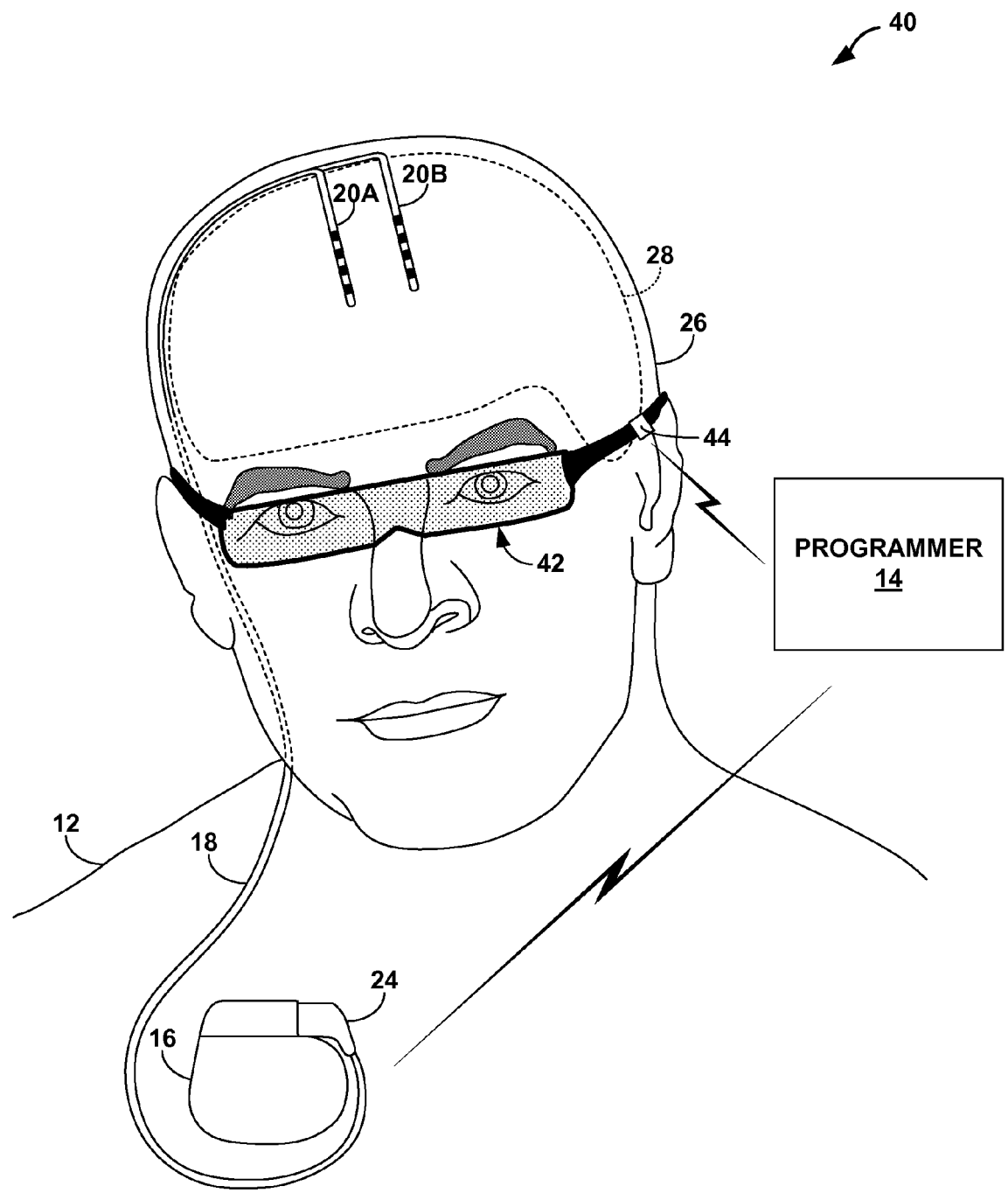
FIG. 2 is a schematic diagram of another example therapy system, which includes an external cue device, an implanted medical device, and a programmer.

FIG. 2 is a schematic diagram of another example therapy system 40, which includes an external cue device 42 in addition to IMD 16. Therapy system 40 may improve the performance of motor tasks by patient 12 that may otherwise be difficult. These tasks include at least one of initiating movement, maintaining movement, grasping and moving objects, improving gait associated with narrow turns, and so forth. External cue device 42 is any device configured to deliver an external cue to patient 12. External cue device 42 generates and delivers a sensory cue, such as a visual, auditory or somatosensory cue (e.g., a pulsed vibration) to patient 12. A different sensory cue may be delivered to patient 12 depending on whether patient 12 is in a movement, sleep or speech state. For example, if patient 12 is prone to gait freeze or akinesia, one type of sensory cue may help patient 12 initiate or maintain movement. In other examples, external cues delivered by external cue device 42 may be useful for controlling other movement disorder conditions, such as, but not limited to, rigidity, bradykinesia, rhythmic hyperkinesia, and nonrhythmic hyperkinesias, as well as speech disorders.

Therapy system 40 may include a processor or other computing device that selects therapy delivery by at least one of IMD 16 or external cue device 42 based on the determined patient state. For example, in some cases, DBS delivered by IMD 16 may be more effective in managing a sleep disorder than delivery of a sensory cue by external cue device 42. Visual cues, auditory cues or somatosensory cues may have different effects on patient 12. For example, in some patients with Parkinson's disease, an auditory cue may help the patients grasp moving objects, whereas somatosensory cues may help improve gait and general mobility. However, the type of therapy that best addresses the patient condition may be specific to the patient. Accordingly, a clinician may customize therapy system 40 to a particular patient 12.

Although external cue device 42 is shown as an eyepiece worn by patient 12 in the same manner as glasses, in other examples, external cue device 42 may have different configurations. For example, if an auditory cue is desired, an external cue device may take the form of an ear piece (e.g., an ear piece similar to a hearing aid or head phones). As another example, if a somatosensory cue is desired, an external cue device may take the form of a device worn on the patient's arm or legs (e.g., as a bracelet or anklet), around the patient's waist (e.g., as a belt) or otherwise attached to the patient in a way that permits the patient to sense the somatosensory cue. A device coupled to the patient's wrist, for example, may provide pulsed vibrations.

External cue device 42 includes receiver 44 that is configured to communicate with programmer 14 and IMD 16 via a wired or wireless signal. Accordingly, IMD 16 may include a telemetry module that is configured to communicate with receiver 44. Examples of local wireless communication techniques that may be employed to facilitate communication between IMD 16 and receiver 44 of external cue device 42 include conventional RF telemetry techniques for medical devices, or other communication techniques such as those conforming to the Bluetooth or IEEE 802.11x standards.

As previously described, IMD 16 may include a patient state module that determines whether patient 12 is in a movement state, sleep state or speech state. For example, electrodes 22 of leads 20 may be configured to detect a biosignal within brain 28, and IMD 16 may include a processor that determines what state the bioelectrical signal indicates, if any. IMD 16 may select a therapy program based on the determined patient state, such as by choosing and executing a stored therapy program or by modifying at least one parameter value of a stored therapy program based on the determined patient state. IMD 16 may transmit a signal to receiver 44 of external cue device 42 that indicates either the determined patient state, the therapy program to deliver, an indication of a therapy program (e.g., an alphanumeric reference indication with which external cue device 42 may associate a stored therapy program) or adjustments to a therapy program.

For example, upon detecting a movement state based on EEG signals, IMD 16 may transmit a signal to receiver 44. A controller within external cue device 42 may initiate the delivery of the external cue in response to receiving the signal from receiver 44. In some cases, external cue device 44 may also include a motion detection element (or a "motion sensor"), such as an accelerometer. External cue device 42 may transmit the signals from the motion detection element to IMD 16, which may process the signals to determine whether patient 12 has stopped moving. Upon detecting that patient 12 has stopped moving (e.g., via patient input, brain signals or sensors that detect movement) or upon expiration of a timer, IMD 16 may provide a control signal to external cue device 42 via transmitter 44 that deactivates the delivery of the cue. In other examples, external cue device 42 may include a processor that process the signals from the motion detection element and a controller that deactivates the cue delivery upon detecting patient 12 has stopped moving, i.e., is in a rest state.

Automatic selection of a therapy program for external cue device 42 and automatic activation of external cue device 42 in response to the detected patient state may help provide patient 12 with better control and timing of external cue device 42 by eliminating the need for patient 12, who may exhibit some difficulty with movement, to initiate the system 40. In addition, automatically initiating the delivery of a sensory cue in response to detecting a movement, sleep or speech state enables therapy system 40 to minimize the time between when patient 12 needs the therapy and when the therapy is actually delivered. Therapy system 40 provides a responsive system for controlling the delivery of therapy to patient 12, and times the delivery of therapy such that patient 12 receives the therapy at a relevant time, i.e., when it is particularly useful to patient 12.

Programmer 14 may be configured to communicate with external cue device 42 via any of the aforementioned local wireless communication techniques, such as RF telemetry or infrared communication techniques. Patient 12 or a clinician may modify the external cues delivered by external cue device 42 with the aid of programmer 14. For example, patient 12 may decrease or increase the contrast or brightness of a visual cue, increase or decrease the longevity of the visual cue, increase or decrease the volume of an auditory cue, and so forth.

In some cases, an effective therapy system to manage a patient's movement, sleep and speech states may include external cue device 44 and a sensing device to detect the patient state. In such cases, IMD 16 may be eliminated from therapy system 40.

In other examples, an implanted device may be configured to deliver a sensory cue to patient 12. For example, IMD 16 may deliver stimulation to a visual cortex of brain 28 of patient 12 in order to simulate a visual cue. Stimulating the visual cortex may generate a visible signal to patient 12 that provides a substantially similar effect as an external visual cue. A sensory cue provided via IMD 16 may be more discreet than a sensory cue provided by external cue device 42.

FIG. 3 is a functional block diagram illustrating components of an example IMD 16. In the example of FIG. 3, IMD 16 generates and delivers electrical stimulation therapy to patient 12. IMD 16 includes processor 50, memory 52, stimulation generator 54, telemetry module 56, power source 58, and patient state module 59. Memory 52 may include any volatile or non-volatile media, such as a random access memory (RAM), read only memory (ROM), non-volatile RAM (NVRAM), electrically erasable programmable ROM (EEPROM), flash memory, and the like. Memory 52 may store instructions for execution by processor 50, such as, but not limited to, therapy programs defining one or more stimulation parameter values with which stimulation generator 54 may generate electrical stimulation signals, information associating therapy programs with the movement, sleep and speech states, and any other information regarding therapy of patient 12. Therapy information may be recorded for long-term storage and retrieval by a user. As described in further detail with reference to FIG. 4, memory 52 may include separate memories for storing instructions, therapy programs, and patient information. In some examples, memory 52 stores program instructions that, when executed by processor 50, cause IMD 16 and processor 50 to perform the functions attributed to them herein.

Processor 50 controls stimulation generator 54 to generate and deliver electrical stimulation therapy via one or more leads 20 (FIGS. 1 and 2). An example range of electrical stimulation parameter values that may be effective in DBS to manage patient symptoms present during the movement state include:

1. Frequency: between approximately 100 Hz and approximately 500 Hz, such as approximately 130 Hz.

2. Voltage Amplitude: between approximately 0.1 volts and approximately 50 volts, such as between approximately 0.5 volts and approximately 20 volts, or approximately 5 volts. In other examples, a current amplitude may be defined.

3. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms.

4. Pulse Width: between approximately 10 microseconds and approximately 5000 microseconds, such as between approximately 100 microseconds and approximately 1000 microseconds, or between approximately 180 microseconds and approximately 450 microseconds.

Other ranges of therapy parameter values may be used, and may change if the stimulation is delivered to a region of patient 12 other than brain 28. While stimulation pulses are described, stimulation signals may be of any form, such as continuous-time signals (e.g., sine waves) or the like.

An example range of electrical stimulation parameter values that may be effective in DBS to manage symptoms present during a speech state include:

1. Frequency: between approximately 0.5 Hz and approximately 200 Hz, such as approximately 70 Hz to approximately 185 Hz.

2. Amplitude: between approximately 0.1 volts and approximately 50 volts, such as between approximately 0.5 volts and approximately 20 volts, or approximately 5 volts. In other examples, a current amplitude may be defined as the biological load in the voltage is delivered.

3. Pulse Width: between approximately 10 microseconds and approximately 5000 microseconds, such as between approximately 100 microseconds and approximately 1000 microseconds, or between approximately 180 microseconds and approximately 450 microseconds.

An example range of electrical stimulation parameter values that may be effective in DBS to manage symptoms present during a sleep state include:

1. Frequency: between approximately 0.1 Hz and approximately 500 Hz, such as between approximately 0.5 Hz and 200 Hz. In some cases, the frequency of stimulation may change during delivery of stimulation, and may be modified, for example, based on the sensed sleep stage or a pattern of sensed brain signals during the sleep state. For example, the frequency of stimulation may have a pattern within a given range, such as a random or pseudo-random pattern within a frequency range of approximately 5 Hz to approximately 150 Hz around a central frequency. In some examples, the waveform may also be shaped based on a sensed signal to either be constructive or destructive in a complete or partial manner, or phased shifted from about 0 degrees to about 180 degrees out of phase.

2. Amplitude: between approximately 0.1 volts and approximately 50 volts. In other examples, rather than a voltage-controlled system, the stimulation system may control the current.

3. Pulse Width: between approximately 10 microseconds and approximately 5000 microseconds, such as between approximately 100 microseconds and approximately 1000 microseconds, or between approximately 180 microseconds and approximately 450 microseconds.

The electrical stimulation parameter values provided above, however, may differ from the given ranges depending upon the particular patient and the patient state. For example, with respect to the sleep state, the stimulation parameter values may be modified based on the sleep state during which electrical stimulation is provided (e.g., the REM state, non-REM state, and so forth).

In some examples, it may be desirable for stimulation generator 54 to deliver stimulation to patient 12 during the REM sleep stages, and deliver minimal or no stimulation during the NREM sleep stages. In such examples, the sleep state may be defined as the REM sleep stage. These and other techniques for modifying stimulation therapy to patient 12 based on a detected sleep stage of the sleep state are described in U.S. patent application Ser. No. 12/238,105 to Wu et al. entitled, "SLEEP STAGE DETECTION" and filed on the same date as the present disclosure and U.S. Provisional Application No. 61/049,166 to Wu et al., entitled, "SLEEP STAGE DETECTION" and filed on Apr. 30, 2008. The entire contents of U.S. patent application Ser. No. 12/238,105 to Wu et al. and U.S. Provisional Application No. 61/049,166 to Wu et al. are incorporated herein by reference.

Processor 50 may include any one or more of a microprocessor, a controller, a digital signal processor (DSP), an application specific integrated circuit (ASIC), a field-programmable gate array (FPGA), discrete logic circuitry, or the like. The functions attributed to processor 50 herein may be implemented as software, firmware, hardware or any combination thereof. In addition to controlling stimulation generator 54, processor 50 may control patient state module 59. Patient state module 59 determines a current state of patient 12 or provides information to processor 50, which determines a current state of patient 12 based on the information from patient state module 59. As described in further detail below, in some examples, patient state module 59 may include a motion sensor (or "detector"), such as an accelerometer, which generates a signal indicative of the patient's posture or activity level. Processor 50 or a processor within patient state module 59 may analyze the output from the motion detector to determine the current patient state.

In other examples, patient state module 59 may include a receiver that receives a signal indicative of a voice command. Patient 12 may indicate a current state via a voice input that is detected by an external or implanted voice detector. The voice detector may be integral with patient state module 59 or patient state module 59 may receive a signal from the voice detector indicative of the current patient state, e.g., via RF communication techniques. The voice detector may, for example, detect a pattern of inflections in the patient's voice to determine whether patient 12 has provided input to indicate a current patient state and if so, whether the patient's input indicates the movement, sleep or speech states. In other examples, patient state module 59 may include a biosignal detection module that generates a signal indicative of a detected biosignal or provides a raw brain signal (e.g., an EEG signal) to processor 50, which analyzes the brain signal to detect a biosignal.

If patient state module 59 determines the patient's current state, patient state module 59 may generate a patient state indication. The patient state indication may be a value, flag, or signal that is stored or transmitted to processor 50 or directly to stimulation generator 54 to indicate that patient 12 is in at least one of a movement, sleep or speech state. Patient state module 59 may transmit the patient state indication to processor 50 of IMD 16 or to another device, such as external cue device 42 (FIG. 2) or programmer 14 (FIG. 1) via telemetry module 56, which, in response, may select a therapy program and control the delivery of therapy accordingly. Alternatively, patient state module 59 may select a therapy program from memory 52 (e.g., by selecting a stored therapy program or selecting instructions reflecting modifications to one or more parameter values of a stored therapy program) and transmit the selected therapy program to processor 50 or external cue device 42. The "selected" therapy program may include, for example, the stored program selected from memory 52 based on the determined patient state, a stored therapy program and instructions indicating modifications to be made to a stored therapy program based on the determined patient state, a stored therapy program that has already been modified, or indicators of any of the aforementioned therapy programs (e.g., alphanumeric indicators associated with the therapy program). In some examples, processor 50 may record information relating to the patient state indication, e.g., the date and time of the particular patient state, in memory 52 for later retrieval and analysis by a clinician.

Processor 50 controls telemetry module 56 to send and receive information. Telemetry module 56 in IMD 16, as well as telemetry modules in other devices described herein, such as programmer 14, may accomplish communication by any suitable communication techniques, such as RF communication techniques. In addition, telemetry module 56 may communicate with external medical device programmer 14 via proximal inductive interaction of IMD 16 with programmer 14. Accordingly, telemetry module 56 may send information to external programmer 14 on a continuous basis, at periodic intervals, or upon request from IMD 16 or programmer 14.

Power source 58 delivers operating power to various components of IMD 16. Power source 58 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

FIG. 4 is a block diagram illustrating an example configuration of memory 52 of IMD 16. In the example of FIG. 4, memory 52 stores therapy programs table 60, patient state information 61, patient information 62, and diagnostic information 63. Therapy programs table 60 may store the therapy programs as a plurality of records that are stored in a table or other data structure that associate therapy programs with an indication of whether the program is associated with the movement, sleep, and/or speech states. While the remainder of the disclosure refers primarily to tables, the present disclosure also applies to other types of data structures that store therapy programs and associated physiological parameter values.

In the case of electrical stimulation therapy, each of the programs includes respective values for a plurality of therapy parameter values, such as pulse amplitude, pulse width, pulse rate, and electrode combination. The electrode combination may include an indication of electrodes 22 (FIG. 1) of leads 20 that are selected for delivering stimulation signals to brain 28 and the respective polarity of the selected electrodes. Processor 50 of IMD 16 or patient state module 59 may select one or more programs based on a determined patient state. Programs 60 may have been generated using a clinician programmer, e.g., during an initial or follow-up programming session, and received by processor 50 from the clinician programmer via telemetry module 56. In other examples, programmer 14 may store stores programs 60, and processor 50 of IMD 16 may receive selected programs from programmer 14 via telemetry circuit 56.

Patient state information 61 may store information associating various patient state indicators, e.g., biosignals or signals from an accelerometer, with the respective patient state. For example, if patient state module 59 determines a current patient state based on a biosignal detected within brain 28 of patient 12, patient state information 61 may store a plurality of biosignal templates, where each template corresponds to at least one of the movement, sleep or speech states. Processor 50 or a processor within patient state module 59 may then determine whether a detected electrical signal from brain 28 is a biosignal and if so, whether the biosignal is indicative of a movement, sleep or speech state.

Patient information 62 in memory 52 may store data relating to patient 12, such as the patient's name and age, the type of IMD 16 or leads 20 implanted within patient 12, and so forth. Processor 50 of IMD 16 may also collect diagnostic information 63 and store diagnostic information 63 within memory 52 for future retrieval by a clinician. Diagnostic information 63 may, for example, include selected recordings of the output of patient state module 59. In examples, diagnostic information 63 includes information identifying the time at which the different patient states occurred. Diagnostic information 63 may include other information or activities indicated by patient 12 using programmer 14, such as changes in symptoms, medication ingestion or other activities undertaken by patient 12, as well as other physiological parameter values (e.g., EEG or ECoG values, blood pressure, body temperature, patient activity level, electrocardiogram (ECG) data, and the like) that may be measured by IMD 16 or by another sensing module, which may be a part of IMD 16 or separate from IMD 16. A clinician may review diagnostic information 63 in a variety of forms, such as timing diagrams, or a graph resulting from statistical analysis of diagnostic information 63, e.g., a bar graph. The clinician may, for example, download diagnostic information 63 from IMD 16 via a programmer 14 or another computing device. Diagnostic information 63 may also include calibration routines for electrodes 20 (FIG. 1) and malfunction algorithms to identify stimulation dysfunctions.

FIG. 5 illustrates an example therapy programs table 60 stored within memory 52. Processor 50 may search table 60 based on a currently-detected patient state in order to match therapy to a determined patient state. As shown in FIG. 5, table 60 includes a plurality of records. Each record contains an indication of a patient state, i.e., the movement, sleep or speech states, as well as an associated therapy program. The indication of the patient states may be stored as, for example, a stored value, flag or other indication that is unique to the particular patient state. Thus, although table 60 shown in FIG. 5 shows the patient states as "MOVEMENT," "SLEEP" or "SPEECH," within memory 52, the patient states may in another computer-readable format.

In examples in which patient state module 59 determines a current patient state based on a signal generated by a 3-axis accelerometer, patient state indicators stored within table 60 may be accelerometer outputs or a specific pattern of accelerometer outputs. When patient 12 taps the accelerometer to provide input indicating the movement, sleep or speech states, processor 50 may match the accelerometer output with the stored outputs in table 60 and select a therapy program based on the best match with the accelerometer output. Alternatively, accelerometer outputs corresponding to the patient states may be stored within patient state information 61 (FIG. 4) portion of memory 52.

In examples in which patient state module 59 determines a current patient state based on a biosignal, patient state indicators stored within table 60 may be a biosignal template or amplitude value. In other examples, patient state module 59 may determine a patient state based on other input from patient 12, e.g., voice commands or based on other input from sensors, e.g., physiological sensors. In those examples, table 60 or patient state information 61 may store the relevant information as an indicator of a patient state. For example, in the case of physiological sensors, table 60 may associate physiological sensor outputs with the movement, sleep, and speech states.

In the example of therapy programs table 60 shown in FIG. 5, the therapy parameter values of each therapy program are shown in table 60, and include an amplitude, a pulse width, a pulse frequency, and an electrode configuration. The amplitude is shown in volts, the pulse width is shown in microseconds (μs), the pulse frequency is shown in Hertz (Hz), and the electrode configuration determines the selected electrodes 22 (FIG. 1) and polarity used for delivery of stimulation according to the record. The amplitude of program table 60 is the voltage amplitude, in Volts (V), but other examples of table 60 may store a current amplitude. In the illustrated example, each record includes a complete set of therapy parameter values, e.g., a complete program, as therapy information. In other examples, each record may include one or more individual parameter values, or information characterizing an adjustment to one or more parameter values.

For some patient conditions, different therapy programs may be effective for different types of patient movement or different stages of a movement state. For example, different sets of electrodes may be activated to target different tissue sites depending on the patient's posture or activity level. As another example, therapy parameter values may be modified for different stages of a patient's movement state, e.g., a first therapy program may be selected to help patient 12 initiate movement and a second therapy program may be subsequently delivered, e.g., by detecting another stage of the movement state, to help prevent alleviate tremors. In some examples, multiple therapy programs may be selected to address two or more of the movement, speech or sleep states at substantially the same time. For example, the stimulation therapy according to the multiple selected programs may be delivered simultaneously or on a time-interleaved basis, either in an overlapping or non-overlapping manner.

In some examples, memory 52 also may store different therapy programs for different patient postures or activity levels, thereby enabling processor 50 to titrate therapy parameter values based on different stages of a movement state. In FIG. 5, table 60 illustrates two different programs for a patient's movement state, where each movement state therapy program is associated with a different patient posture or activity level. Upon detecting a movement state, IMD 16 or another device may determine a patient's posture or activity level and select a therapy program from table 60 that is best associated with the determined posture or activity level.

Processor 50 or another processor may determine a patient's posture or activity level using any suitable technique, such as by output from one or more accelerometers or physiological signals, such as heart rate, respiration rate, respiratory volume, core temperature, blood pressure, blood oxygen saturation, partial pressure of oxygen within blood, partial pressure of oxygen within cerebrospinal fluid, muscular activity, arterial blood flow, electromyogram (EMG), an EEG, an ECG or galvanic skin response. Processor 50 may associate the signal generated by a 3-axis accelerometer or multiple single-axis accelerometers (or a combination of a three-axis and single-axis accelerometers) with a patient posture, such as sitting, recumbent, upright, and so forth, and may associate physiological parameter values with patient activity level. For example, processor 50 may process the output from accelerometers located at a hip joint, thigh or knee joint flexure coupled with a vertical orientation sensor (e.g., an accelerometer) located on the patient's torso or head in order to determine the patient's posture.

Suitable techniques for determining a patient's activity level or posture are described in U.S. Patent Application Publication No. 2005/0209644, entitled, "COLLECTING ACTIVITY INFORMATION TO EVALUATE THERAPY," and U.S. patent application Ser. No. 11/799,035, entitled, "THERAPY ADJUSTMENT." U.S. Patent Application Publication No. 2005/0209644 and U.S. patent application Ser. No. 11/799,035 are incorporated herein by reference in their entireties. As described in U.S. Patent Application Publication No. 2005/0209644, a processor may determine an activity level based on a signal from a sensor, such as an accelerometer, a bonded piezoelectric crystal, a mercury switch or a gyro, by sampling the signal and determining a number of activity counts during the sample period. For example, processor 50 may compare the sample of a signal generated by an accelerometer or piezoelectric crystal to one or more amplitude thresholds stored within memory 52. Processor 50 may identify each threshold crossing as an activity count. Where processor 50 compares the sample to multiple thresholds with varying amplitudes, processor 50 may identify crossing of higher amplitude thresholds as multiple activity counts. Using multiple thresholds to identify activity counts, processor 50 may be able to more accurately determine the extent of patient activity for both high impact, low frequency and low impact, high frequency activities, which may each be best managed by a different therapy program.

In addition to describing techniques for detecting a value of a patient parameter, such as patient posture or activity level, U.S. patent application Ser. No. 11/799,035 describes techniques adjusting a therapy program to accommodate the detected parameter value. As described in U.S. patent application Ser. No. 11/799,035, if a sensed patient parameter value is not associated with a stored therapy program, a processor of a medical device, programming device or another computing device implements an algorithm to interpolate between two stored therapy programs to temporarily create a therapy program that provides efficacious therapy for the sensed patient parameter value.

Other techniques for determining an activity level or posture of patient 12 are contemplated. In addition, in some examples, memory 52 may also store different therapy programs for different stages of the sleep state (e.g., NREM or REM sleep) or different speech stages, as described in U.S. patent application Ser. No. 12/238,105 to Wu et al. entitled, "SLEEP STAGE DETECTION" and filed on the same date as the present disclosure and U.S. Provisional Application No. 61/049,166 to Wu et al., entitled, "SLEEP STAGE DETECTION" and filed on Apr. 30, 2008.

In other examples, rather than storing a plurality of parameter values for each therapy program, table 60 may store modifications to the different therapy parameter values from a baseline or another stored therapy program. For example, if IMD 16 delivers stimulation to patient 12 at an amplitude of about 2 V, a pulse width of about 200 μs, a frequency of about 10 Hz, table 60 may indicate that upon detecting a movement state, processor 50 should control stimulation generator 54 to deliver therapy with a frequency of about 130 Hz. The modification may be achieved by switching between stored programs or by adjusting a therapy parameter for an existing, stored program.

The modifications to parameter values may be stored in absolute or percentage adjustments for one or more therapy parameter values or a complete therapy program. For example, in table 60 shown in FIG. 5, rather than providing an absolute amplitude value, "2.0V" in Record 1, the therapy programs table may indicate "+0.5 V" to indicate that if the movement state is detected, the amplitude should be increased by 0.5 V or "−0.25 V" to indicate that if the movement state is detected, the amplitude should be decreased by 0.25 V. Instructions for modifying the other therapy parameters, such as pulse width, frequency, and electrode configuration, may also be stored in a table.

Although therapy programs table 60 is described with reference to memory 52 of IMD 16, in other examples, programmer 14 or another device may store different therapy programs and indications of the associated movement, sleep or patient state. The therapy programs and respective patient states may be stored in a tabular form, as with therapy programs table 60 in FIG. 5, or in another data structure format.

Figure 6:
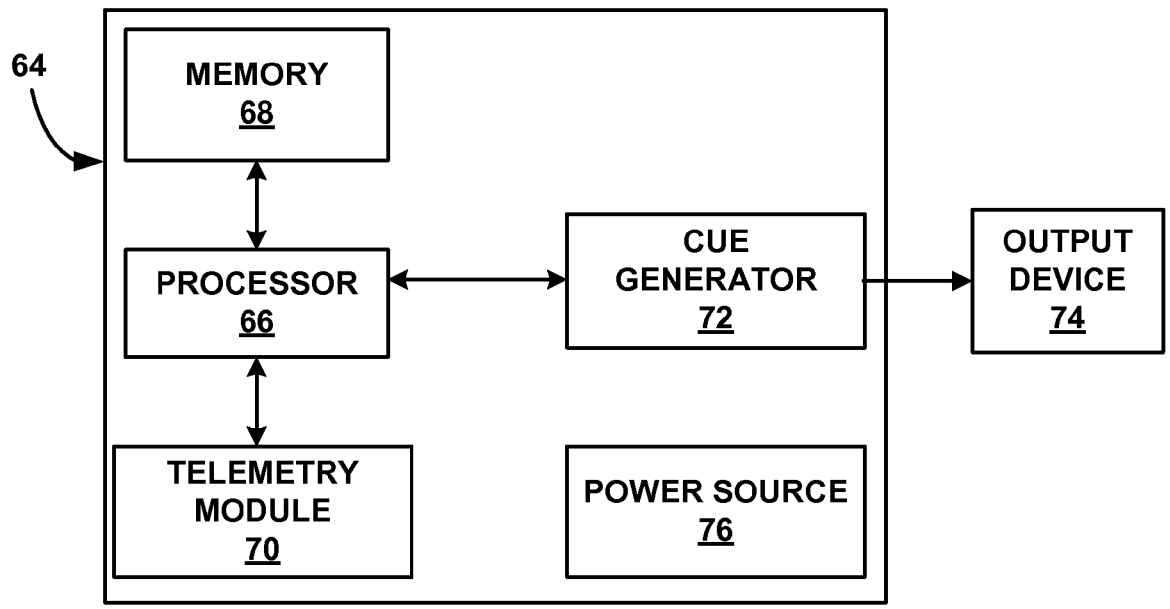
FIG. 6 is functional block diagram illustrating components of an example sensory cue device.

FIG. 6 is a functional block diagram of an example therapy module 64, which may be incorporated into an external cue device, such as external cue device 42 of FIG. 2. Therapy module 64 includes processor 66, memory 68, telemetry module 70, cue generator 72, output device 74, and power source 76. Processor 66, memory 68, telemetry module 70, and power source 76 of therapy module 64 may be similar to processor 50, memory 52, telemetry module 56, and power source 58, respectively, of IMD 16.

As shown in FIG. 6, therapy module 64 includes cue generator 72 coupled to output device 74. Upon receiving a control signal from patient state module 59 that indicates a determined patient state, processor 66 may control cue generator 72 to generate a sensory cue and deliver the cue to patient 12 via output device 74. Processor 66 may select parameter values for the sensory cue from a plurality of stored therapy programs stored within memory 68 based on the determined patient state. Memory 68 may be similar to memory 52 of IMD 16 described above with respect to FIGS. 3-5. In particular, memory 68 may store a plurality of therapy programs and associate the therapy programs with at least two of the movement, sleep, and speech states. In this manner, therapy module 64 is configured to manage multiple symptoms of the patient's condition.

Output device 74 may be any device configured to create a stimulus for patient 12. As previously described, example stimuli may include light, sound, vibration, any combination thereof or other visual, auditory or somatosensory cues. For example, in some examples, output device 74 may be an LED mounted on the inside of the frame of external cue device 42 (FIG. 2) or an LCD screen. In some examples, therapy module 64 may include multiple output devices 74 that each deliver a different stimuli. The movement, sleep, and speech states may be associated with a respective one of the different stimuli.

Processor 66 may control telemetry module 70 to send and receive information to and from programmer 14, IMD 16 or another device. Telemetry module 70 may include receiver 44 (FIG. 1). Wireless communication may be accomplished by RF communication or proximal inductive interaction of therapy module 64 with the other wireless device. Accordingly, telemetry module 70 may send or receive information from patient state module 59 or processor 50 of IMD 16, or external programmer 14 on a continuous basis, at periodic intervals, or upon request from the implantable stimulator or programmer.

Cue generator 72 includes the electrical circuitry needed to generate the stimulus delivered by output device 74. For example, cue generator 72 may modulate the color of light emitted by output device 74, the intensity of light emitted by output device 74, the frequency of sound waves or vibrations delivered by output device 74, or any other therapy parameter of the output device.

In some examples, output device 74 may be a display that is capable of producing patterns of light, images, or other representations on the output device itself or projected onto another surface for patient 12 to see. In this manner, the visual cue or stimulus may be more complex than a simple light or sound. For example, output device 74 may deliver a sequence of colored shapes that causes the symptoms of the patient condition to subside. Alternatively, one or more words, numbers, symbols or other graphics may produce a desired affect to treat patient 12. When output device 74 is a display, the output device may be embodied as a LCD, head-up display, LCD projection, or any other display technology available to the manufacturer of therapy module 64.

While FIGS. 1 and 2 illustrate therapy systems that include IMD 16 configured to deliver electrical stimulation and external cue device 42, in other examples, a therapy system may include a fluid delivery device, such as a drug pump, in addition to or instead of IMD 16 or external cue device 42.

Figure 7:
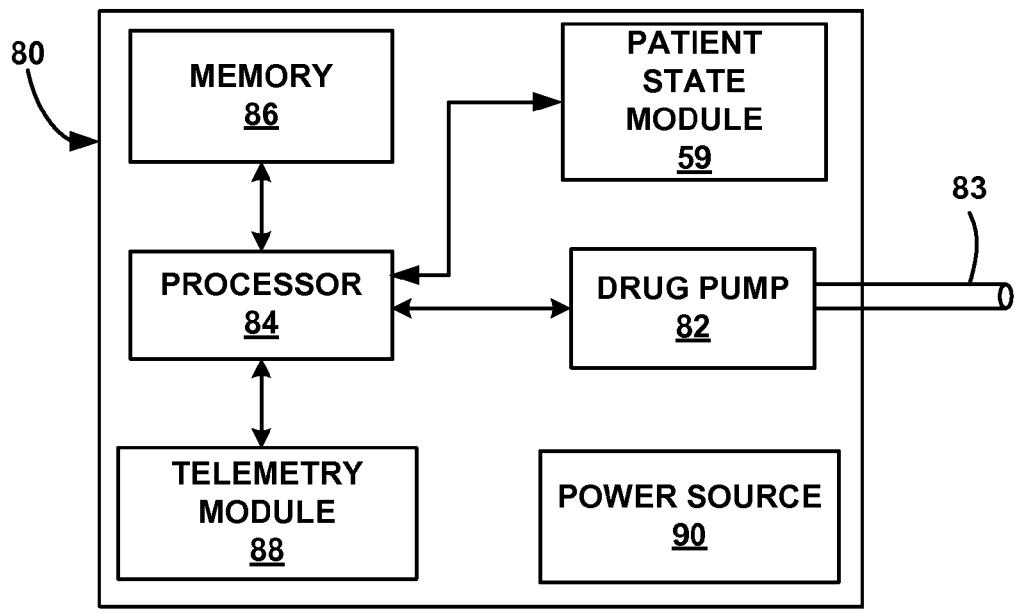
FIG. 7 is functional block diagram illustrating components of an example drug pump.

FIG. 7 is functional block diagram illustrating components of an example medical device 80 that includes drug pump 82. Medical device 80 may be used in therapy system 10 (FIG. 1) or other therapy systems in which a therapy program is selected based on whether patient 12 in a movement, sleep or speech state. Medical device 80 may be implanted or carried externally to patient 12. As shown in FIG. 7, medical device 80 includes patient state module 59, drug pump 82, processor 84, memory 86, telemetry module 88, and power source 90. Processor 84 controls drug pump 82 to deliver a specific quantity of a pharmaceutical agent to a desired tissue within patient 12 via catheter 83 at least partially implanted within patient 12. In some examples, medical device 80 may include a stimulation generator for producing electrical stimulation in addition to delivering drug therapy. Patient state module 59, processor 84, memory 86, telemetry module 88, and power source 90 may be substantially similar to patient state module 59, processor 50, memory 52, telemetry module 56, and power source 58, respectively, of IMD 16 (FIG. 3).

Medical device 80 is configured to deliver a drug (i.e., a pharmaceutical agent or another therapeutic agent) or another fluid to tissue sites within patient 12. As previously described, patient state module 59 is configured to determine whether patient 12 is in a movement, speech or sleep state. Patient state module 59 may transmit a signal to processor 84 that indicates the determined patient state, and processor 84 may control drug pump 82 to deliver therapy based on the determined patient state. For example, processor 84 may select a therapy program from memory 52 based on the determined patient state, such as by selecting a stored program or modifying a stored program, where the program includes different fluid delivery parameter values, and control drug pump 82 to deliver a pharmaceutical agent or another fluid to patient 12 in accordance with the selected therapy program. The different fluid delivery parameters may, for example, dictate a different type of pharmaceutical agent if patient 12 is in a movement state compared to a sleep state. Alternatively, the bolus size or frequency of bolus delivery may differ based on the determined patient state.

Processor 84 controls the operation of medical device 80 with the aid of instructions that are stored in memory 86, which is similar to the control of IMD 16. For example, the instructions may dictate the bolus size of a drug that is delivered to patient 12 when patient state module 59 determines patient 12 is in a speech state.

In other examples of IMD 16 (FIG. 3) and medical device 80 (FIG. 7), the respective patient state module 59 may be disposed in a separate housing. In such examples, patient state module 59 may communicate wirelessly with IMD 16 or medical device 80, thereby eliminating the need for a lead or other elongated member that couples the patient state module 59 to IMD 16 or medical device 80. Examples of patient state module 59 are described below with reference to FIGS. 10 and 11.

While the remainder of the disclosure may primarily refer to IMD 16, in other examples, the disclosure is also applicable to external cue device 42, medical device 80, as well as any other therapy delivery device.

Figure 8:
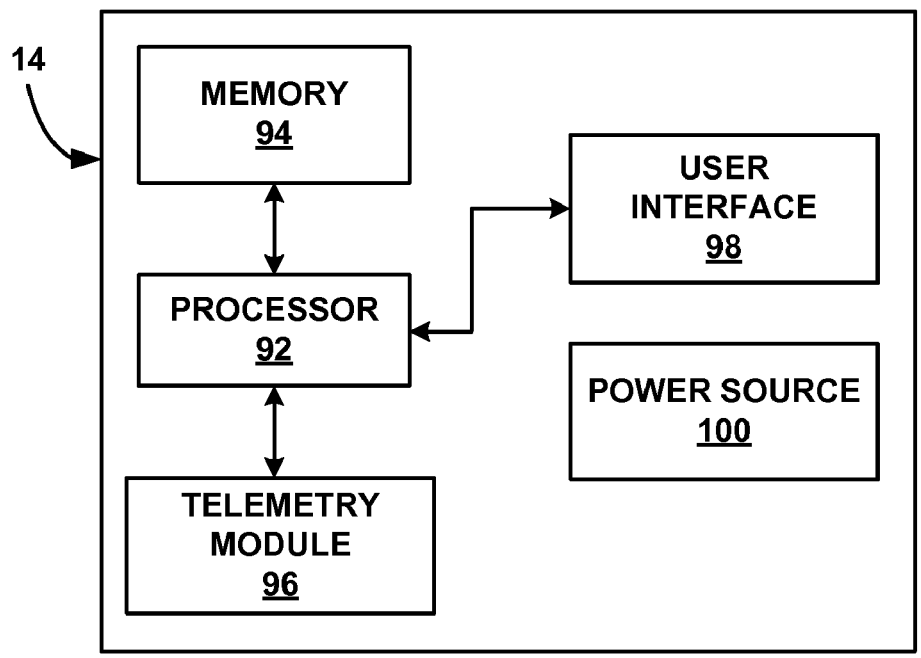
FIG. 8 is a functional block diagram illustrating components of an example medical device programmer.

FIG. 8 is a conceptual block diagram of an example external medical device programmer 14, which includes processor 92, memory 94, telemetry module 96, user interface 98, and power source 100. Processor 92 controls user interface 98 and telemetry module 96, and stores and retrieves information and instructions to and from memory 94. Programmer 14 may be configured for use as a clinician programmer or a patient programmer.

The user, such as a clinician or patient 12, may interact with programmer 14 through user interface 98. User interface 98 may include a display (not shown), such as an LCD or other screen, to show information related to the therapy and input controls (not shown) to provide input to programmer 14. Input controls may include buttons, a keypad (e.g., an alphanumeric keypad or a reduced set of buttons), a peripheral pointing device or another input mechanism that allows the user to navigate though the user interface of programmer 14 and provide input, e.g., to indicate whether patient 12 is in a movement, sleep or speech state.

If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display.

Processor 92 monitors activity from the input controls and controls the display of user interface 98. In some examples, the display may be a touch screen that enables the user to select options directly from the display. In other examples, user interface 98 also includes audio circuitry for providing audible instructions or sounds to patient 12 and/or receiving voice commands from patient 12. As previously described, patient 12 may provide input to programmer 14 to indicate the current patient state via voice commands that are received and interpreted by the audio circuitry.

Patient 12 may use programmer 14 to provide input that indicates whether patient 12 is in a movement, sleep or speech state using techniques other than or in addition to voice commands. For example, prior to initiating movement, sleep or speech, patient 12 may depress a button of user interface 98. Processor 92, which is electrically coupled to user interface 98, may then transmit a signal to IMD 16 via telemetry module 96, to indicate the patient state. Patient state module 59 of IMD 16 may receive the signal from programmer 14 via its respective telemetry module 56 (FIG. 3). Processor 50 of IMD 16 may select a stored therapy program from memory 52 based on the received signal indicating the patient condition. Alternatively, processor 92 of programmer 14 may select a therapy program and transmit a signal to IMD 16, where the signal indicates the therapy parameter values to be implemented by IMD 16 during therapy delivery to manage the particular patient condition or provides an indication of the selected therapy program that is stored within memory 52 of IMD 16.

Patient 12, a clinician or another user may also interact with programmer 14 to manually select therapy programs, generate new therapy programs, modify therapy programs through individual or global adjustments, and transmit the new programs to IMD 16. In a learning mode, programmer 14 may allow patient 12 and/or the clinician to determine which therapy programs are best suited for the movement, sleep and speech states.

Memory 94 may include instructions for operating user interface 98, telemetry module 96 and managing power source 100. In addition, memory 94 may include instructions for guiding patient 12 through the learning mode when correlating therapy programs with the movement, sleep and speech states. Memory 94 may also store any therapy data retrieved from IMD 16 during the course of therapy. The clinician may use this therapy data to determine the progression of the patient condition in order to predict future treatment. Memory 94 may include any volatile or nonvolatile memory, such as RAM, ROM, EEPROM or flash memory. Memory 94 may also include a removable memory portion that may be used to provide memory updates or increases in memory capacities. A removable memory may also allow sensitive patient data to be removed before programmer 14 is used by a different patient. Processor 92 may comprise any combination of one or more processors including one or more microprocessors, DSPs, ASICs, FPGAs, or other equivalent integrated or discrete logic circuitry. Accordingly, processor 92 may include any suitable structure, whether in hardware, software, firmware, or any combination thereof, to perform the functions ascribed herein to processor 92.

Wireless telemetry in programmer 14 may be accomplished by RF communication or proximal inductive interaction of external programmer 14 with IMD 16. This wireless communication is possible through the use of telemetry module 96. Accordingly, telemetry module 96 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 100 delivers operating power to the components of programmer 14. Power source 100 may include a battery and a power generation circuit to produce the operating power. In some examples, the battery may be rechargeable to allow extended operation. Recharging may be accomplished electrically coupling power source 100 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 100 may include circuitry to monitor power remaining within a battery. In this manner, user interface 98 may provide a current battery level indicator or low battery level indicator when the battery needs to be replaced or recharged. In some cases, power source 100 may be capable of estimating the remaining time of operation using the current battery.

Figure 9:
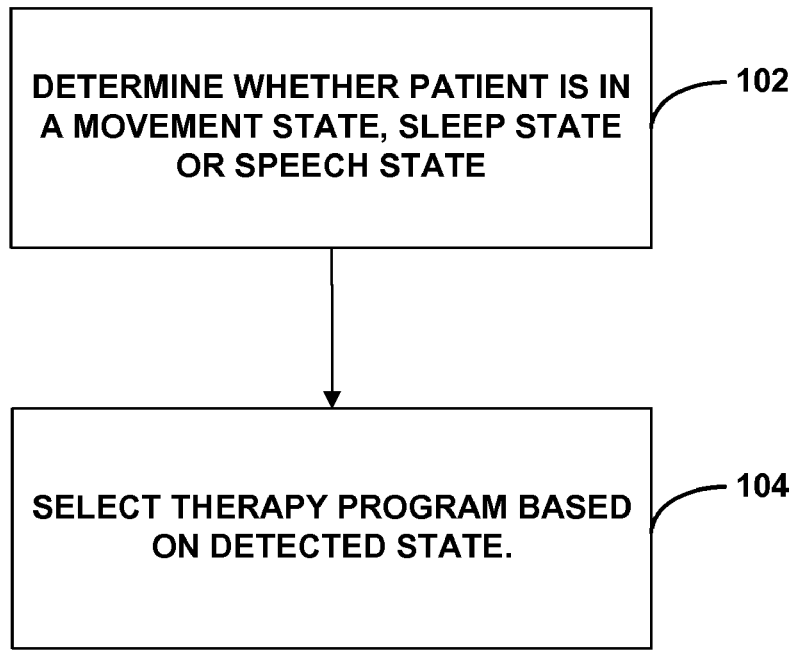
FIG. 9 illustrates a flow diagram of an example technique for controlling an implantable medical device (IMD) based on whether a patient is in a movement, sleep or speech state.

FIG. 9 illustrates a flow diagram of an example technique for controlling IMD 16 based on whether patient 12 is in a movement, sleep or speech state. Patient state module 59 (FIG. 3) determines whether patient 12 is in a movement, sleep or speech state (102), and processor 50 of IMD 16 (FIG. 3) selects a therapy program or a therapy program group from memory 52 based on the determined patient state (104). Processor 50 may select a therapy program from memory 52 by selecting a stored therapy program or by modifying a stored therapy program. In some examples, processor 50 selects a therapy program from memory 52 by selecting instructions that indicate modifications to a therapy program that is currently being implemented by IMD 16, modifications to the most recent therapy program if therapy is not currently being delivered by IMD 16 or modifications to a baseline therapy program, which is stored within memory 52.

Selecting therapy programs based on a current patient condition may be more beneficial than providing continuous or substantially continuous stimulation to patient 12 according to a therapy program that is not specifically determined to be efficacious of the patient's current state. In some cases, continuous or substantially continuous delivery of stimulation to the brain 28 may interfere with other brain functions, such as activity within subthalamic nucleus, as well as therapeutic deep brain stimulation in other basal ganglia sites. In addition providing stimulation intermittently or upon the sensing of movement by patient 12 may be a more efficient use of energy. Stimulation for managing a movement disorder may be delivered a higher frequency than stimulation for managing impaired speech or sleep. Accordingly, delivering higher frequency stimulation only when patient 12 is in a movement state may help conserve the power source within IMD 16, which may be an important consideration with an implanted medical device.

It has also been found that patient 12 may adapt to DBS provided by IMD 16 over time. That is, a certain level of electrical stimulation provided to brain 28 may be less effective over time. This phenomenon may be referred to as "adaptation." As a result, any beneficial effects to patient 12 from the DBS may decrease over time. While the electrical stimulation levels (e.g., amplitude of the electrical stimulation signal) may be increased to overcome such adaptation, the increase in stimulation levels may consume more power, and may eventually reach undesirable or harmful levels of stimulation.

When therapy parameter values are tailored to a specific patient state, rather than continuously or substantially continuously at a single therapy program (or a limited number of programs that are unrelated to the patient state), the rate at which patient adaptation to the therapy, whether electrical stimulation, drug delivery or otherwise, may decrease. Similarly, when one or more stimulation parameter values (e.g., amplitude, pulse width or frequency) are increased on demand, when a patient movement state is detected, both the rate at which patient 12 adapts to the stimulation therapy and the power consumed by IMD 16 may decrease as compared to continuous or substantially continuous stimulation at the elevated parameter values. Thus, therapy system 10 enables the therapy provided to patient 12 via IMD 16 to be more effective for a longer period of time as compared to systems in which therapy is delivered continuously or substantially continuously to patient 12.

Figure 10:
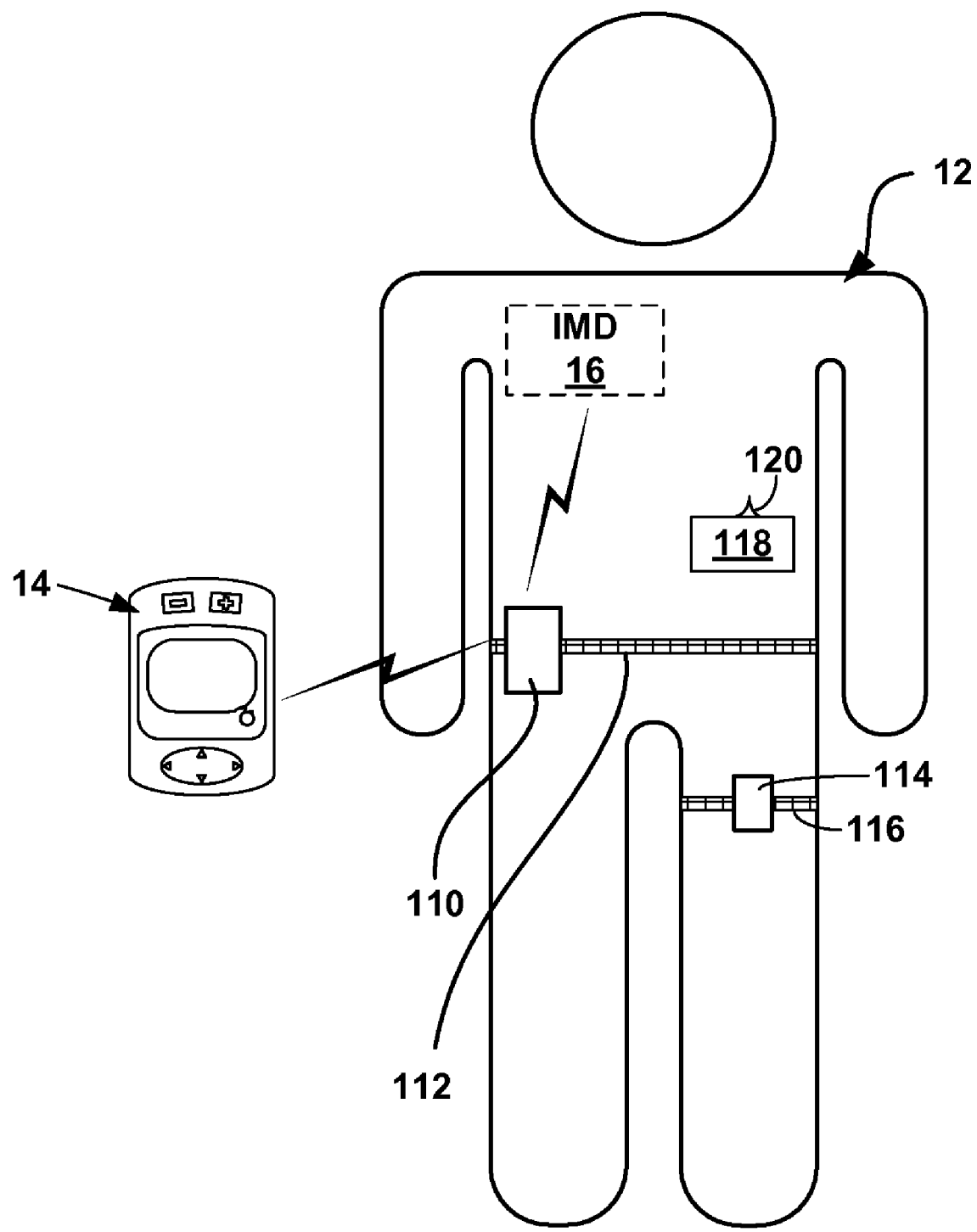
FIG. 10 is a schematic illustration of example motion sensors that may be used to determine a patient state.

Patient state module 59 of IMD 16 may determine whether patient 12 is in the movement, sleep or speech states in any suitable way. FIG. 10 is a conceptual illustration of an example in which patient state module 59 of IMD 16 determines whether patient 12 is in the movement, sleep or speech states based on input from motion sensor 110, which is coupled to patient via belt 112. Motion sensor 110 includes sensors that generate a signal indicative of patient motion, such as 2-axis or 3-axis accelerometer or a piezoelectric crystal. In one example, patient 12 may provide a volitional cue indicating a particular patient state by providing input via motion sensor 110. For example, patient 12 may tap motion sensor 110 in a different patterns to indicate patient 12 is in a respective one of a movement state, sleep state, and speech state. As another example, motion sensor 110 may determine patient 12 is in a movement state by detecting peripheral movement of a body part. Motion sensor 110 may then generate a signal indicative of the peripheral movement and a processor within motion sensor 110, programmer 14 or IMD 16 may determine the patient state associated with the signal. Thus, in some examples, motion sensor 110 and IMD 16 may communicate with each other using any suitable wireless communication technique, such as RF communication techniques.

If patient 12 has difficulty initiating movement, detecting movement of patient 12 via motion sensor 110 may also be used to determine whether patient 12 is in a movement state. For example, a lack of motion detected via motion sensor 110 combined with an indication of intent to move may be useful for determining when patient 12 is intending to move. As previously described, an indication of an intent to move may be provided via biosignals detected within the patient's brain, where the biosignals are generated by volitional patient input that are unrelated to the patient's symptoms or incidentally generated as a result of the patient's condition. The patient's attempt to move may be determined by detecting a small relative motion with motion sensor 110 (e.g., a slight movement of the foot in the case of the patient attempting to walk) combined with the presence of a biosignal indicating the patient's intent to move. In other cases, if patient has difficulty initiating movement, motion sensor 110 may detect a movement that is unrelated to the movement, sleep or speech states. For example, patient 12 may shrug his shoulders to indicate a speech state. The movements associated with the movement, sleep, and speech states may be personalized for patient 12, taking into consideration the patient's physical limitations.

Processor 50 of IMD 16 (FIG. 3) may monitor output from motion sensor 110. Signals generated by motion sensor 110 may be sent to processor 50 of IMD 16 (FIG. 3) via wireless signals. Processor 50 may process the signals to determine whether patient 12 is in a movement state, sleep state or speech state, and select a therapy program based on the determined patient state. As previously described, processor 50 may select a therapy program by selecting a stored therapy program or modifying a stored therapy program. In this way, input from motion sensor 110 may control stimulation generator 54 within IMD 16.

In some examples, processor 50 may determine whether the output from motion sensor 110 indicates a particular patient state by comparing a signal from motion sensor 110 with a stored template or threshold value (e.g., a threshold amplitude value). If patient 12 provides input by tapping motion sensor 110, motion sensor 110 may be an input mechanism that generates an electrical signal based on the patient tapping, such as a multiple or single axis accelerometer or a strain gauge that produces a detectable change in electrical resistance based on the extent of deformation of the strain gauge, although other input mechanisms may be possible. Thus, in some examples, motion sensor 110 is an accelerometer that generates an electrical signal that is based on one or more characteristics of the tapping, e.g., the number, frequency, and duration. Tapping refers to an action of pressing on motion sensor 110, e.g., with a finger, and subsequently releasing the finger from motion sensor 110. Motion sensor 110 may be capable of detecting movement on the order of approximately 1 mm to approximately 20 mm, although other orders of movement may also be detected.

Patient 12 may, for example, tap motion sensor 110 once to indicate a movement state, twice to indicate a sleep state, and three times to indicate a speech state. Other tapping associations, such as more complex patterns, may also be implemented. Processor 50 or a processor within sensor 110 may compare the electrical signal generated by motion sensor 110 in response to the tapping to a template or threshold value to determine a current patient state. Processor 50 may learn the signal template or threshold values that indicate each of the movement, sleep, and speech states during an initial learning or calibration mode during which the tapping is associated with particular patient states. A training mode may be important for patient 12 to easily and reliably provide input to indicate a current patient state.

In other examples, processor 50 of IMD 16 or a processor within sensor 110 may determine a patient's movement state by detecting a signal associated with the patient's movement, e.g. movement of the torso to indicate walking, or detecting a signal associated with a movement disorder symptom, such as a tremor or a movement associated with bradykinesia. Again, processor 50 may store a signal template or signal amplitude threshold value that indicates the relevant patient movement or movement disorder symptom during a trial stage.

A motion sensor may be coupled to patient 12 at any suitable location and via any suitable technique. For example, as shown in FIG. 10, accelerometer 114 may be coupled to a leg of patient 12 via band 116 or accelerometer 118 may be coupled to a torso of patient 12 via clip 120 that attaches to clothing. Alternatively, a motion sensor may be attached to patient 12 by any other suitable technique, such as via a wristband. In other examples, a motion sensor may be incorporated into IMD 16.

In another example, patient state module 59 may determine whether patient 12 is in a movement, speech or sleep state based on biosignals generated in brain 28 of patient 12. The biosignals may be generated based on volitional patient input, where the volitional patient input is generally unrelated to symptoms of the movement, speech or sleep state. For example, a detectable biosignal may be generated within the patient's brain 28 when patient 12 moves a limb (e.g., arm, finger or leg) in a predefined pattern or intends to move a limb. In other examples, the biosignal may be generated based on patient actions that are incidental to the movement, sleep, and speech states, but are still unrelated to symptoms of the movement, sleep, and speech states. For example, a detectable bioelectrical signal may be generated within the patient's brain 28 when patient 12 attempts to initiate movement, sleep or speech. Similarly, a detectable bioelectrical signal may be generated within the patient's brain 28 when patient 12 is moving, sleep or speaking.

The biosignal may include a bioelectrical signal, such as an EEG signal, an ECoG signal, a signal generated from measured field potentials within one or more regions of a patient's brain 28 and/or action potentials from single cells within the patient's 28 brain (referred to as "spikes"). Determining action potentials of single cells within brain 28 require resolution of bioelectrical signals to the cellular level and provides fidelity for fine movements, i.e., a bioelectrical signal indicative of fine movements (e.g., slight movement of a finger). While the remainder of the disclosure primarily refers to EEG signals, in other examples, patient state module 59 may be configured to determine whether patient 12 is in a movement, sleep or speech state based on other bioelectrical signals from within brain 28 of patient 12. Different biosignals may be associated with a respective one of the movement, sleep or speech states.

Figure 11:
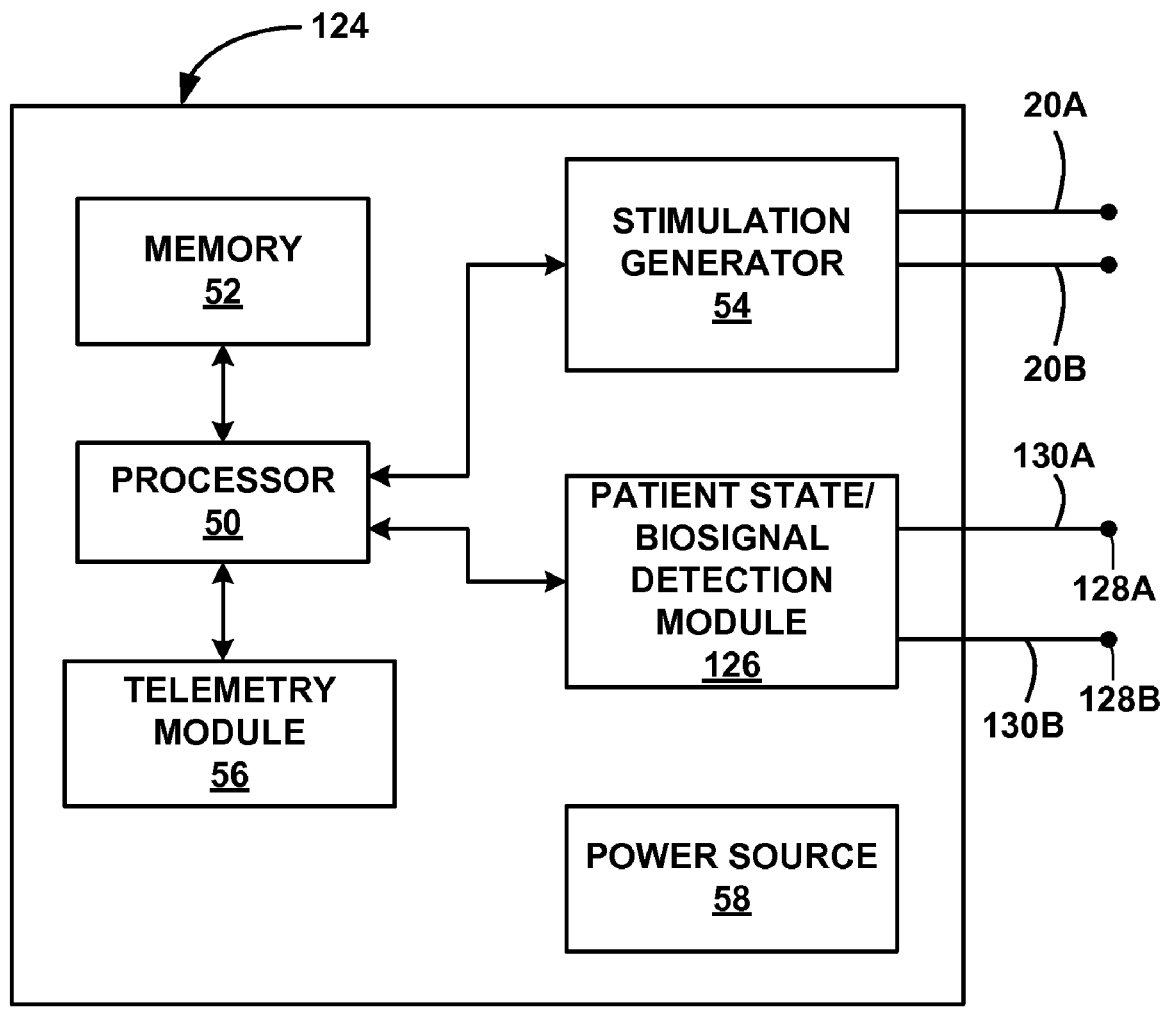
FIG. 11 is a block diagram of an example medical device that includes a biosignal detection module.

FIG. 11 is a conceptual block diagram of an example IMD 124, which includes a patient state/biosignal detection module 126 electrically coupled to electrodes 128A, 128B via respective leads 130A, 130B. In the example of IMD 124 shown in FIG. 11, biosignal detection module 126 comprises patient state module 59 (FIG. 3). In addition, IMD 124 includes processor 50, memory 52, stimulation generator 54, telemetry module 56, and power source 58, which are described above with respect to IMD 16 of FIG. 3. In other examples, biosignal detection module 126 and stimulation generator 54 may be coupled to at least one common lead and share at least one common electrode, which may be used to both sense biosignals and deliver stimulation.

While FIG. 11 is primarily described with respect to biosignals that result from volitional patient input, in other examples, biosignal detection module 126 may determine whether patient 12 is in a movement, sleep or speech state based on bioelectrical signals that are incidentally generated within brain 28 during or upon initiation of the patient's movement, sleep, and speech states, respectively. These bioelectrical signals may be determined during a trial phase. For example, patient 12 may initiate the movement, sleep, and speech states, and a clinician may determine the bioelectrical signal that results within brain 28. The bioelectrical signal may be recorded for comparison to sensed signals during later operation of the device to determine whether such signals indicate a particular patient state.

Processor 50 controls biosignal detection module 126. In the example shown in FIG. 11, biosignal detection module 126 is configured to detect or sense an EEG that indicates the electrical activity generated from the motor cortex of brain 28. The signals from the EEG are referred to as "EEG signals." Thus, biosignal detection module 126 detects one or more biosignals resulting from the volitional patient input by monitoring an EEG signal from within one or more regions of the patient's brain 28, and determines whether the biosignal can be detected from the EEG signal, e.g., whether the EEG signal includes the biosignal. While an EEG signal within the motor cortex is primarily referred to throughout the remainder of the application, in other examples, biosignal detection module 126 may detect a biosignal within other regions of brain 28.

The motor cortex of brain 28 is defined by regions within the cerebral cortex of brain 28 that are involved in the planning, control, and execution of voluntary motor functions, such as walking and lifting objects. Typically, different regions of the motor cortex control different muscles. For example, different "motor points" within the motor cortex may control the movement of the arms, trunk, and legs of patient. Accordingly, electrodes 128A, 128B may be positioned to sense the EEG signals of particular regions of the motor cortex, e.g., at a motor point that is associated with the movement of the arms, depending on the type of volitional patient inputs biosignal detection module 126 is configured to recognize as a patient state indicator. In other examples, electrodes 128A, 128B may be positioned proximate to other relevant regions of brain 28, such as, but not limited to, the sensory motor cortex, cerebellum or the basal ganglia. In addition, in some examples, more than one set of electrodes 128A, 128B may be placed at different regions of brain 28 if the different biosignals indicative of movement, sleep, and speech states are generated by different patient movements that are more easily detected at different regions of brain 28.

EEG is typically a measure of voltage differences between different parts of brain 28, and, accordingly, biosignal detection module 126 is electrically coupled to two or more electrodes 128A, 128B. Biosignal detection module 126 may then measure the voltage across at least two electrodes 128A, 128B. Although two electrodes 128A, 128B are shown in FIG. 11, in other examples, biosignal detection module 126 may be electrically coupled to any suitable number of electrodes. One or more of electrodes 128A, 128B may act as a reference electrode for determining the voltage difference of one or more regions of brain 28. Leads 130A, 130B coupling electrodes 128A, 128B to biosignal detection module 126 may, therefore, each include a separate, electrically isolated conductor for each electrode 26. Alternatively, electrodes 128A, 128B may be coupled to biosignal detection module 126 via separate conductors may be disposed within a common lead body. In some cases, a housing of IMD 124 may include an electrode that may be used to detect a bioelectrical signal within brain 28 of patient 12.

A clinician may locate the target site for electrodes 128A, 128B relative to patient's brain 28 via any suitable technique. The target site is typically selected to correspond to the region of brain 28 that generates an EEG signal indicative of the relevant motion, i.e., the relevant patient input. If, for example, if the clinician is primarily concerned with detecting a movement state of the patient's legs, the clinician may select a target site within brain 28 that corresponds to the region within the motor cortex associated with leg movement. If the clinician is concerned with detecting movement of the patient's finger in a particular pattern as an indicator of the speech state, the clinician may select a target site on the motor cortex that generates a detectable EEG signal in response to the patient's finger movement.

If electrodes 128A, 128B are used to detect movement of specific limbs (e.g., fingers, arms or legs) of patient 12, the clinician may locate the particular location for detecting movement of the specific limb via any suitable technique. In one example, the clinician may also utilize an imaging device, such as magnetoencephalography (MEG), positron emission tomography (PET) or functional magnetic resonance imaging (fMRI) to identify the region of the motor cortex of brain 28 associated with movement of the specific limb. In another example, the clinician may map EEG signals from different parts of the motor cortex and associate the EEG signals with movement of the specific limb in order to identify the motor cortex region associated with the limb. For example, the clinician may position electrodes 128A, 128B over the region of the motor cortex that exhibited the greatest detectable change in EEG signal at the time patient 12 actually moved the limb.

In one example, the clinician may initially place electrodes 128A, 128B based on the general location of the target region (e.g., it is known that the motor cortex is a part of the cerebral cortex, which may be near the front of the patient's head) and adjust the location of electrodes 128A, 128B as necessary to capture the electrical signals from the target region. Electrodes 128A, 128B may be physically moved relative to brain 28 or leads 130A, 130B may include an array of electrodes such that the clinician may select different electrodes, thereby "moving" the target EEG sensing site. In another example, the clinician may rely on the "10-20" system, which provides guidelines for determining the relationship between a location of an electrode and the underlying area of the cerebral cortex. In some examples, electrodes 128A, 128B may be located on a cranial surface of patient 12, rather than implanted within patient 12.

In other examples, the clinician may detect electrical signals within brain 28 that are generated as a result of the patient's movement, sleep, and speech states, rather than being generated in response to volitional input that is merely indicative of the movement, sleep, and speech states. For example, the electrical signals may be processed to determine whether the signals indicate patient 12 is in a movement, sleep or speech state by comparing a voltage or amplitude of the electrical signals with a threshold value, comparing an amplitude waveform of the electrical signal in the time domain or frequency domain to a template signal, determining a change in the amplitude or frequency of the electrical signals over time, comparing a ratio of power in different frequency bands to a stored value, combinations thereof, and the like.

In such examples, electrodes 128A, 128B may be placed proximate to the relevant regions of brain 28 that generate detectable and distinctive electrical signals during the movement, sleep, and speech states. For example, electrodes 128A, 128B may be positioned to detect electrical signals within the thalamus in order to detect a biosignal indicative of the sleep state. In some examples, electrodes 128A, 128B may be positioned to detect electrical signals within the thalamus or basal ganglia (e.g., the subthalamic nucleus) in order to detect a biosignal indicative of the speech state. Again, the clinician may utilize an imaging device, such as MEG, PET or fMRI to identify regions of brain 28 that generate detectable electrical signals during the patient's movement, sleep, and speech states. Although two electrodes 128A, 128B are shown in FIG. 11, in other examples, biosignal detection module 126 may be coupled to a plurality of electrodes, which may be carried by the same lead or different leads.

In the example shown in FIG. 11, IMD 124 does not directly select a therapy program based upon symptoms of the patient's condition or disease. Rather, biosignal detection module 126 detects a biosignal indicative of volitional patient input, where the biosignal is nonsymptomatic, and processor 50 selects a therapy program based on the biosignal, which is indicative of a patient's movement, sleep or speech state, by loading a therapy program stored within memory 52 or by modifying a stored therapy program based on instructions associated with the biosignal. That is, the biosignal is unrelated to a condition of the patient's disease. In the case of detecting volitional patient input, the biosignal does not result from an incidental electrical signal within the patient's brain 28 that patient 12 did not voluntarily or intentionally generate, such as a brain signal that results as a symptom of the patient's condition, which patient 12 cannot control. Rather, biosignal detection module 126 detects an intentionally generated biosignal, which may be generated based on patient input that is unrelated to the movement, sleep or speech states, or may be generated when patient 12 attempts to enter or is in the movement, sleep or speech states. For example, the biosignal may be a bioelectrical brain signal that indicates patient 12 intends to move, sleep or speech. As another example, the biosignal may be a bioelectrical brain signal that indicates patient 12 undertook some intentional action to indicate that he is entering a particular state.

The detection of a biosignal that results from volitional patient input differs from involuntary neuronal activity that may be caused by the patient's condition (e.g., a tremor or a seizure). In some examples, IMD 124 may detect symptomatic physiological changes of patient 12 (e.g., in brain 28) and adjust therapy accordingly in order to increase therapy efficacy. However, these symptomatic changes in brain 28 are not the biosignals detected by biosignal detection module 126. Instead, biosignal detection module 126 detects a particular biosignal within the patient's brain 28 that results from a volitional input, thereby allowing patient 12 to control one or more aspects of therapy by voluntarily causing a detectable physiological change within brain 28.

While certain symptoms of a patient's movement disorder may generate detectable changes in a monitored EEG signal, the symptomatic EEG signal changes are not indicative of the movement, sleep or speech states, as the terms are used herein. Rather than monitoring the EEG signal for detecting a patient's symptom, biosignal detection module 126 may detect a volitional patient thought via a monitored EEG signal. The volitional patient thought may relate directly to an intention to move, sleep or speak, or indirectly to a patient action that is associated with the movement, sleep, and speech states. Biosignal detection module 126 detects an EEG signal that is generated in response to a volitional patient thought (e.g., an intention to move or actual movement), and biosignal detection module 126 does not control a therapy device based on an EEG signal that is generated because of a symptom of the patient's condition. Thus, the EEG signal in the present methods and systems are nonsymptomatic. Furthermore, the EEG signal that provides the feedback to control stimulation generator 54 results from a volitional patient movement or intention to move, rather than an incidental electrical signal within the patient's brain that the patient did not voluntarily or intentionally generate. Thus, biosignal detection module 126 detects an EEG signal that differs from involuntary neuronal activity that may be caused by the patient's condition (e.g., a tremor or a seizure).

Detection of a biosignal within the patient's brain 28 that results from a volitional patient input allows patient 12 to provide input indicating whether patient 12 is in a movement state, sleep state or speech state without the use of an external programmer 14 (FIG. 1). In this manner, therapy control may be based on brain signals, rather than interacting with a user interface of external programmer 14. Example therapies include electrical stimulation, drug delivery, an externally or internally generated sensory cue, and any combination thereof. In addition, the system may support a learning mode to determine the biosignal. For example, one learning mode correlates a monitored EEG signal with a volitional patient input. A characteristic of the EEG signal, such as amplitude, frequency, change in amplitude or frequency over time, an amplitude waveform in the time domain or the frequency domain, a ratio of the power levels of the EEG signal in two or more frequency domains, and so forth, may be extracted from the monitored EEG signal to generate the biosignal. In this way, the feedback for the closed loop therapy adjustment may be customized to a particular patient.

In general, biosignal detection module 126 is configured to monitor an EEG from within a region of brain 28 and processor 50 or a separate processor within biosignal detection module 126 analyzes the EEG signals to determine whether the EEG signals include the biosignal indicative of a volitional patient input, and to determine whether the biosignal indicates patient 12 is in a movement, sleep or speech state. That is, processor 50 or a processor within biosignal detection module 126 determines when the EEG signal indicates that patient 12 provided the volitional input because the volitional input produces a detectable change in the EEG signal, i.e., detects the biosignal. While the processing of the EEG signals from biosignal detection module 126 are primarily described with reference to processor 50, in other examples, biosignal detection module 126 may independently identify a biosignal from patient 12 and notify processor 50 when such biosignal has been produced, and, in some cases, provide a signal to processor 50 indicating the patient state associated with the biosignal.

The volitional input may include, for example, a volitional thought about initiating a particular movement by patient 12 or an actual movement by patient 12 that is unrelated to the patient's symptoms. In one example, patient 12 may open and close his eyes in a particular pattern to indicate that patient 12 is in a movement state, where the particular pattern includes a defined interval between each eye opening and closing. When patient 12 indicates the movement state, patient 12 may be requesting the therapy for the movement state, e.g., therapy to help patient 12 initiate movement. As another example, patient 12 may move a finger or another limb in a particular pattern in order to indicate the speech state. Again, when patient 12 indicates the speech state, patient 12 may be requesting therapy delivery to help patient 12 initiate speech.

The volitional patient input associated with each of the movement, speech, and sleep states may be customized for a particular patient 12. For example, if patient 12 has a movement disorder, the patient input may be selected such that patient 12 may provide the input despite an impairment in movement. If patient 12 has difficulty lifting his arm, for example, the volitional patient input that provides the biosignal associated with the movement, sleep, and speech states may avoid patient inputs that require patient 12 to lift his arm.

A plurality of biosignals are associated with a respective patient state, such that upon detection of a biosignal by biosignal detection module 126, biosignal detection module 126 transmits a signal to processor 50 of IMD 124 indicating the determined patient state. Alternatively, biosignal detection module 126 may send a raw digitized EEG signal to processor 50, which processes the EEG signal to determine a patient state. Processor 50 may select a therapy program for execution by selecting a stored therapy program from memory 52 or select instructions (stored in memory 52) to modify a stored therapy program, where the selected stored program or instructions are associated with the indicated patient state. Processor 50 may control stimulation generator 54 to generate and deliver stimulation therapy to patient 12 according to the selected therapy program. Automatic activation of stimulation generator 54 upon the detection of a biosignal indicative of volitional patient input may help provide patient 12 with better control and timing of IMD 124 by eliminating the need for patient 12, who may exhibit difficulty with movement, to initiate therapy delivery via IMD 124.

In some cases, patient 12 may provide volitional input that is indicative of two or more patient states within a relatively short time period, such as within five seconds or less. Thus, in some cases, processor 50 may select therapy programs from memory 52 for more than one of the movement, speech or sleep states, and control stimulation generator 54 (FIG. 11) to deliver therapy according to multiple therapy programs. For example, the stimulation therapy according to the multiple selected programs may be delivered simultaneously or on a time-interleaved basis, either in an overlapping or non-overlapping manner.

If processor 50 detects a biosignal, processor 50 may determine the patient state associated with the biosignal and generate a therapy adjustment indication. The therapy adjustment indication may be a value, flag, or signal that is generated to indicate patient 12 provided a volitional thought indicative of a patient state, and, accordingly, indicative of a desired therapy program. The value, flag or signal may be stored in memory 52 or transmitted to stimulation generator 54. As previously described, different therapy programs may be associated with different patient states because patient conditions associated with the different patient states may be more effectively managed by different therapy programs. For example, akinesia, which is a movement disorder (i.e., may occur during a movement state), may be more effectively managed by a different set of stimulation parameter values than difficulty with speech (i.e., a speech state). Thus, memory 52 stores different therapy programs and associates the therapy programs with respective patient states. The stored therapy programs may be selected by a clinician during a trial stage in which IMD 124 is trialed by patient 12.

Upon determining the patient state based on a biosignal detected by biosignal detection module 126, processor 50 may select a therapy program that is associated with the indicated patient state by selecting a stored program from memory 52 or selecting instructions from memory 52 that indicate modifications to at least one therapy parameter of a program 52. For example, processor 50 may reference a look-up table as shown in FIG. 5. Processor 50 may control stimulation generator 54 to deliver therapy to patient 12 in accordance with the selected therapy program. In this way, the biosignal from an EEG signal may be a control signal for adjusting therapy. In some examples, processor 50 may record the therapy adjustment indication in memory 52 for later retrieval and analysis by a clinician. For example, movement state indications may be recorded over time, e.g., in a loop recorder, and may be accompanied by the relevant EEG signal and a date stamp that indicates that date and time the movement state was detected.

Processor 50 may implement any suitable technique to determine whether an EEG signal includes a biosignal. In some examples, processor 50 compares the EEG signals from biosignal detection module 126 with previously determined biosignal thresholds or templates stored in memory 52 in order to determine whether the biosignal can be detected from the EEG signal, i.e., whether the particular sensed EEG signal includes the biosignal. If the biosignal is detected, processor 50 may determine the patient state associated with biosignal, e.g., by referencing a look-up table or another data structure that associates various biosignals with a respective one or more of the movement, sleep or speech states. In this manner, processor 50 may determine when to adjust therapy from the biosignals, and selects a therapy program tailored to the indicated patient state based on the biosignal. Examples of signal processing techniques are described below with reference to FIGS. 13A and 13B.

As various examples of signal processing techniques that processor 50 may employ to determine whether the EEG signal includes the biosignal, processor 50 may compare a voltage or current amplitude of the EEG signal with a threshold value, correlate an amplitude waveform of the EEG signal in the time domain or frequency domain with a template signal, or combinations thereof. For example, the instantaneous or average amplitude of the EEG signal from within the motor cortex over a period of time may be compared to an amplitude threshold. In one example, when the amplitude of the EEG signal from within the occipital cortex is greater than or equal to the threshold value, processor 50 may select a therapy program from memory 52 that is associated with a movement state of patient 12, and control stimulation generator 54 to deliver stimulation to patient 12 according to the selected therapy program.

As another example, a slope of the amplitude of the EEG signal (or another bioelectrical brain signal) over time or timing between inflection points or other critical points in the pattern of the amplitude of the EEG signal over time may be compared to trend information. Different trends may be associated with a respective one of the movement, sleep or speech states. A correlation between the inflection points in the amplitude waveform of the EEG signal or other critical points and a template may indicate the EEG signal includes the biosignal indicative of patient input indicating the movement, sleep or speech states. Processor 50 may implement an algorithm that recognizes a trend of the EEG signals that characterize a biosignal. If the trend of the EEG signals matches or substantially matches the trend template for the movement state, processor 50 may control stimulation generator 54 to deliver stimulation to patient 12 according to a therapy program associated with the movement state. Similarly, if the trend of the EEG signals matches or substantially matches the trend template for the speech or sleep states, processor 50 may control stimulation generator 54 to deliver stimulation to patient 12 according to a therapy program associated with the respective speech or sleep states.

As another example, processor 50 may perform temporal correlation with one or more templates by sampling the waveform generated by the EEG signal with a sliding window and comparing the waveform with stored template waveforms that are indicative of the biosignal for a respective one of the movement, speech or sleep states. Processor 50 may compare an EEG signal with the template waveforms for the movement, speech or sleep states in any desired order. For example, processor 50 may compare the EEG signal with the template waveform indicative of the movement state, followed by the template waveform indicative of the speech state, and so forth. In one example, processor 50 may perform a correlation analysis by moving a window along a digitized plot of the amplitude waveform of EEG signals at regular intervals, such as between about one millisecond to about ten millisecond intervals, to define a sample of the EEG signal. The sample window is slid along the plot until a correlation is detected between a waveform of a template stored within memory 52 and the waveform of the sample of the EEG signal defined by the window. By moving the window at regular time intervals, multiple sample periods are defined. The correlation may be detected by, for example, matching multiple points between a template waveform and the waveform of the plot of the EEG signal over time, or by applying any suitable mathematical correlation algorithm between the sample in the sampling window and a corresponding set of samples stored in the template waveform.

Different frequency bands are associated with different activity in brain 28. One example of the frequency bands is shown in Table 1:

TABLE 1

| Frequency (f) Band Hertz (Hz) | Frequency Information |
|---|---|
| f < 5 Hz | δ (delta frequency band) |
| 5 Hz ≦ f ≦ 10 Hz | α (alpha frequency band) |
| 10 Hz ≦ f ≦ 30 Hz | β (beta frequency band) |
| 50 Hz ≦ f ≦ 100 Hz | γ (gamma frequency band) |
| 100 Hz ≦ f ≦ 200 Hz | high γ (high gamma frequency band) |

It is believed that some frequency band components of the EEG signal may be more revealing of particular activities than other frequency components. For example, the EEG signal activity within the alpha band may attenuate with eye opening or an increase or decrease in physical activity. Accordingly, if a volitional patient input includes opening and closing eyes in a particular pattern, processor 50 may analyze the EEG signal within the alpha frequency band. A higher frequency band, such as the beta or gamma bands, may also attenuate with an increase or decrease in physical activity. Accordingly, the type of volitional patient input may affect the frequency band of the EEG signal in which a biosignal associated with the patient input is detected. The relative power levels within the high gamma band (e.g., about 100 Hz to about 200 Hz) of an EEG signal, as well as other bioelectric signals, has been shown to be both an excellent biomarker for motion intent, as well as flexible to human control. For example, the desynchronization of the power level within the alpha band (e.g., mu waves, which are within the 10 Hz frequency band) and an increase in the power (e.g., by about a factor of four) in the high gamma waves (e.g., about 150 Hz) may indicate the patient is generating thoughts related to an intent to move. A human patient 12 may control activity within the high gamma band with volitional thoughts.

In the case of biosignals that are generated within brain 28 when patient 12 is in the movement, sleep, and speech states, rather than when patient 12 provides volitional input that results in the biosignal, different frequency bands may also be more revealing of the different patient states. For example, in some examples, the movement state may be detected by analyzing alpha band, gamma band or high gamma band components of an EEG signal. In some examples, the speech state may be detected by analyzing the delta band component (e.g., between about 3 Hz and about 5 Hz) of an EEG signal.

In some examples, different stages of the sleep state may be detected by analyzing different frequency band components of the EEG signal. For example, Stage I sleep may be detected by changes in the alpha frequency band (by an EEG signal component referred to as the posterior basic rhythm), Stage II sleep may be detected by changes in the alpha frequency band (e.g., in the 3 Hz to about 6 Hz range) or the beta frequency band (e.g., in the 12 Hz to about 14 Hz range), and Stages III and IV ("slow wave sleep") may be detectable in the delta frequency band component of an EEG signal. Stages I-IV of sleep are generally comprised of NREM sleep. An EEG signal in the REM sleep may be similar to the awake EEG, and, accordingly, REM sleep may be detected in the alpha, gamma or high gamma bands. The different sleep states may also be detected via an electrooculography (EOG) signal or electromyography (EMG) signal.

Different techniques for detecting sleep stages of patient 12 based on one or more frequency characteristics of a biosignal detected within brain 28 of patient 12 are described in U.S. patent application Ser. No. 12/238,105 to Wu et al., entitled, "SLEEP STAGE DETECTION" and filed on the same date as the present disclosure and U.S. Provisional Application No. 61/049,166 to Wu et al., entitled, "SLEEP STAGE DETECTION" and filed on Apr. 30, 2008. A frequency characteristic of the biosignal may include, for example, a power level (or energy) within one or more frequency bands of the biosignal, a ratio of the power level in two or more frequency bands, a correlation in change of power between two or more frequency bands, a pattern in the power level of one or more frequency bands over time, and the like.

The power level within the selected frequency band may be more revealing of the biosignal than a time domain plot of the EEG signal. Thus, in some examples, an analog tune amplifier may tune a monitored EEG signal to a particular frequency band in order to detect the power level (i.e., the signal strength) within a particular frequency band, such as a low frequency band (e.g., the alpha or delta frequency band from Table 1), the power level within a high frequency band (e.g., the beta or gamma frequency bands in Table 1) or both the power within the low and high frequency bands. The biosignal indicative of a volitional patient input may be the strength (i.e., a power level) of the EEG signal within the tuned frequency band, a pattern in the strength of the EEG signal over time, a ratio of power levels within two or more frequency bands, the pattern in the power level within two or more frequency bands (e.g., an increase in power level within the alpha and correlated with a decrease in a power level within the gamma band or high gamma band) or other characteristics of one or more frequency components of the EEG signal. The power level of the EEG signal within the tuned frequency band, the pattern of the power level over time, the ratio of power levels or another frequency characteristic based on one or more frequency bands may be compared to a stored value in order to determine whether the biosignal is detected.

A different volitional patient input may indicate a respective one of the movement, sleep or speech states. Accordingly, processor 50 may compare an EEG signal from biosignal detection module 126 with more than one stored value or template and determine which of the movement, sleep or speech states patient 12 indicated via volitional input based on the biosignal that is detected. In some examples, biosignal detection module 126 may monitor more than one frequency band in order to detect biosignals indicative of the movement, sleep or speech states.

Figure 15:
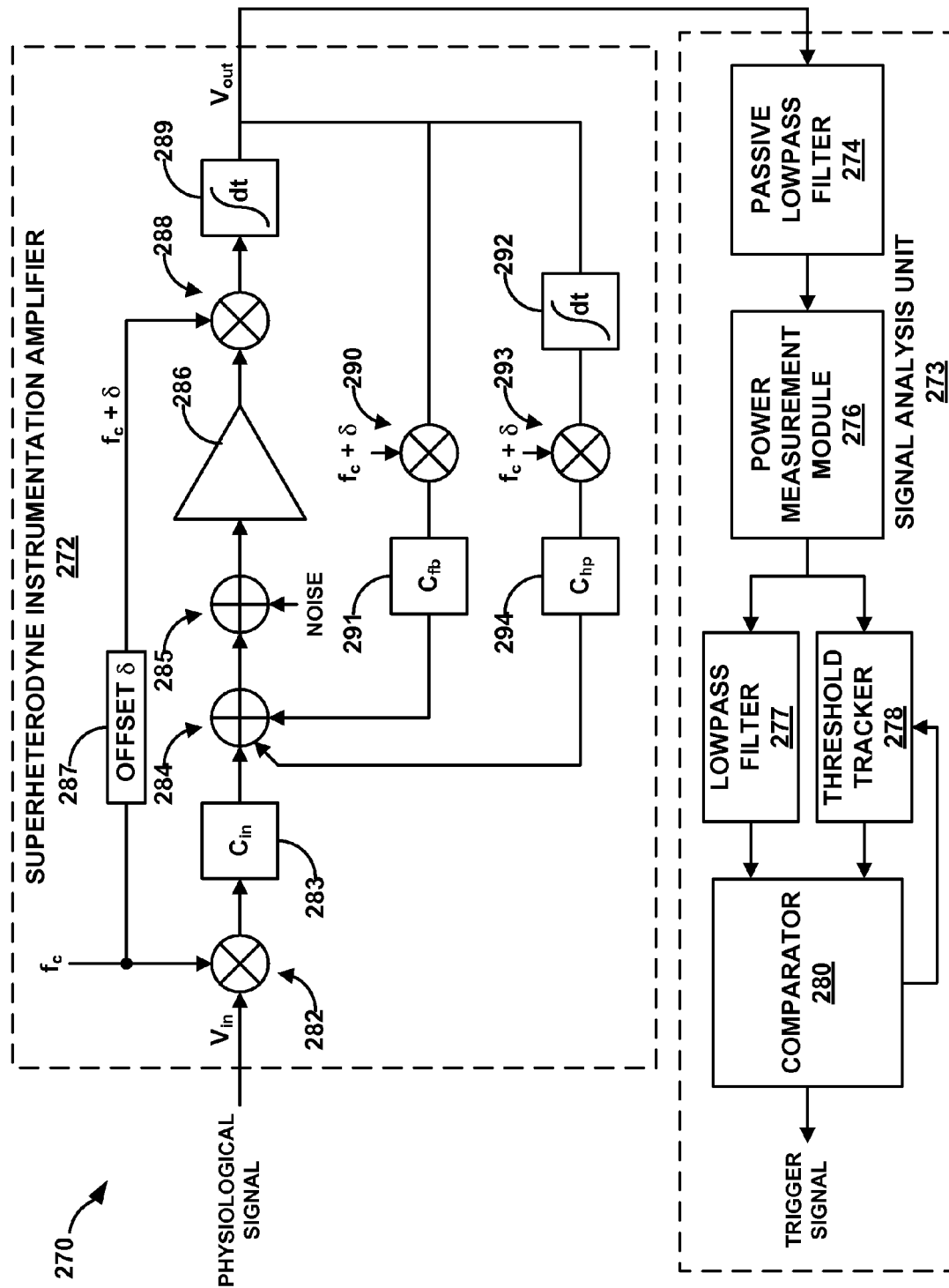
FIG. 15 is a block diagram illustrating an example frequency selective signal monitor that includes a chopper-stabilized superheterodyne amplifier and a signal analysis unit.

IMD 18 may include an analog sensing circuit with an amplifier. FIG. 15, described below, illustrates an example of an amplifier circuit that may be used to detect the biosignal, which may be included within biosignal detection module 126 or processor 50. The amplifier circuit shown in FIG. 15 uses limited power to monitor a frequency in which a desired biosignal is generated. If the amplifier is disposed within biosignal detection module 126, processor 50 may control biosignal detection module 126 to tune into the desired frequency band, which may be identified during a learning mode or based on clinician experience and information obtained during biosignal research.

In one example, an EEG signal detected by biosignal detection module 126 may be analyzed in the frequency domain to compare the power level of the EEG signal within one or more frequency bands to a threshold or to compare selected frequency components of an amplitude waveform of the EEG signal to corresponding frequency components of a template signal. The template signal may indicate, for example, a trend in the power level within one or more frequency bands that indicates patient 12 generated a volitional input that resulted in the biosignal indicative of a patient state. Specific examples of techniques for analyzing the frequency components of the EEG signal are described below with reference to FIG. 13B.

Processor 50 may employ an algorithm to suppress false positives, i.e., the selection of a therapy program for a particular patient state in response to a brain signal that is not the biosignal indicative of the patient input. For example, in addition to selecting a unique biosignal, processor 50 may implement an algorithm that identifies particular attributes of the biosignal (e.g., certain frequency characteristics of the biosignal) that are unique to the patient input for each of the movement, sleep and speech states. As another example, processor 50 may monitor the characteristics of the biosignal in more than one frequency band, and correlate a particular pattern in the power level or the power level of the brain signal within two or more frequency bands in order to determine whether the brain signal is indicative of the volitional patient input. As another example, the volitional patient input may include a pattern of volitional actions or thoughts that generate a specific pattern of brain signals or a brain signal including specific attributes that may be identified by the biosignal detection module. The specific attributes may include, for example, a pattern in the amplitude waveform of a bioelectrical brain signal, or a pattern or behavior of the frequency characteristics of the bioelectrical brain signal, and so forth.

Biosignal detection module 126 and methods and systems for detecting a biosignal indicative of volitional patient input is described in further detail in commonly-assigned U.S. patent application Ser. No. 11/974,931, entitled, "PATIENT DIRECTED THERAPY CONTROL" and filed on Oct. 16, 2007, which is incorporated herein by reference in its entirety. In other examples, biosignal detection module 126 may be separate from IMD 124, e.g., in a separate housing and carried external to patient 12 or implanted separately from IMD 124 within patient 12.

Techniques for detecting a movement state are further described in commonly-assigned U.S. patent application Ser. No. 12/237,799 to Molnar et al., entitled, "THERAPY CONTROL BASED ON A PATIENT MOVEMENT STATE,"

which was filed on the same date as the present disclosure, U.S. Provisional No. 60/999,096 to Molnar et al., entitled, "DEVICE CONTROL BASED ON PROSPECTIVE MOVEMENT" and filed on Oct. 16, 2007 and U.S. Provisional No. 60/999,097 to Denison et al., entitled, "RESPONSIVE THERAPY SYSTEM" and filed on Oct. 16, 2007. The entire contents of above-identified U.S. patent application Ser. No. 12/237,799 to Molnar et al., U.S. Provisional Application Nos. 60/999,096 and 60/999,097 are incorporated herein by reference.

Figure 12:
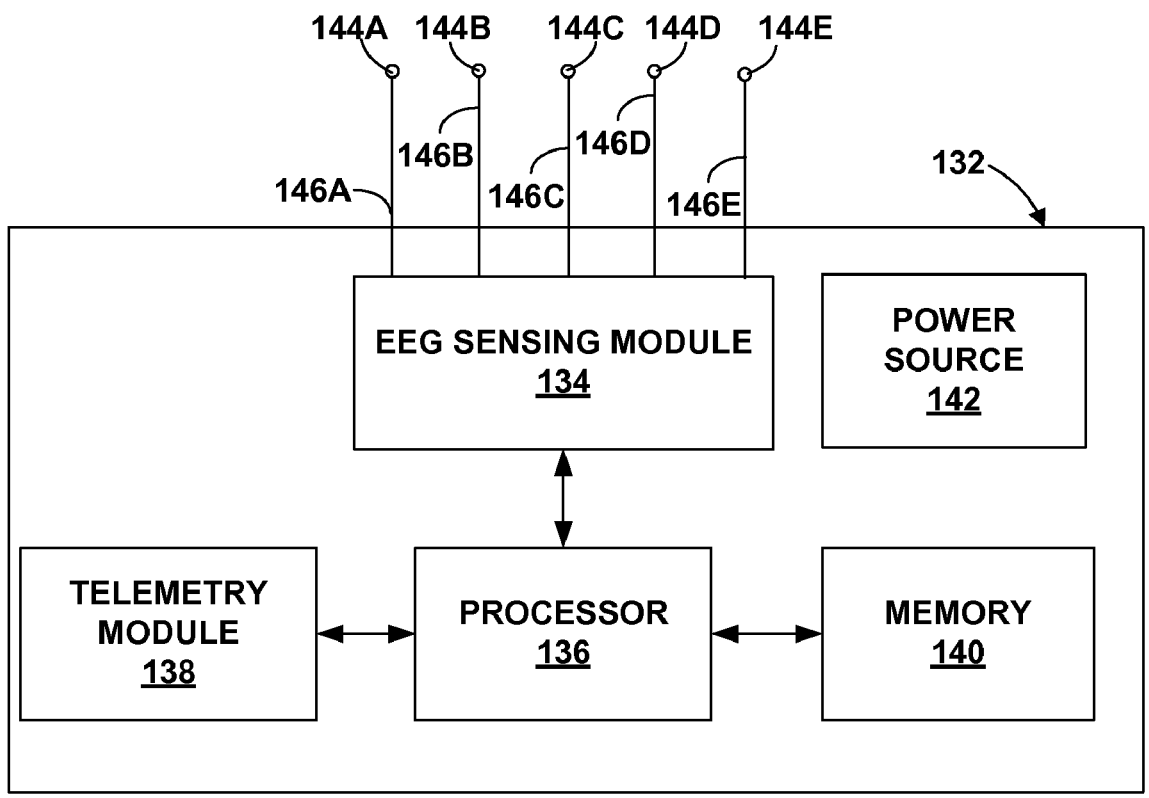
FIG. 12 is a functional block diagram illustrating components of an example biosignal detection module that is separate from a therapy delivery device.

FIG. 12 is a functional block diagram illustrating components of biosignal detection module 132 that is separate from a therapy delivery device, such as IMD 124 (FIG. 11). In some examples, biosignal detection module 132 may be separately implanted within patient 12 or may be an external device. Biosignal detection module 132 provides feedback to control a medical device, such as IMD 16 (FIG. 1) or external cue device 42 (FIG. 2). To deliver therapy based on a detected patient state. Biosignal detection module 132 includes EEG sensing module 134, processor 136, telemetry module 138, memory 140, and power source 142. Biosignal detection module 126 of IMD 124 (FIG. 11) may also include some components of biosignal detection module 132 shown in FIG. 12, such as EEG sensing module 134 and processor 136.

EEG sensing module 134, processor 136, as well as other components of biosignal detection module 132 that require power may be coupled to power source 142. Power source 142 may take the form of a rechargeable or non-rechargeable battery. EEG sensing module 134 monitors an EEG signal within brain 28 of patient 12 via electrodes 144A-144E. Electrodes 144A-144E are coupled to EEG sensing module 134 via leads 146A-146E, respectively. Two or more of leads 146A-146E may be bundled together (e.g., as separate conductors within a common lead body) or may include separate lead bodies.

Processor 136 may include any one or more of a microprocessor, a controller, a DSP, an ASIC, a FPGA, discrete logic circuitry or the like. As with the other processors described herein, the functions attributed to processor 136 may be implemented as software, firmware, hardware or any combinations thereof. Processor 136 controls telemetry module 138 to exchange information with programmer 14 (FIG. 1) and/or a therapy delivery device, such as IMD 16. Telemetry module 138 may include the circuitry necessary for communicating with programmer 14 or an implanted or external medical device. Examples of wireless communication techniques that telemetry module 138 may employ includes RF telemetry.

In some examples, biosignal detection module 132 may include separate telemetry modules for communicating with programmer 14 and a therapy delivery device. Telemetry module 138 may operate as a transceiver that receives telemetry signals from programmer 14 or a therapy delivery device, and transmits telemetry signals to the programmer 14 or therapy delivery device. For example, processor 136 may control the transmission of the EEG signals from EEG sensing module 134 to IMD 16. As another example, processor 136 may determine whether the EEG signal monitored by EEG sensing module 134 includes a biosignal, and, in some examples, whether the biosignal indicates the movement, sleep or speech states. Upon detecting the presence of the biosignal, processor 136 may transmit a control signal to the medical device via telemetry module 138, where the control signal indicates the type of therapy adjustment indicated by the biosignal.

In some examples, processor 136 stores monitored EEG signals in memory 140 for later analysis by a clinician. Memory 140 may include any volatile or non-volatile media, such as any combination of RAM, ROM, NVRAM, EEPROM, flash memory, and the like. Memory 140 may also store program instructions that, when executed by processor 136, cause EEG sensing module 134 to monitor the EEG signal of brain 28. Accordingly, computer-readable media storing instructions may be provided to cause processor 136 to provide functionality as described herein.

EEG sensing module 134 includes circuitry that measures the electrical activity of a particular region, e.g., motor cortex, within brain 28 via electrodes 144A-E. EEG sensing module 134 may acquire the EEG signal substantially continuously or at regular intervals, such as, but not limited to, at a frequency of about 1 Hz to about 100 Hz. EEG sensing module 134 includes circuitry for determining a voltage difference between two electrodes 144A-144E, which generally indicates the electrical activity within the particular region of brain 28. One of the electrodes 144A-144E may act as a reference electrode, and, if EEG sensing module 134 is implanted within patient 12, a housing of EEG sensing module 134 may include one or more electrodes that may be used to sense biosignals, such as EEG signals. An example circuit that EEG sensing module 134 may include to sense biosignals is shown and described below with reference to FIGS. 15-20. The EEG signals measured from via external electrodes 144A-144E may generate a voltage in a range of about 5 microvolts (μV) to about 100 μV.

The output of EEG sensing module 134 may be received by processor 136. Processor 136 may apply additional processing to the EEG signals, e.g., convert the output to digital values for processing and/or amplify the EEG signal. In some cases, a gain of about 90 decibels (dB) is desirable to amplify the EEG signals. In some examples, EEG sensing module 134 or processor 136 may filter the signal from electrodes 144A-144E in order to remove undesirable artifacts from the signal, such as noise from electrocardiogram signals, EMG signals, and EOG signals generated within the body of patient 12.

Processor 136 may determine whether the EEG signal from EEG sensing module 134 includes a biosignal indicative of a volitional patient input and whether the biosignal is indicative of the movement, sleep or speech states via any suitable technique, such as the techniques described above with respect to processor 50 of IMD 124 (FIG. 11). If processor 136 detects a biosignal from the EEG signal, processor 136 may determine whether the biosignal indicates a movement, sleep or speech state and generate a patient state indication. The patient state indication may be a value, flag, or signal that indicates patient 12 provided a volitional thought indicative of a current patient state or that indicates patient 12 is currently in a particular patient state.

Processor 136 may transmit the patient state indication to a therapy delivery device or programmer 14 via telemetry module 138, and the therapy delivery device or programmer 14 may select a therapy program according to the indicated patient state associated with the biosignal or therapy adjustment indication. In this way, the biosignal from an EEG signal may be a control signal for selecting a therapy program or otherwise adjusting therapy. Alternatively, memory 140 of biosignal detection module 132 may store a plurality of therapy programs or a symbol (e.g., an alphanumeric code) representative of therapy programs stored within the therapy delivery device, and processor 136 may select a therapy program or representative symbol based on the determined patient state and control the therapy delivery device to deliver therapy according to the therapy program or representative symbol.

In some examples, processor 136 may record the patient state indication in memory 140 for later retrieval and analysis by a clinician. For example, movement indications may be recorded over time, e.g., in a loop recorder, and may be accompanied by the relevant EEG signal. In other examples, rather than generating a therapy adjustment indication, processor 136 may merely control the transmission of the EEG signal from EEG sensing module 134 to a therapy delivery device or programmer 14. The therapy delivery device or programmer 14 may then determine whether the EEG signal includes the biosignal, and if so, whether the biosignal is indicative of a movement, sleep or speech state.

In other examples, a biosignal detection module may include a sensing module other than EEG sensing module, such as a sensing module configured to detect another brain signal, such as an ECoG signal, a signal generated from measured field potentials within one or more regions of brain 28 or action potentials from single cells within brain 28.

Figure 13A:
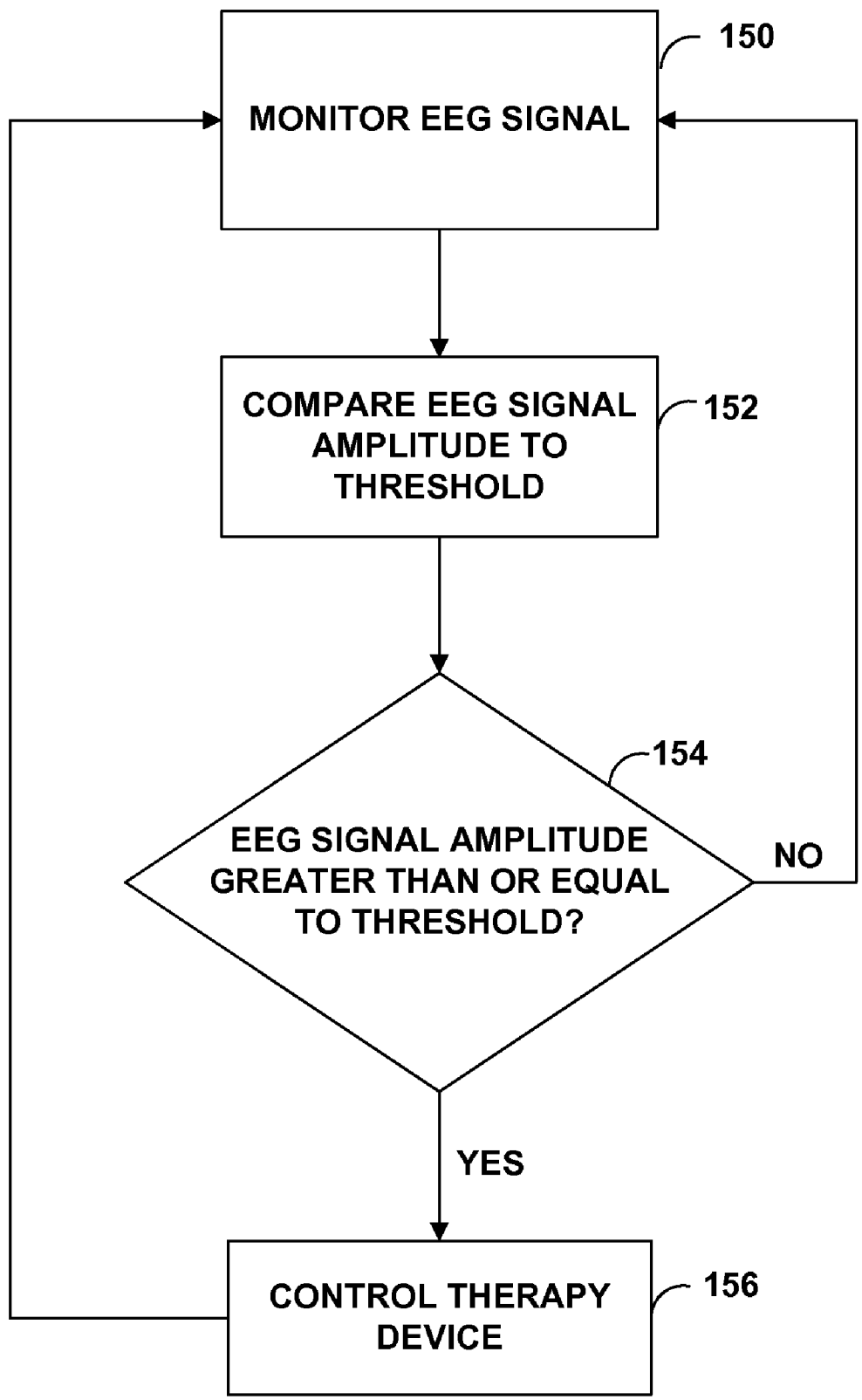
FIGS. 13A and 13B are flow diagrams illustrating example techniques that may be employed to control a therapy device based on a brain signal.

FIG. 13A is a flow diagram of an example of a technique for determining whether an EEG signal includes a biosignal indicative of a volitional patient thought indicative of a movement, sleep or speech state. While FIG. 13A is described with respect to biosignal detection module 132 of FIG. 12, in other examples, a biosignal detection module that is included in a common housing with a stimulation generator or another therapy module, such as biosignal detection module 126 of FIG. 11 may also perform any part of the technique shown in FIG. 13A-14. In addition, a processor of any device described herein may also perform any part of the technique shown in FIGS. 13A-14.

In the example shown in FIG. 13A, EEG sensing module 134 (FIG. 12) of biosignal detection module 132 may monitor the EEG signal within the motor cortex of brain 28 via electrodes 144A-144E substantially continuously or at regular intervals (150), such as at a measurement frequency of about 1 Hz to about 100 Hz. In other examples, EEG sensing module 134 may monitor the EEG signal within another part of brain 28, such as the sensory motor strip or occipital cortex. Processor 136 of biosignal detection module 132 may compare the amplitude of the EEG signal waveform to a stored threshold value (152). The relevant amplitude may be, for example, the instantaneous amplitude of an incoming EEG signal or an average amplitude of the EEG signal over period of time. In one example, the threshold value is determined during the trial phase that precedes implantation of a chronic therapy delivery device within patient 12.

In one example, if the monitored EEG signal waveform comprises an amplitude that is less than the threshold value (154), processor 134 does not generate any control signal to adjust therapy delivery. On the other hand, if the monitored EEG signal waveform comprises an amplitude that is greater than or equal to the threshold value (154), the EEG signal includes the biosignal indicative of the volitional patient input, and processor 134 may implement control of a therapy device (156). For example, processor 134 of biosignal detection module 132 may transmit a signal to IMD 16 to indicate that patient 12 is in the sleep state. Processor 50 (FIG. 3) of IMD 16 may then select a therapy program that is associated with the sleep state by selecting a stored therapy program from memory 52 (FIG. 3) or modifying a stored therapy program, and control stimulation generator 54 (FIG. 3) to deliver therapy to patient 12 according to the selected therapy program. In other examples, depending on the type of volitional patient input as well as the region of brain 28 in which the EEG signals are monitored, processor 134 may detect a biosignal if the amplitude of the EEG signal falls below a threshold value. A trial phase may be useful for determining the appropriate relationship between the threshold of the EEG signal and the threshold value.

Figure 13B:
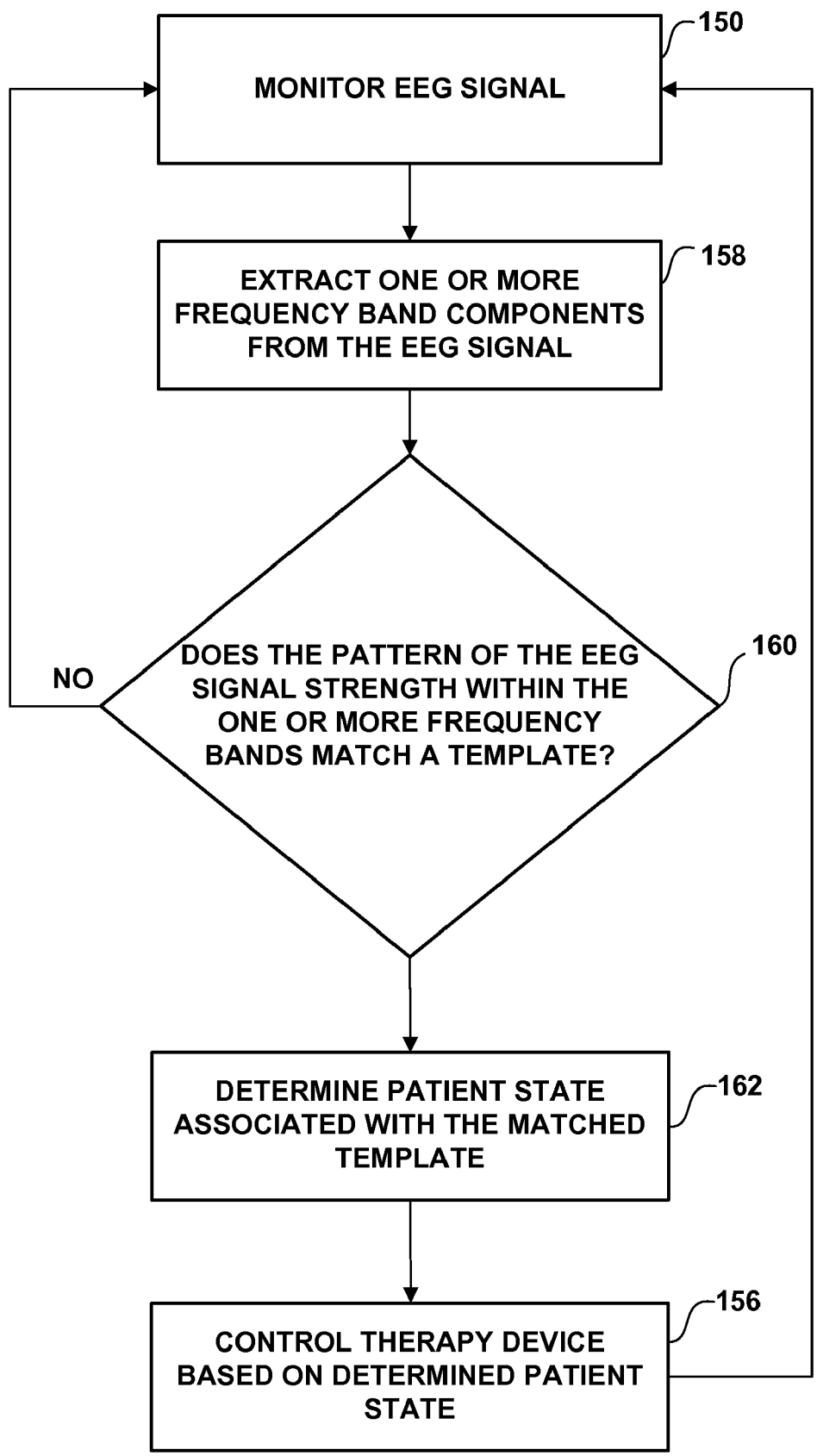

FIG. 13B is a flow diagram of another example technique for determining whether an EEG signal includes a biosignal indicative of a volitional patient input to indicate a patient state. EEG sensing module 134 (FIG. 12) of biosignal detection module 132 monitors the EEG signal within the motor cortex of brain 28 via electrodes 144A-144E continuously or at regular intervals (150), such as at a measurement frequency of about 1 Hz to about 100 Hz. In other examples, EEG sensing module 134 may monitor the EEG signal within another part of brain 28, such as the sensory motor strip or occipital cortex.

A signal processor within processor 136 of biosignal detection module 132 may extract one or more frequency band components of the monitored EEG signal (158) in order to determine whether a biosignal is detected. In the example shown in FIG. 13B, processor 136 compares the pattern in the EEG signal strength (i.e., the power level) within one or more frequency bands with one or more templates (160) in order to determine whether the biosignal is present and if so, whether the biosignal is indicative of the movement, sleep or speech states. Based on the determination of the patient state associated with the biosignal, processor 136 may generate a patient state indication to transmit to IMD 16 or another medical device, which may then select a therapy program for the determined patient state. In this way, processor 136 may use signal analysis techniques, such as correlation, to implement a therapy system for selecting a therapy program. In some examples, processor 136 of biosignal detection module 132 may select the therapy program and transmit the program or an indication of the program to IMD 12.

Different biosignals are indicative of a respective patient state. Thus, memory 140 of biosignal detection module 132 may store multiple pattern templates, where at least one pattern template is associated with a different patient state, and, in some examples, different stages of the patient state. Processor 136 may compare a pattern in the EEG signal strength within one or more frequency bands with multiple pattern templates in order to determine whether the biosignal is present and if so, whether the biosignal is indicative of the movement, sleep or speech states.

If the pattern of the EEG signal correlates well, i.e., matches, with a particular pattern template (160), processor 136 of biosignal detection module 132 may determine the patient state associated with the biosignal (162) and control the therapy delivered by a medical device based on the determined patient state (e.g., controls IMD 16 to select a therapy program) (156). In some examples, the template matching algorithm that is employed to determine whether the pattern in the EEG signal matches the template may not require a one hundred percent (100%) correlation match, but rather may only match some percentage of the pattern. For example, if the monitored EEG signal exhibits a pattern that matches about 75% or more of the template, the algorithm may determine that there is a substantial match between the pattern and the template, and the biosignal is detected. In other examples, processor 136 may compare a pattern in the amplitude waveform of the EEG signal (i.e., in the time domain) with a template. The pattern template for either the template matching techniques employed in either the frequency domain or the time domain may be generated in a trial phase.

In another example, patient state module 59 (FIG. 3) may determine whether patient 12 is in a movement, speech or sleep state based on bioelectrical signals detected within brain 28 of patient 12, where the bioelectrical signals are indicative of the movement, sleep, and speech states. In contrast to a biosignal, which is generated within brain 28 based on volitional patient input, a bioelectrical signal within brain 28 may be generated as a result of the patient's attempt to move, speak or sleep.

Biosignal detection module 126 may monitor a brain signal in multiple regions of brain 28 in order to detect brain signals that incidentally result when patient 12 is in the movement, sleep, and speech states. Thus, in some examples, biosignal detection module 126 may be coupled to more than two electrodes 128A and 128B, where the electrodes are positioned at different regions around brain 28. In one example, the electrodes may be placed at different regions of the somatosensory cortex and motor cortex of brain 28 that are associated with the patient's feeling and movement of various body parts, such as the feet, hands, fingers, eyes, and so forth, as is generally described as the cortical homunculus. A clinician may determine the relevant regions of brain 28 for detecting biosignals that are generated when patient 12 is in the movement, sleep, and speech states during a trial stage.

Figure 14:
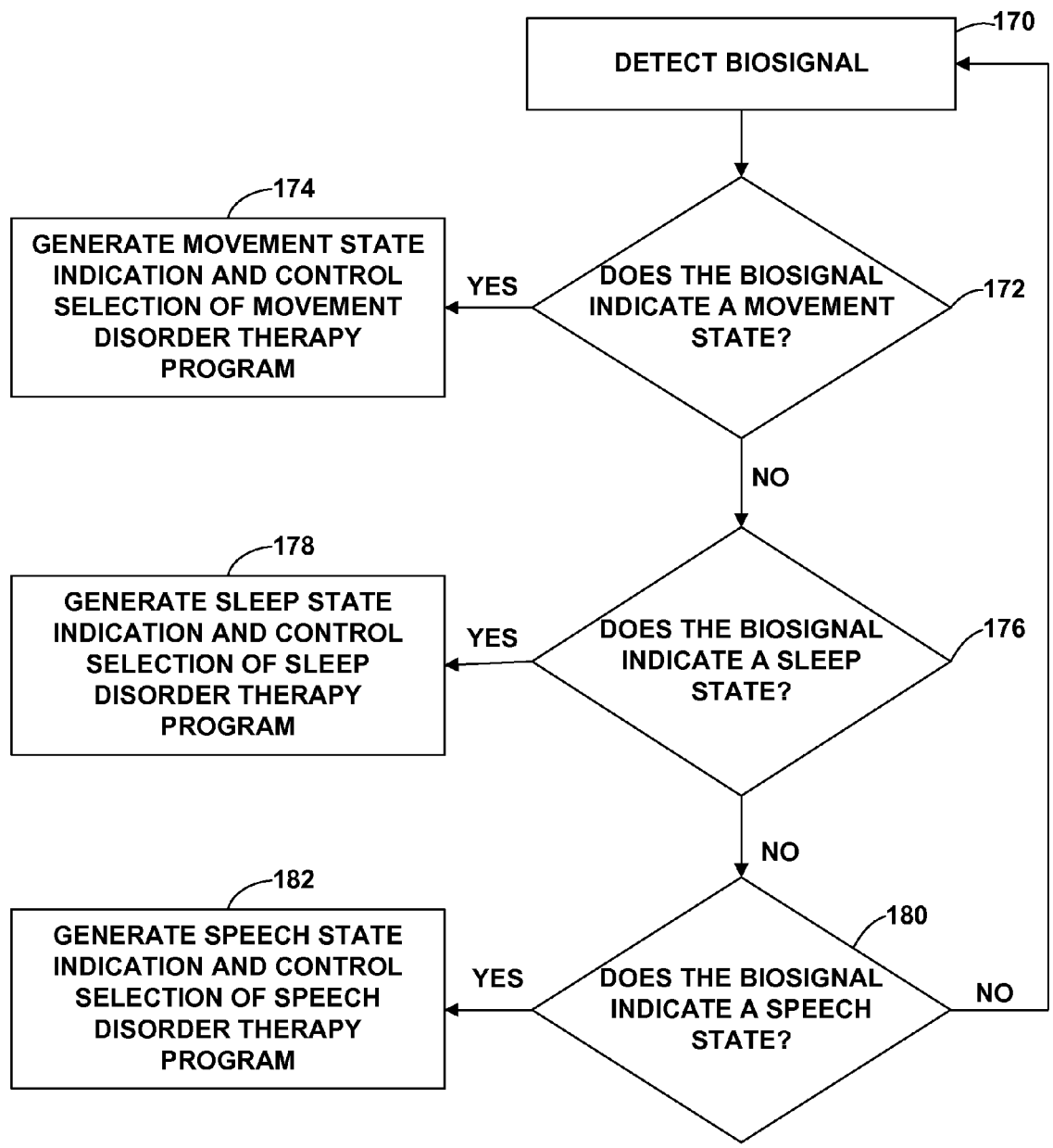
FIG. 14 is a flow diagram illustrating an example technique for selecting a therapy program based on a biosignal indicative of a patient state.

FIG. 14 is a flow diagram illustrating an example technique for selecting a therapy program based on a biosignal indicative of a patient state. In some examples, processor 50 of IMD 124 (FIG. 11) or processor 136 of biosignal detection module 132 (FIG. 12) may implement the technique shown in FIG. 14. For clarity of discussion, however, processor 136 is referred to throughout the description of FIG. 14. Processor 136 detects a biosignal within brain 28 of patient 12 (170), e.g., via EEG sensing module 134. The biosignal may be generated within brain 28 as a result of volitional patient actions, such as a volitional patient input by patient 12 to indicate patient 12 is in a movement, speech or sleep state. As another example, the volitional patient action that results in the biosignal monitored by processor 136 may be generated within brain 28 as a result of patient 12 generating thoughts directed toward an action directly related to the movement, sleep or speech states, such as thoughts relating to moving a leg to initiate a walking motion, attempting to speak or positioning himself in a recumbent position in order to sleep.

After processor 136 detects a biosignal (170), using any suitable technique, such as the techniques described above with respect to FIGS. 13A and 13B, processor 136 may determine whether the biosignal is associated with a movement state of patient (172). In some examples, processor 136 compares the biosignal with a template (e.g., a pattern in the amplitude of the biosignal or a power level of the biosignal in a particular frequency range) or compares a voltage or amplitude value of the biosignal (e.g., an EEG signal) to a stored value in order to determine whether the biosignal is associated with a movement state of patient (172). Other techniques are also contemplated.

If the detected biosignal is associated with a movement state, processor 136 may generate a movement state indication (174). The movement state indication may be, for example, a value, flag, or signal. In the example shown in FIG. 14, processor 136 controls the transmission of the movement state indication to a therapy device, such as IMD 16, via telemetry module 138 (FIG. 12). Upon receiving the movement state indication from biosignal detection module 132, processor 50 of IMD 16 may select a movement disorder therapy program by selecting a stored program from memory 52 or modifying a stored program from memory 52. The movement disorder therapy program may define stimulation parameter values or other therapy parameter values that provide efficacious therapy to patient 12 to manage one or more symptoms of a movement disorder, and, in some cases, one or more stages of movement (e.g., initiation of movement or gait improvement once movement is initiated). Alternatively, processor 136 of biosignal detection module 132 may select a therapy program by selecting or modifying a stored program from memory 140 of biosignal detection module 132 based on the movement state indication and transmit the stored or modified program or an indication of the program to IMD 16. In this way, the movement state indication controls the selection of a movement disorder therapy program from among stored therapy programs for a patient's movement, sleep, and speech states (174).

If the detected biosignal is not associated with a movement state (172), processor 136 of biosignal detection module 132 may determine whether the biosignal indicates a sleep state (176). In some examples, processor 136 compares the biosignal with a template or compares a voltage or amplitude value of the biosignal (e.g., an EEG signal) to a stored value in order to determine whether the biosignal is associated with a sleep state of patient (176). The template and voltage or amplitude value may differ from the template and voltage or amplitude value that indicates the movement state.

If the detected biosignal is associated with a sleep state, processor 136 may generate a sleep state indication (178). The sleep state indication may be, for example, a value, flag, or signal that differs from the movement state indication. In the example shown in FIG. 14, processor 136 may control the transmission of the sleep state indication to a therapy device, such as IMD 16, via telemetry module 138 (FIG. 12). Upon receiving the sleep state indication from biosignal detection module 132, processor 50 of IMD 16 may select a sleep disorder therapy program by selecting a stored program from memory 52 or modifying a stored program from memory 52. Alternatively, processor 136 of biosignal detection module 132 may select a therapy program by selecting or modifying a program stored within memory 140 of biosignal detection module 132 based on the sleep state indication and transmit the program or an indication of the program to IMD 16. In this way, the sleep state indication controls the selection of a sleep disorder therapy program from among stored therapy programs for a patient's movement, sleep, and speech states (178). The sleep disorder therapy program may define therapy parameter values that provide efficacious therapy for one or more symptoms of the patient's sleep disorder, and, in some examples, may be specific to a particular detected sleep stage of the sleep state.

If the detected biosignal is not associated with a sleep state (176), processor 136 of biosignal detection module 132 may determine whether the biosignal indicates a speech state (180). In some examples, processor 136 may compare the biosignal with a template or compare a voltage or amplitude value of the biosignal (e.g., an EEG signal) to a stored value in order to determine whether the biosignal is associated with a speech state of patient (180). The template and voltage or amplitude value may differ from the template and voltage or amplitude value that indicates the movement state and the sleep state. In other examples, processor 136 may analyze one or more frequency components of the biosignal to determine whether it indicates patient 12 is in a sleep state.

If the detected biosignal is associated with a speech state, processor 136 may generate a speech state indication (182). As with the movement state and sleep state indications, the speech state indication may be, for example, a value, flag, or signal that differs from the movement state and sleep state indications. In the example shown in FIG. 14, processor 136 may control the transmission of the speech state indication to a therapy device, such as IMD 16, via telemetry module 138 (FIG. 12). Upon receiving the speech state indication from biosignal detection module 132, processor 50 of IMD 16 may select a speech disorder therapy program by selecting a program from memory 52 or modifying a stored program from memory 52. Alternatively, processor 136 of biosignal detection module 132 may select a therapy program by selecting or modifying a program stored within memory 140 of biosignal detection module 132 based on the speech state indication and transmit the program or an indication of the program to IMD 16. In this way, the speech state indication controls the selection of a speech disorder therapy program from among stored therapy programs for a patient's movement, sleep, and speech states (182). The speech disorder therapy program may define therapy parameter values that provide efficacious therapy to patient 12 to manage one or more symptoms of a speech disorder, and, in some examples, may be specific to a detected speech stage (e.g., initiation of speech or maintenance of speech fluidity).

If the detected biosignal is not associated with a speech state (180), processor 136 of biosignal detection module 132 may conclude that the biosignal was a false detection, i.e., a false positive, and processor 136 may continue monitoring the EEG signal from EEG sensing module 134 to detect another biosignal (170). In the technique described in FIG. 14, processor 136 determines whether the biosignal is indicative of the movement state, sleep state, and speech state in a particular order. In other examples, however, processor 136 may determine whether the biosignal is indicative of the patient states in any suitable order, e.g., first detecting whether the biosignal is indicative of a speech state, followed by the sleep state and movement state.

Processor 136 may monitor the EEG signal from EEG sensing module 134 to detect a biosignal at regular intervals or substantially continuously in order to determine whether to change the therapy program with which IMD 16 delivers electrical stimulation therapy to patient 12. In another example of the technique shown in FIG. 14, rather than processor 136 of biosignal detection module 132 transmitting a movement state, sleep state or speech state indication to a therapy device, such as IMD 16, the therapy device may make the determination itself.

In addition to or instead of detecting biosignals to determine a patient's sleep state, the sleep state may be determined based on values of one or more sleep metrics that indicate a probability of patient 12 being asleep, such as using the techniques described in U.S. Patent Application Publication No. 2005/0209512, entitled, "DETECTING SLEEP" or U.S. Patent Application Publication No. 2005/0209511, entitled, "COLLECTING ACTIVITY AND SLEEP QUALITY INFORMATION VIA A MEDICAL DEVICE," which are both incorporated herein by reference in their entireties. The sleep metrics may be based on physiological parameters of patient 12, such as activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response. As described in U.S. Patent Application Publication No. 2005/0209512, a processor may apply a function or look-up table to the current value and/or variability of the physiological parameter to determine the sleep metric value and compare the sleep metric value to a threshold value to determine whether the patient is asleep. In some examples, the processor may compare the sleep metric value to each of a plurality of thresholds to determine the current sleep state of the patient, e.g., REM or one of the NREM sleep states.

In some examples, if stimulation generator 54 shifts the delivery of stimulation energy between two programs, processor 50 of IMD 16 may provide instructions that cause stimulation generator 54 to time-interleave stimulation energy between the electrode combinations of the two therapy programs, as described in commonly-assigned U.S. patent application Ser. No. 11/401,100 by Steven Goetz et al., entitled, "SHIFTING BETWEEN ELECTRODE COMBINATIONS IN ELECTRICAL STIMULATION DEVICE," and filed on Apr. 10, 2006, the entire content of which is incorporated herein by reference. In the time-interleave shifting example, the amplitudes of the electrode combinations of the first and second therapy program are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off.

FIG. 15 is a block diagram illustrating an exemplary frequency selective signal monitor 270 that includes a chopper-stabilized superheterodyne instrumentation amplifier 272 and a signal analysis unit 273. Signal monitor 270 may utilize a heterodyning, chopper-stabilized amplifier architecture to convert a selected frequency band of a physiological signal, such as a bioelectrical brain signal, to a baseband for analysis. The physiological signal may be analyzed in one or more selected frequency bands to trigger delivery of patient therapy and/or recording of diagnostic information. In some cases, signal monitor 270 may be utilized within a medical device to analyze a physiological signal to determine whether patient 12 is in a movement, sleep or speech state. For example, signal monitor 270 may be utilized within patient state module 59 included in IMD 16 implanted within patient 12 from FIG. 3 or within biosignal detection module 126 of IMD 124 (FIG. 11). In other cases, signal monitor 270 may be utilized within a separate sensor that communicates with a medical device. For example, signal monitor 270 may be utilized within an external or implanted biosignal detection module 132 in FIG. 12.

In general, frequency selective signal monitor 270 provides a physiological signal monitoring device comprising a physiological sensing element that receives a physiological signal, an instrumentation amplifier 272 comprising a modulator 282 that modulates the signal at a first frequency, an amplifier that amplifies the modulated signal, and a demodulator 288 that demodulates the amplified signal at a second frequency different from the first frequency. In the example of FIG. 15, amplifier 272 is a superheterodyne instrumentation amplifier. A signal analysis unit 273 analyzes a characteristic of the signal produced by amplifier 272 in the selected frequency band. The second frequency is selected such that the demodulator substantially centers a selected frequency band of the signal at a baseband.

The signal analysis unit 273 may comprise a lowpass filter 274 that filters the demodulated signal to extract the selected frequency band of the signal at the baseband. The second frequency may differ from the first frequency by an offset that is approximately equal to a center frequency of the selected frequency band. In one example, the physiological signal is an electrical signal, such as an EEG signal, ECoG signal, EMG signal, field potential, and the selected frequency band is one of an alpha, beta, gamma or high gamma frequency band of the electrical signal. The characteristic of the demodulated signal is power fluctuation of the signal in the selected frequency band. The signal analysis unit 273 may generate a signal triggering at least one of control of therapy to the patient or recording of diagnostic information when the power fluctuation exceeds a threshold.

In some examples, the selected frequency band comprises a first selected frequency band and the characteristic comprises a first power. The demodulator 288 demodulates the amplified signal at a third frequency different from the first and second frequencies. The third frequency may be selected such that the demodulator 288 substantially centers a second selected frequency band of the signal at a baseband. The signal analysis unit 273 analyzes a second power of the signal in the second selected frequency band, and calculates a power ratio between the first power and the second power. The signal analysis unit 273 generates a signal triggering at least one of control of therapy to the patient or recording of diagnostic information based on the power ratio.

In the example of FIG. 15, chopper-stabilized, superheterodyne amplifier 272 modulates the physiological signal with a first carrier frequency $f_c$, amplifies the modulated signal, and demodulates the amplified signal to baseband with a second frequency equivalent to the first frequency $f_c$ plus (or minus) an offset δ. Signal analysis unit 273 measures a characteristic of the demodulated signal in a selected frequency band.

The second frequency is different from the first frequency $f_c$ and is selected, via the offset δ, to position the demodulated signal in the selected frequency band at the baseband. In particular, the offset may be selected based on the selected frequency band. For example, the frequency band may be a frequency within the selected frequency band, such as a center frequency of the band.

If the selected frequency band is about 5 to about 15 Hz, for example, the offset δ may be the center frequency of this band, i.e., about 10 Hz. In some examples, the offset δ may be a frequency elsewhere in the selected frequency band. However, the center frequency generally will be preferred. The second frequency may be generated by shifting the first frequency by the offset amount. Alternatively, the second frequency may be generated independently of the first frequency such that the difference between the first and second frequencies is the offset.

In either case, the second frequency may be equivalent to the first frequency $f_c$ plus or minus the offset δ. If the first frequency $f_c$ is 4000 Hz, for example, and the selected frequency band is 5 to 15 Hz (the alpha band for EEG signals), the offset δ may be selected as the center frequency of that band, i.e., 10 Hz. In this case, the second frequency is the first frequency of 4000 Hz plus or minus 10 Hz. Using the superheterodyne structure, the signal is modulated at 4000 Hz by modulator 282, amplified by amplifier 286 and then demodulated by demodulator 288 at 3990 or 4010 Hz (the first frequency $f_c$ of 4000 Hz plus or minus the offset δ of 10 Hz) to position the 5 to 15 Hz band centered at 10 Hz at baseband, e.g., DC. In this manner the 5 to 15 Hz band can be directly downconverted such that it is substantially centered at DC.

As illustrated in FIG. 15, superheterodyne instrumentation amplifier 272 receives a physiological signal (e.g., $V_{in}$) from sensing elements positioned at a desired location within a patient or external to a patient to detect the physiological signal. For example, the physiological signal may comprise one of an EEG, EcoG, electromyogram EMG, ECG, pressure, temperature, impedance or motion signal. Again, an EEG signal will be described for purposes of illustration. Superheterodyne instrumentation amplifier 272 may be configured to receive the physiological signal ($V_{in}$) as either a differential or signal-ended input. Superheterodyne instrumentation amplifier 272 includes first modulator 282 for modulating the physiological signal from baseband at the carrier frequency ($f_c$). In the example of FIG. 15, an input capacitance ($C_{in}$) 283 couples the output of first modulator 282 to feedback adder 284. Feedback adder 284 will be described below in conjunction with the feedback paths.

Adder 285 represents the inclusion of a noise signal with the modulated signal. Adder 285 represents the addition of low frequency noise, but does not form an actual component of superheterodyne instrumentation amplifier 272. Adder 285 models the noise that comes into superheterodyne instrumentation amplifier 272 from non-ideal transistor characteristics. At adder 285, the original baseband components of the signal are located at the carrier frequency $f_c$. As an example, the baseband components of the signal may have a frequency within a range of approximately 0 to approximately 1000 Hz and the carrier frequency $f_c$ may be approximately 4 kHz to approximately 10 kHz. The noise signal enters the signal pathway, as represented by adder 285, to produce a noisy modulated signal. The noise signal may include 1/f noise, popcorn noise, offset, and any other external signals that may enter the signal pathway at low (baseband) frequency. At adder 285, however, the original baseband components of the signal have already been chopped to a higher frequency band, e.g., 4000 Hz, by first modulator 282. Thus, the low-frequency noise signal is segregated from the original baseband components of the signal.

Amplifier 286 receives the noisy modulated input signal represented by adder 285. Amplifier 286 amplifies the noisy modulated signal and outputs the amplified signal to a second modulator 288. Offset (δ) 287 may be tuned such that it is approximately equal to a frequency within the selected frequency band, and preferably the center frequency of the selected frequency band. The resulting modulation frequency ($f_c$±δ) used by demodulator 288 is then different from the first carrier frequency $f_c$ by the offset amount δ. In some cases, offset δ 287 may be manually tuned according to the selected frequency band by a physician, technician, or the patient. In other cases, the offset δ 287 may by dynamically tuned to the selected frequency band in accordance with stored frequency band values. For example, different frequency bands may be scanned by automatically or manually tuning the offset δ according to center frequencies of the desired bands.

As an example, when monitoring a patient's intent to move, the selected frequency band may be the alpha frequency band (5 Hz to 15 Hz). In this case, the offset δ may be approximately the center frequency of the alpha band, i.e., 10 Hz. As another example, when monitoring tremor, the selected frequency band may be the beta frequency band (15 Hz-35 Hz). In this case, the offset δ may be approximately the center frequency of the beta band, i.e., 25 Hz. As another example, when monitoring intent to move in the motor cortex, the selected frequency band may be the high gamma frequency band (150 Hz-200 Hz). In this case, the offset δ may be approximately the center frequency of the high gamma band, i.e., 175 Hz. As another illustration, the selected frequency band passed by filter 234 may be the gamma band (30 Hz-80 Hz), in which case the offset δ may be tuned to approximately the center frequency of the gamma band, i.e., 55 Hz.

Hence, the signal in the selected frequency band may be produced by selecting the offset (δ) 287 such that the carrier frequency plus or minus the offset frequency ($f_c$±δ) is equal to a frequency within the selected frequency band, such as the center frequency of the selected frequency band. In each case, as explained above, the offset may be selected to correspond to the desired band. For example, an offset of 5 Hz would place the alpha band at the baseband frequency, e.g., DC, upon downconversion by the demodulator. Similarly, an offset of 15 Hz would place the beta band at DC upon downconversion, and an offset of 30 Hz would place the gamma band at DC upon downconversion. In this manner, the pertinent frequency band is centered at the baseband. Then, passive low pass filtering may be applied to select the frequency band. In this manner, the superheterodyne architecture serves to position the desired frequency band at baseband as a function of the selected offset frequency used to produce the second frequency for demodulation. In general, in the example of FIG. 15, powered bandpass filtering is not required. Likewise, the selected frequency band can be obtained without the need for oversampling and digitization of the wideband signal.

With further reference to FIG. 15, second modulator 288 demodulates the amplified signal at the second frequency $f_c \pm \delta$, which is separated from the carrier frequency $f_c$ by the offset $\delta$. That is, second modulator 288 modulates the noise signal up to the $f_c \pm \delta$ frequency and demodulates the components of the signal in the selected frequency band directly to baseband. Integrator 289 operates on the demodulated signal to pass the components of the signal in the selected frequency band positioned at baseband and substantially eliminate the components of the noise signal at higher frequencies. In this manner, integrator 289 provides compensation and filtering to the amplified signal to produce an output signal ($V_{out}$). In other examples, compensation and filtering may be provided by other circuitry.

As shown in FIG. 15, superheterodyne instrumentation amplifier 272 may include two negative feedback paths to feedback adder 284 to reduce glitching in the output signal ($V_{out}$). In particular, the first feedback path includes a third modulator 290, which modulates the output signal at the carrier frequency plus or minus the offset $\delta$, and a feedback capacitance ($C_{fb}$) 291 that is selected to produce desired gain given the value of the input capacitance ($C_{in}$) 283. The first feedback path produces a feedback signal that is added to the original modulated signal at feedback adder 284 to produce attenuation and thereby generate gain at the output of amplifier 286.

The second feedback path may be optional, and may include an integrator 292, a fourth modulator 293, which modulates the output signal at the carrier frequency plus or minus the offset $\delta$, and high pass filter capacitance ($C_{hp}$) 294. Integrator 292 integrates the output signal and modulator 293 modulates the output of integrator 292 at the carrier frequency. High pass filter capacitance ($C_{hp}$) 294 is selected to substantially eliminate components of the signal that have a frequency below the corner frequency of the high pass filter. For example, the second feedback path may set a corner frequency of approximately equal to 2.5 Hz, 0.5 Hz, or 0.05 Hz. The second feedback path produces a feedback signal that is added to the original modulated signal at feedback adder 284 to increase input impedance at the output of amplifier 286.

As described above, chopper-stabilized, superheterodyne instrumentation amplifier 272 can be used to achieve direct downconversion of a selected frequency band centered at a frequency that is offset from baseband by an amount $\delta$. Again, if the alpha band is centered at 10 Hz, then the offset amount $\delta$ used to produce the demodulation frequency $f_c \pm \delta$ may be 10 Hz. As illustrated in FIG. 15, first modulator 282 is run at the carrier frequency ($f_c$), which is specified by the 1/f corner and other constraints, while second modulator 288 is run at the selected frequency band ($f_c \pm \delta$). Multiplication of the physiological signal by the carrier frequency convolves the signal in the frequency domain. The net effect of upmodulation is to place the signal at the carrier frequency ($f_c$). By then running second modulator 288 at a different frequency ($f_c \pm \delta$), the convolution of the signal sends the signal in the selected frequency band to baseband and $2\delta$. Integrator 289 may be provided to filter out the $2\delta$ component and passes the baseband component of the signal in the selected frequency band.

As illustrated in FIG. 15, signal analysis unit 273 receives the output signal from instrumentation amplifier. In the example of FIG. 15, signal analysis unit 273 includes a passive lowpass filter 274, a power measurement module 276, a lowpass filter 277, a threshold tracker 278 and a comparator 280. Passive lowpass filter 274 extracts the signal in the selected frequency band positioned at baseband. For example, lowpass filter 274 may be configured to reject frequencies above a desired frequency, thereby preserving the signal in the selected frequency band. Power measurement module 276 then measures power of the extracted signal. In some cases, power measurement module 276 may extract the net power in the desired band by full wave rectification. In other cases, power measurement module 276 may extract the net power in the desired band by a squaring power calculation, which may be provided by a squaring power circuit. As the signal has sine and cosine phases, summing of the squares yields a net of 1 and the total power. The measured power is then filtered by lowpass filter 277 and applied to comparator 280. Threshold tracker 278 tracks fluctuations in power measurements of the selected frequency band over a period of time in order to generate a baseline power threshold of the selected frequency band for the patient. Threshold tracker 278 applies the baseline power threshold to comparator 280 in response to receiving the measured power from power measurement module 276.

Comparator 280 compares the measured power from lowpass filter 277 with the baseline power threshold from threshold tracker 278. If the measured power is greater than the baseline power threshold, comparator 280 may output a trigger signal to a processor of a medical device to control therapy and/or recording of diagnostic information. If the measured power is equal to or less than the baseline power threshold, comparator 280 outputs a power tracking measurement to threshold tracker 278, as indicated by the line from comparator 280 to threshold tracker 278. Threshold tracker 278 may include a median filter that creates the baseline threshold level after filtering the power of the signal in the selected frequency band for several minutes. In this way, the measured power of the signal in the selected frequency band may be used by the threshold tracker 278 to update and generate the baseline power threshold of the selected frequency band for the patient. Hence, the baseline power threshold may be dynamically adjusted as the sensed signal changes over time. A signal above or below the baseline power threshold may signify an event that may support generation of a trigger signal.

In some cases, frequency selective signal monitor 270 may be limited to monitoring a single frequency band of the wide band physiological signal at any specific instant. Alternatively, frequency selective signal monitor 270 may be capable of efficiently hopping frequency bands in order to monitor the signal in a first frequency band, monitor the signal in a second frequency band, and then determine whether to trigger therapy and/or diagnostic recording based on some combination of the monitored signals. For example, different frequency bands may be monitored on an alternating basis to support signal analysis techniques that rely on comparison or processing of characteristics associated with multiple frequency bands.

Figure 16:
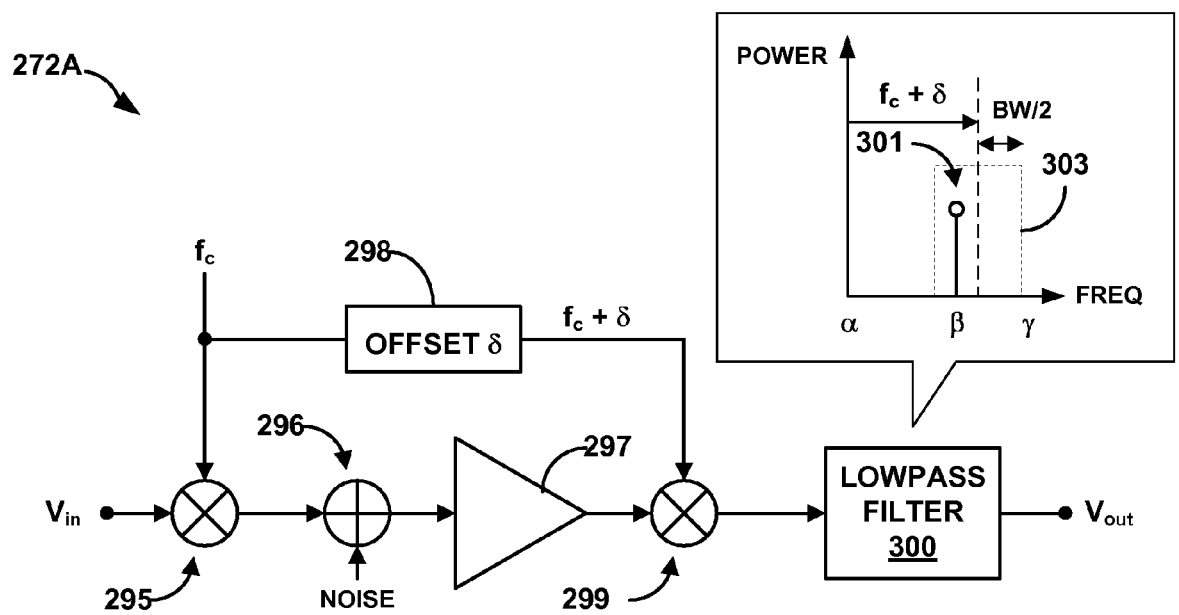
FIG. 16 is a block diagram illustrating a portion of an example chopper-stabilized superheterodyne amplifier for use within the frequency selective signal monitor from FIG. 15.

FIG. 16 is a block diagram illustrating a portion of an exemplary chopper-stabilized superheterodyne instrumentation amplifier 272A for use within frequency selective signal monitor 270 from FIG. 15. Superheterodyne instrumentation amplifier 272A illustrated in FIG. 16 may operate substantially similar to superheterodyne instrumentation amplifier 272 from FIG. 15. Superheterodyne instrumentation amplifier 272A includes a first modulator 295, an amplifier 297, a frequency offset 298, a second modulator 299, and a lowpass filter 300. In some examples, lowpass filter 300 may be an integrator, such as integrator 289 of FIG. 15. Adder 296 represents addition of noise to the chopped signal. However, adder 296 does not form an actual component of superheterodyne instrumentation amplifier 272A. Adder 296 models the noise that comes into superheterodyne instrumentation amplifier 272A from non-ideal transistor characteristics.

Superheterodyne instrumentation amplifier 272A receives a physiological signal ($V_{in}$) associated with a patient from sensing elements, such as electrodes, positioned within or external to the patient to detect the physiological signal. First modulator 295 modulates the signal from baseband at the carrier frequency ($f_c$). A noise signal is added to the modulated signal, as represented by adder 296. Amplifier 297 amplifies the noisy modulated signal. Frequency offset 298 is tuned such that the carrier frequency plus or minus frequency offset 298 ($f_c \pm \delta$) is equal to the selected frequency band. Hence, the offset $\delta$ may be selected to target a desired frequency band. Second modulator 299 modulates the noisy amplified signal at offset frequency 298 from the carrier frequency $f_c$. In this way, the amplified signal in the selected frequency band is demodulated directly to baseband and the noise signal is modulated to the selected frequency band.

Lowpass filter 300 may filter the majority of the modulated noise signal out of the demodulated signal and set the effective bandwidth of its passband around the center frequency of the selected frequency band. As illustrated in the detail associated with lowpass filter 300 in FIG. 16, a passband 303 of lowpass filter 300 may be positioned at a center frequency of the selected frequency band. In some cases, the offset $\delta$ may be equal to this center frequency. Lowpass filter 300 may then set the effective bandwidth (BW/2) of the passband around the center frequency such that the passband encompasses the entire selected frequency band. In this way, lowpass filter 300 passes a signal 301 positioned anywhere within the selected frequency band. For example, if the selected frequency band is 5 to 15 Hz, for example, the offset $\delta$ may be the center frequency of this band, i.e., 10 Hz, and the effective bandwidth may be half the full bandwidth of the selected frequency band, i.e., 5 Hz. In this case, lowpass filter 300 rejects or at least attenuates signals above 5 Hz, thereby limiting the passband signal to the alpha band, which is centered at 0 Hz as a result of the superheterodyne process. Hence, the center frequency of the selected frequency band can be specified with the offset $\delta$, and the bandwidth BW of the passband can be obtained independently with the lowpass filter 300, with BW/2 about each side of the center frequency.

Lowpass filter 300 then outputs a low-noise physiological signal ($V_{out}$). The low-noise physiological signal may then be input to signal analysis unit 273 from FIG. 15. As described above, signal analysis unit 273 may extract the signal in the selected frequency band positioned at baseband, measure power of the extracted signal, and compare the measured power to a baseline power threshold of the selected frequency band to determine whether to trigger patient therapy.

Figure 17A:
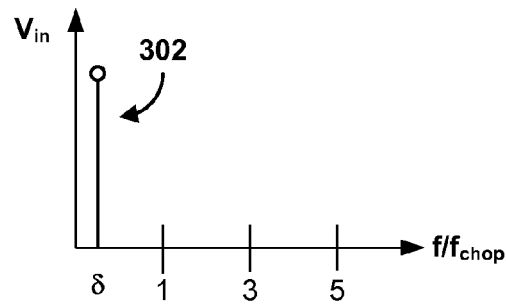
FIGS. 17A-17D are graphs illustrating the frequency components of a signal at various stages within the superheterodyne amplifier of FIG. 16.

FIGS. 17A-17D are graphs illustrating the frequency components of a signal at various stages within superheterodyne instrumentation amplifier 272A of FIG. 16. In particular, FIG. 17A illustrates the frequency components in a selected frequency band within the physiological signal received by frequency selective signal monitor 270. The frequency components of the physiological signal are represented by line 302 and located at offset $\delta$ from baseband in FIG. 17A.

Figure 17B:
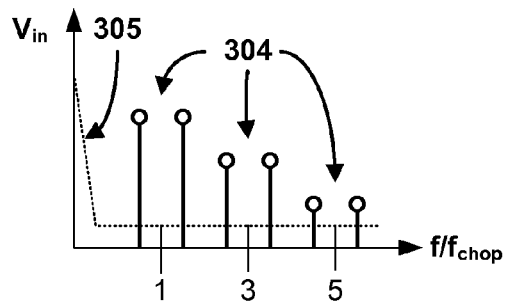

FIG. 17B illustrates the frequency components of the noisy modulated signal produced by modulator 295 and amplifier 297. In FIG. 17B, the original offset frequency components of the physiological signal have been up-modulated at carrier frequency $f_c$ and are represented by lines 304 at the odd harmonics. The frequency components of the noise signal added to the modulated signal are represented by dotted line 305. In FIG. 17B, the energy of the frequency components of the noise signal is located substantially at baseband and energy of the frequency components of the desired signal is located at the carrier frequency ($f_c$) plus and minus frequency offset ($\delta$) 298 and its odd harmonics.

Figure 17C:
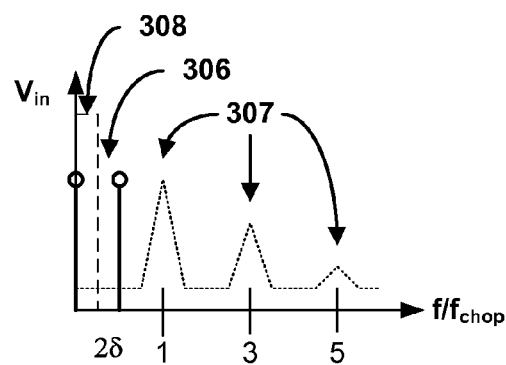

FIG. 17C illustrates the frequency components of the demodulated signal produced by demodulator 299. In particular, the frequency components of the demodulated signal are located at baseband and at twice the frequency offset ($2\delta$), represented by lines 306. The frequency components of the noise signal are modulated and represented by dotted line 307. The frequency components of the noise signal are located at the carrier frequency plus or minus the offset frequency ($\delta$) 298 and its odd harmonics in FIG. 17C. FIG. 17C also illustrates the effect of lowpass filter 300 that may be applied to the demodulated signal. The passband of lowpass filter 300 is represented by dashed line 308.

Figure 17D:
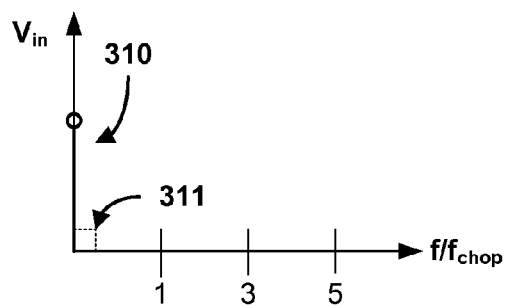

FIG. 17D is a graph that illustrates the frequency components of the output signal. In FIG. 17D, the frequency components of the output signal are represented by line 310 and the frequency components of the noise signal are represented by dotted line 311. FIG. 17D illustrates that lowpass filter 300 removes the frequency components of the demodulated signal located at twice the offset frequency ($2\delta$). In this way, lowpass filter 300 positions the frequency components of the signal at the desired frequency band within the physiological signal at baseband. In addition, lowpass filter 300 removes the frequency components from the noise signal that were located outside of the passband of lowpass filter 300 shown in FIG. 17C. The energy from the noise signal is substantially eliminated from the output signal, or at least substantially reduced relative to the original noise signal that otherwise would be introduced.

Figure 18:
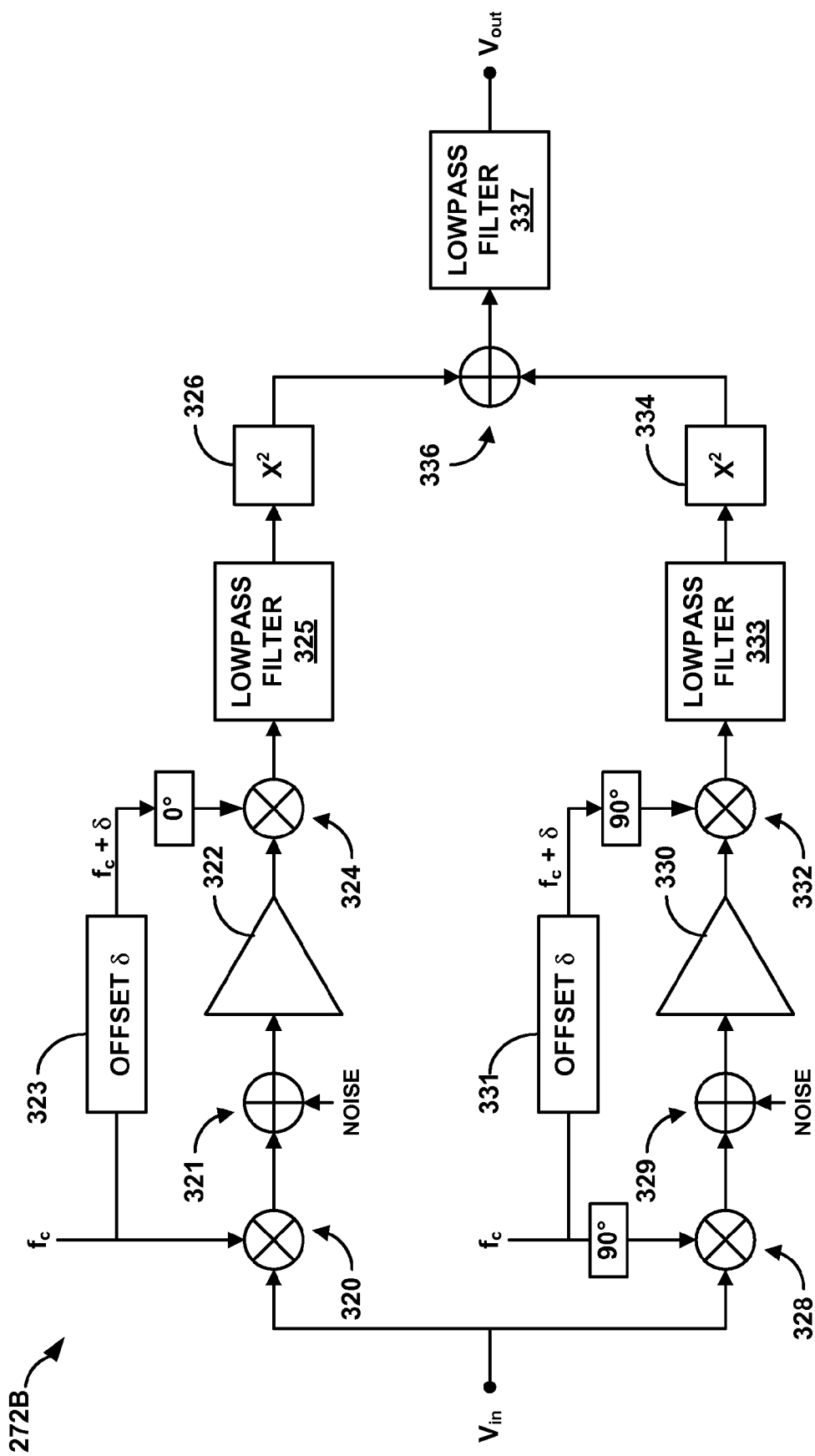
FIG. 18 is a block diagram illustrating a portion of an example chopper-stabilized superheterodyne amplifier with in-phase and quadrature signal paths for use within a frequency selective signal monitor.

FIG. 18 is a block diagram illustrating a portion of an exemplary chopper-stabilized superheterodyne instrumentation amplifier 272B with in-phase and quadrature signal paths for use within frequency selective signal monitor 270 from FIG. 15. The in-phase and quadrature signal paths substantially reduce phase sensitivity within superheterodyne instrumentation amplifier 272B. Because the signal obtained from the patient and the clocks used to produce the modulation frequencies are uncorrelated, the phase of the signal should be taken into account. To address the phasing issue, two parallel heterodyning amplifiers may be driven with in-phase (I) and quadrature (Q) clocks created with on-chip distribution circuits. Net power extraction then can be achieved with superposition of the in-phase and quadrature signals.

An analog implementation may use an on-chip self-cascoded Gilbert mixer to calculate the sum of squares. Alternatively, a digital approach may take advantage of the low bandwidth of the I and Q channels after lowpass filtering, and digitize at that point in the signal chain for digital power computation. Digital computation at the I/Q stage has advantages. For example, power extraction is more linear than a tan h function. In addition, digital computation simplifies offset calibration to suppress distortion, and preserves the phase information for cross-channel coherence analysis. With either technique, a sum of squares in the two channels can eliminate the phase sensitivity between the physiological signal and the modulation clock frequency. The power output signal can lowpass filtered to the order of 1 Hz to track the essential dynamics of a desired biomarker.

Superheterodyne instrumentation amplifier 272B illustrated in FIG. 18 may operate substantially similar to superheterodyne instrumentation amplifier 272 from FIG. 15. Superheterodyne instrumentation amplifier 272B includes an in-phase (I) signal path with a first modulator 320, an amplifier 322, an in-phase frequency offset (δ) 323, a second modulator 324, a lowpass filter 325, and a squaring unit 326. Adder 321 represents addition of noise. Adder 321 models the noise from non-ideal transistor characteristics. Superheterodyne instrumentation amplifier 272B includes a quadrature phase (Q) signal path with a third modulator 328, an adder 329, an amplifier 330, a quadrature frequency offset (δ) 331, a fourth modulator 332, a lowpass filter 333, and a squaring unit 334. Adder 329 represents addition of noise. Adder 329 models the noise from non-ideal transistor characteristics.

Superheterodyne instrumentation amplifier 272B receives a physiological signal ($V_{in}$) associated with a patient from one or more sensing elements. The in-phase (I) signal path modulates the signal from baseband at the carrier frequency ($f_c$), permits addition of a noise signal to the modulated signal, and amplifies the noisy modulated signal. In-phase frequency offset 323 may be tuned such that it is substantially equivalent to a center frequency of a selected frequency band. For the alpha band (5 to 15 Hz), for example, the offset 323 may be approximately 10 Hz. In this example, if the modulation carrier frequency $f_c$ applied by modulator 320 is 4000 Hz, then the demodulation frequency $f_c \pm \delta$ may be 3990 Hz or 4010 Hz.

Second modulator 324 modulates the noisy amplified signal at a frequency ($f_c \pm \delta$) offset from the carrier frequency $f_c$ by the offset amount δ. In this way, the amplified signal in the selected frequency band may be demodulated directly to baseband and the noise signal may be modulated up to the second frequency $f_c \pm \delta$. The selected frequency band of the physiological signal is then substantially centered at baseband, e.g., DC. For example, for the alpha band (e.g., about 5 to 15 Hz), for example, the center frequency of 10 Hz is centered at 0 Hz at baseband. Lowpass filter 325 filters the majority of the modulated noise signal out of the demodulated signal and outputs a low-noise physiological signal. The low-noise physiological signal may then be squared with squaring unit 326 and input to adder 336. In some cases, squaring unit 326 may comprise a self-cascoded Gilbert mixer. The output of squaring unit 126 represents the spectral power of the in-phase signal.

In a similar fashion, the quadrature (Q) signal path modulates the signal from baseband at the carrier frequency ($f_c$). However, the carrier frequency applied by modulator 328 in the Q signal path is about 90 degrees out of phase with the carrier frequency applied by modulator 320 in the I signal path. The Q signal path permits addition of a noise signal to the modulated signal, as represented by adder 329, and amplifies the noisy modulated signal via amplifier 330. Again, quadrature offset frequency (δ) 331 may be tuned such it is approximately equal to the center frequency of the selected frequency band. As a result, the demodulation frequency applied to demodulator 332 is ($f_c \pm \delta$). In the quadrature signal path, however, an additional phase shift of 90 degrees is added to the demodulation frequency for demodulator 332. Hence, the demodulation frequency for demodulator 332, like demodulator 324, is $f_c \pm \delta$. However, the demodulation frequency for demodulator 332 is phase shifted by 90 degrees relative to the demodulation frequency for demodulator 324 of the in-phase signal path.

Fourth modulator 332 modulates the noisy amplified signal at the quadrature frequency 331 from the carrier frequency. In this way, the amplified signal in the selected frequency band is demodulated directly to baseband and the noise signal is modulated at the demodulation frequency $f_c \pm \delta$. Lowpass filter 333 filters the majority of the modulated noise signal out of the demodulated signal and outputs a low-noise physiological signal. The low-noise physiological signal may then be squared and input to adder 336. Like squaring unit 326, squaring unit 334 may comprise a self-cascoded Gilbert mixer. The output of squaring unit 334 represents the spectral power of the quadrature signal.

Adder 336 combines the signals output from squaring unit 326 in the in-phase signal path and squaring unit 334 in the quadrature signal path. The output of adder 336 may be input to a lowpass filter 337 that generates a low-noise, phase-insensitive output signal ($V_{out}$). As described above, the signal may be input to signal analysis unit 273 from FIG. 15. As described above, signal analysis unit 273 may extract the signal in the selected frequency band positioned at baseband, measure power of the extracted signal, and compare the measured power to a baseline power threshold of the selected frequency band to determine whether to trigger patient therapy. Alternatively, signal analysis unit 273 may analyze other characteristics of the signal. The signal Vout may be applied to the signal analysis unit 273 as an analog signal. Alternatively, an analog-to-digital converter (ADC) may be provided to convert the signal Vout to a digital signal for application to signal analysis unit 273. Hence, signal analysis unit 273 may include one or more analog components, one or more digital components, or a combination of analog and digital components.

Figure 19:
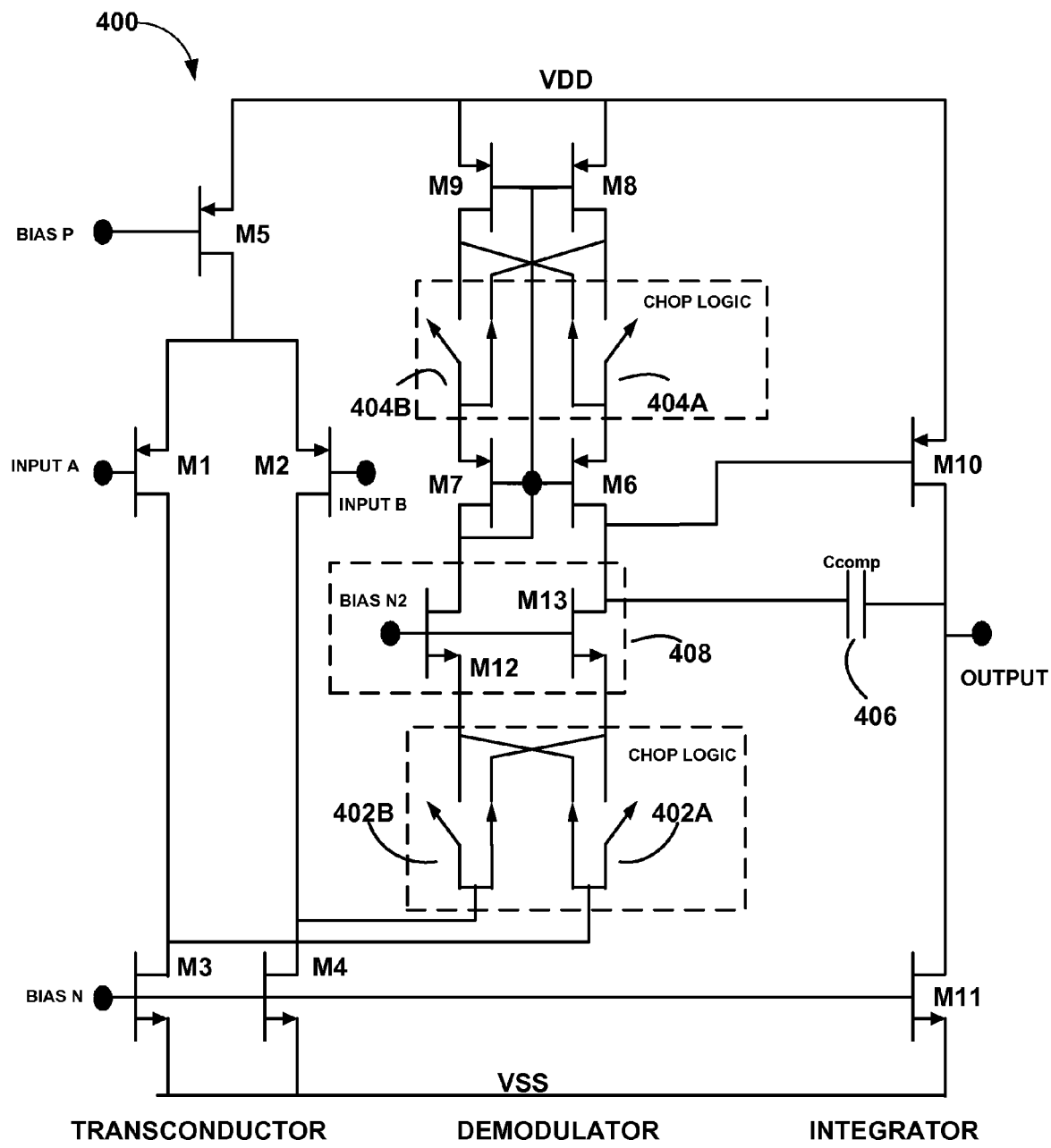
FIG. 19 is a circuit diagram illustrating an example chopper-stabilized mixer amplifier suitable for use within the frequency selective signal monitor of FIG. 15.

FIG. 19 is a circuit diagram illustrating an example mixer amplifier circuit 400 for use in superheterodyne instrumentation amplifier 272 of FIG. 15. For example, circuit 400 represents an example of amplifier 286, demodulator 288 and integrator 289 in FIG. 15. Although the example of FIG. 19 illustrates a differential input, circuit 400 may be constructed with a single-ended input. Accordingly, circuit 400 of FIG. 19 is provided for purposes of illustration, without limitation as to other examples. In FIG. 19, VDD and VSS indicate power and ground potentials, respectively.

Mixer amplifier circuit 400 amplifies a noisy modulated input signal to produce an amplified signal and demodulates the amplified signal. Mixer amplifier circuit 400 also substantially eliminates noise from the demodulated signal to generate the output signal. In the example of FIG. 19, mixer amplifier circuit 400 is a modified folded-cascode amplifier with switching at low impedance nodes. The modified folded-cascode architecture allows currents to be partitioned to maximize noise efficiency. In general, the folded cascode architecture is modified in FIG. 19 by adding two sets of switches. One set of switches is illustrated in FIG. 19 as switches 402A and 402B (collectively referred to as "switches 402") and the other set of switches includes switches 404A and 404B (collectively referred to as "switches 404").

Switches 402 are driven by chop logic to support the chopping of the amplified signal for demodulation at the chop frequency. In particular, switches 402 demodulate the amplified signal and modulate front-end offsets and 1/f noise. Switches 404 are embedded within a self-biased cascode mirror formed by transistors M6, M7, M8 and M9, and are driven by chop logic to up-modulate the low frequency errors from transistors M8 and M9. Low frequency errors in transistors M6 and M7 are attenuated by source degeneration from transistors M8 and M9. The output of mixer amplifier circuit 400 is at baseband, allowing an integrator formed by transistor M10 and capacitor 406 (Ccomp) to stabilize a feedback path (not shown in FIG. 19) between the output and input and filter modulated offsets.

In the example of FIG. 19, mixer amplifier circuit 400 has three main blocks: a transconductor, a demodulator, and an integrator. The core is similar to a folded cascode. In the transconductor section, transistor M5 is a current source for the differential pair of input transistors M1 and M2. In some examples, transistor M5 may pass approximately 800 nA, which is split between transistors M1 and M2, e.g., 400 nA each. Transistors M1 and M2 are the inputs to amplifier 286. Small voltage differences steer differential current into the drains of transistors M1 and M2 in a typical differential pair way. Transistors M3 and M4 serve as low side current sinks, and may each sink roughly 500 nA, which is a fixed, generally nonvarying current. Transistors M1, M2, M3, M4 and M5 together form a differential transconductor.

In this example, approximately 100 nA of current is pulled through each leg of the demodulator section. The AC current at the chop frequency from transistors M1 and M2 also flows through the legs of the demodulator. Switches 402 alternate the current back and forth between the legs of the demodulator to demodulate the measurement signal back to baseband, while the offsets from the transconductor are up-modulated to the chopper frequency. As discussed previously, transistors M6, M7, M8 and M9 form a self-biased cascode mirror, and make the signal single-ended before passing into the output integrator formed by transistor M10 and capacitor 406 (Ccomp). Switches 404 placed within the cascode (M6-M9) upmodulate the low frequency errors from transistors M8 and M9, while the low frequency errors of transistor M6 and transistor M7 are suppressed by the source degeneration they see from transistors M8 and M9. Source degeneration also keeps errors from Bias N2 transistors 408 suppressed. Bias N2 transistors M12 and M13 form a common gate amplifier that presents a low impedance to the chopper switching and passes the signal current to transistors M6 and M7 with immunity to the voltage on the drains.

The output DC signal current and the upmodulated error current pass to the integrator, which is formed by transistor M10, capacitor 406, and the bottom NFET current source transistor M11. Again, this integrator serves to both stabilize the feedback path and filter out the upmodulated error sources. The bias for transistor M10 may be approximately 100 nA, and is scaled compared to transistor M8. The bias for lowside NFET M11 may also be approximately 100 nA (sink). As a result, the integrator is balanced with no signal. If more current drive is desired, current in the integration tail can be increased appropriately using standard integrate circuit design techniques. Various transistors in the example of FIG. 19 may be field effect transistors (FETs), and more particularly CMOS transistors.

Figure 20:
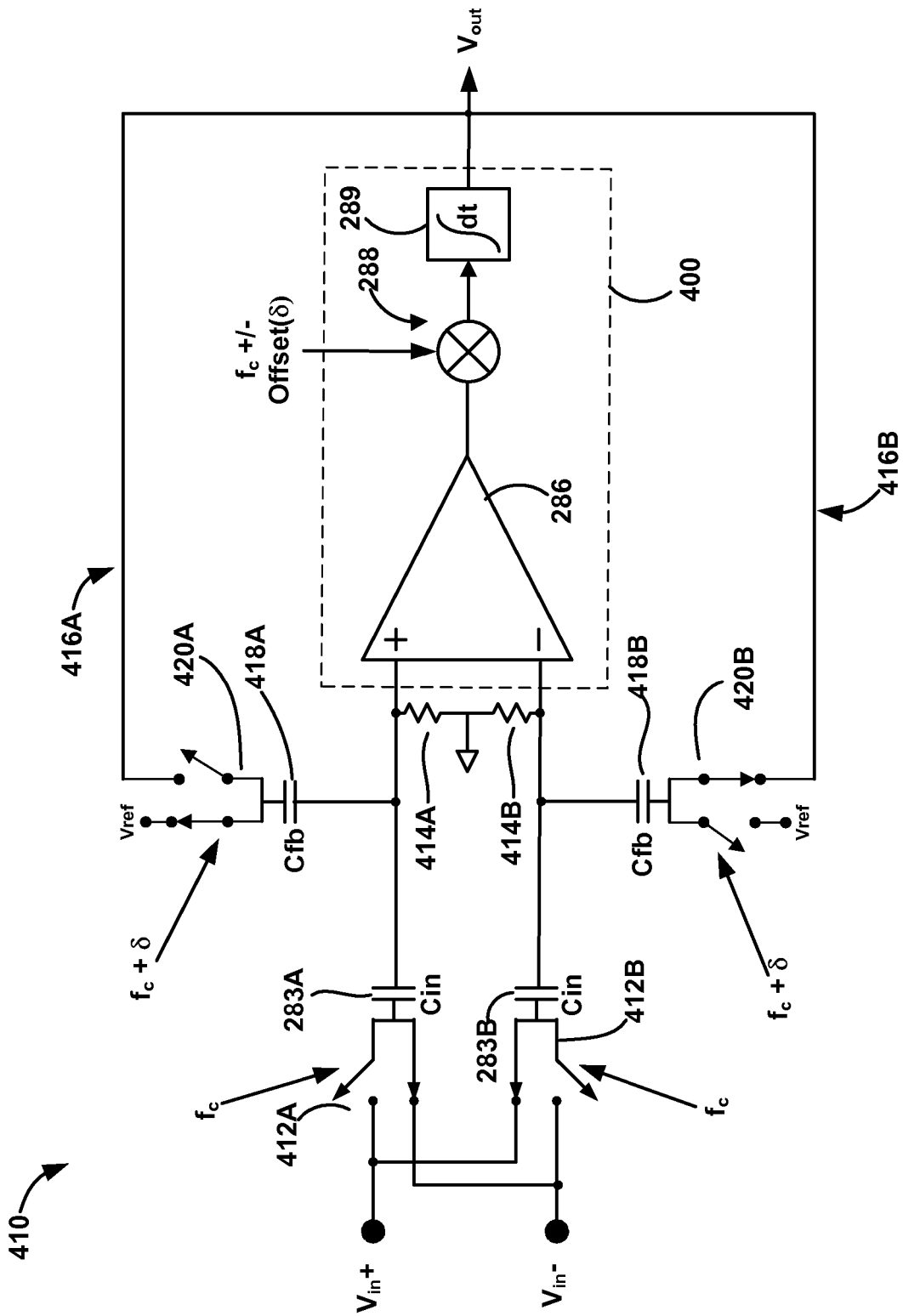
FIG. 20 is a circuit diagram illustrating an example chopper-stabilized, superheterodyne instrumentation amplifier with differential inputs.

FIG. 20 is a circuit diagram illustrating an instrumentation amplifier 410 with differential inputs $V_{in}+$ and $V_{in}-$. Instrumentation amplifier 410 is an example of superheterodyne instrumentation amplifier 272 previously described in this disclosure with reference to FIG. 15. FIG. 20 uses several reference numerals from FIG. 15 to refer to like components. However, the optional high pass filter feedback path comprising components 292, 293 and 294 is omitted from the example of FIG. 20. In general, instrumentation amplifier 410 may be constructed as a single-ended or differential amplifier. The example of FIG. 20 illustrates example circuitry for implementing a differential amplifier. The circuitry of FIG. 20 may be configured for use in each of the I and Q signal paths of FIG. 18.

In the example of FIG. 20, instrumentation amplifier 410 includes an interface to one or more sensing elements that produce a differential input signal providing voltage signals $V_{in}+$, $V_{in}-$. The differential input signal may be provided by a sensor comprising any of a variety of sensing elements, such as a set of one or more electrodes, an accelerometer, a pressure sensor, a force sensor, a gyroscope, a humidity sensor, a chemical sensor, or the like. For brain sensing, the differential signal $V_{in}+$, $V_{in}-$ may be, for example, an EEG or EcoG signal.

The differential input voltage signals are connected to respective capacitors 283A and 283B (collectively referred to as "capacitors 283") through switches 412A and 412B, respectively. Switches 412A and 412B may collectively form modulator 282 of FIG. 15. Switches 412A, 412B are driven by a clock signal provided by a system clock (not shown) at the carrier frequency $f_c$. Switches 412A, 412B may be cross-coupled to each other, as shown in FIG. 20, to reject common-mode signals. Capacitors 283 are coupled at one end to a corresponding one of switches 412A, 412B and to a corresponding input of amplifier 286 at the other end. In particular, capacitor 283A is coupled to the positive input of amplifier 286, and capacitor 283B is coupled to the negative input of amplifier 286, providing a differential input. Amplifier 286, modulator 288 and integrator 289 together may form a mixer amplifier, which may be constructed similar to mixer amplifier 400 of FIG. 19.

In FIG. 20, switches 412A, 412B and capacitors 283A, 283B form a front end of instrumentation amplifier 410. In particular, the front end may operate as a continuous time switched capacitor network. Switches 412A, 412B toggle between an open state and a closed state in which inputs signals $V_{in}+$, $V_{in}-$ are coupled to capacitors 283A, 283B at a clock frequency $f_c$ to modulate (chop) the input signal to the carrier (clock) frequency. As mentioned previously, the input signal may be a low frequency signal within a range of approximately 0 Hz to approximately 1000 Hz and, more particularly, approximately 0 Hz to 500 Hz, and still more particularly less than or equal to approximately 100 Hz. The carrier frequency may be within a range of approximately 4 kHz to approximately 10 kHz. Hence, the low frequency signal is chopped to the higher chop frequency band.

Switches 412A, 412B toggle in-phase with one another to provide a differential input signal to amplifier 286. During one phase of the clock signal $f_c$, switch 412A connects Vin+ to capacitor 283A and switch 412B connects Vin− to capacitor 283B. During another phase, switches 412A, 412B change state such that switch 412A decouples Vin+ from capacitor 283A and switch 412B decouples Vin− from capacitor 283B. Switches 412A, 412B synchronously alternate between the first and second phases to modulate the differential voltage at the carrier frequency. The resulting chopped differential signal is applied across capacitors 283A, 283B, which couple the differential signal across the positive and negative inputs of amplifier 286.

Resistors 414A and 414B (collectively referred to as "resistors 414") may be included to provide a DC conduction path that controls the voltage bias at the input of amplifier 286. In other words, resistors 414 may be selected to provide an equivalent resistance that is used to keep the bias impedance high. Resistors 414 may, for example, be selected to provide a 5 GΩ equivalent resistor, but the absolute size of the equivalent resistor is not critical to the performance of instrumentation amplifier 410. In general, increasing the impedance improves the noise performance and rejection of harmonics, but extends the recovery time from an overload. To provide a frame of reference, a 5 GΩ equivalent resistor results in a referred-to-input (RTI) noise of approximately 20 nV/rt Hz with an input capacitance (Cin) of approximately 25 pF. In light of this, a stronger motivation for keeping the impedance high is the rejection of high frequency harmonics which can alias into the signal chain due to settling at the input nodes of amplifier 286 during each half of a clock cycle.

Resistors 414 are merely exemplary and serve to illustrate one of many different biasing schemes for controlling the signal input to amplifier 286. In fact, the biasing scheme is flexible because the absolute value of the resulting equivalent resistance is not critical. In general, the time constant of resistor 414 and input capacitor 283 may be selected to be approximately 100 times longer than the reciprocal of the chopping frequency.

Amplifier 286 may produce noise and offset in the differential signal applied to its inputs. For this reason, the differential input signal is chopped via switches 412A, 412B and capacitors 283A, 283B to place the signal of interest in a different frequency band from the noise and offset. Then, instrumentation amplifier 410 chops the amplified signal at modulator 88 a second time to demodulate the signal of interest down to baseband while modulating the noise and offset up to the chop frequency band. In this manner, instrumentation amplifier 410 maintains substantial separation between the noise and offset and the signal of interest.

Modulator 288 may support direct downconversion of the selected frequency band using a superheterodyne process. In particular, modulator 288 may demodulate the output of amplifier 86 at a frequency equal to the carrier frequency $f_c$ used by switches 412A, 412B plus or minus an offset δ that is substantially equal to the center frequency of the selected frequency band. In other words, modulator 88 demodulates the amplified signal at a frequency of $f_c \pm \delta$. Integrator 289 may be provided to integrate the output of modulator 288 to produce output signal Vout. Amplifier 286 and differential feedback path branches 416A, 416B process the noisy modulated input signal to achieve a stable measurement of the low frequency input signal output while operating at low power.

Operating at low power tends to limit the bandwidth of amplifier 286 and creates distortion (ripple) in the output signal. Amplifier 286, modulator 288, integrator 289 and feedback paths 416A, 416B may substantially eliminate dynamic limitations of chopper stabilization through a combination of chopping at low-impedance nodes and AC feedback, respectively.

In FIG. 20, amplifier 286, modulator 288 and integrator 289 are represented with appropriate circuit symbols in the interest of simplicity. However, it should be understood that such components may be implemented in accordance with the circuit diagram of mixer amplifier circuit 400 provided in FIG. 19. Instrumentation amplifier 410 may provide synchronous demodulation with respect to the input signal and substantially eliminate 1/f noise, popcorn noise, and offset from the signal to output a signal that is an amplified representation of the differential voltage Vin+, Vin−.

Without the negative feedback provided by feedback path 416A, 416B, the output of amplifier 286, modulator 288 and integrator 289 could include spikes superimposed on the desired signal because of the limited bandwidth of the amplifier at low power. However, the negative feedback provided by feedback path 416A, 416B suppresses these spikes so that the output of instrumentation amplifier 410 in steady state is an amplified representation of the differential voltage produced across the inputs of amplifier 286 with very little noise.

Feedback paths 416A, 216B, as shown in FIG. 20, include two feedback path branches that provide a differential-to-single ended interface. Amplifier 286, modulator 288 and integrator 289 may be referred to collectively as a mixer amplifier. The top feedback path branch 416A modulates the output of this mixer amplifier to provide negative feedback to the positive input terminal of amplifier 286. The top feedback path branch 416A includes capacitor 418A and switch 420A. Similarly, the bottom feedback path branch 416B includes capacitor 418B and switch 420B that modulate the output of the mixer amplifier to provide negative feedback to the negative input terminal of the mixer amplifier. Capacitors 418A, 418B are connected at one end to switches 420A, 420B, respectively, and at the other end to the positive and negative input terminals of the mixer amplifier, respectively. Capacitors 418A, 418B may correspond to capacitor 291 in FIG. 15. Likewise, switches 420A, 420B may correspond to modulator 290 of FIG. 15.

Switches 420A and 420B toggle between a reference voltage (Vref) and the output of the mixer amplifier 400 to place a charge on capacitors 418A and 418B, respectively. The reference voltage may be, for example, a mid-rail voltage between a maximum rail voltage of amplifier 286 and ground. For example, if the amplifier circuit is powered with a source of 0 to 2 volts, then the mid-rail Vref voltage may be on the order of 1 volt. Switches 420A and 420B should be 180 degrees out of phase with each other to ensure that a negative feedback path exists during each half of the clock cycle. One of switches 420A, 420B should also be synchronized with the mixer amplifier 400 so that the negative feedback suppresses the amplitude of the input signal to the mixer amplifier to keep the signal change small in steady state. Hence, a first one of the switches 420A, 420B may modulate at a frequency of $f_c \pm \delta$, while a second switch 420A, 420B modulates at a frequency of $f_c \pm \delta$, but 180 degrees out of phase with the first switch. By keeping the signal change small and switching at low impedance nodes of the mixer amplifier, e.g., as shown in the circuit diagram of FIG. 19, the only significant voltage transitions occur at switching nodes. Consequently, glitching (ripples) is substantially eliminated or reduced at the output of the mixer amplifier.

Switches 412 and 420, as well as the switches at low impedance nodes of the mixer amplifier, may be CMOS SPDT switches. CMOS switches provide fast switching dynamics that enables switching to be viewed as a continuous process. The transfer function of instrumentation amplifier 210 may be defined by the transfer function provided in equation (1) below, where Vout is the voltage of the output of mixer amplifier 400, Cin is the capacitance of input capacitors 283, ΔVin is the differential voltage at the inputs to amplifier 286, Cfb is the capacitance of feedback capacitors 418A, 418B, and Vref is the reference voltage that switches 420A, 420B mix with the output of mixer amplifier 400.

$$Vout = Cin(\Delta Vin)/Cfb + Vref \quad (1)$$

From equation (1), it is clear that the gain of instrumentation amplifier 410 is set by the ratio of input capacitors Cin and feedback capacitors Cfb, i.e., capacitors 283 and capacitors 418. The ratio of Cin/Cfb may be selected to be on the order of 100. Capacitors 418 may be poly-poly, on-chip capacitors or other types of MOS capacitors and should be well matched, i.e., symmetrical.

Although not shown in FIG. 20, instrumentation amplifier 410 may include shunt feedback paths for auto-zeroing amplifier 410. The shunt feedback paths may be used to quickly reset amplifier 410. An emergency recharge switch also may be provided to shunt the biasing node to help reset the amplifier quickly. The function of input capacitors 283 is to up-modulate the low-frequency differential voltage and reject common-mode signals. As discussed above, to achieve up-modulation, the differential inputs are connected to sensing capacitors 283A, 283B through SPDT switches 412A, 412B, respectively. The phasing of the switches provides for a differential input to amplifier 286. These switches 412A, 412B operate at the clock frequency, e.g., 4 kHz. Because capacitors 283A, 283B toggle between the two inputs, the differential voltage is up-modulated to the carrier frequency while the low-frequency common-mode signals are suppressed by a zero in the charge transfer function. The rejection of higher-bandwidth common signals relies on this differential architecture and good matching of the capacitors.

Blanking circuitry may be provided in some examples for applications in which measurements are taken in conjunction with stimulation pulses delivered by a cardiac pacemaker, cardiac defibrillator, or neurostimulator. Such blanking circuitry may be added between the inputs of amplifier 286 and coupling capacitors 283A, 283B to ensure that the input signal settles before reconnecting amplifier 86 to the input signal. For example, the blanking circuitry may be a blanking multiplexer (MUX) that selectively couples and de-couples amplifier 286 from the input signal. This blanking circuitry may selectively decouple the amplifier 286 from the differential input signal and selectively disable the first and second modulators, i.e., switches 412, 420, e.g., during delivery of a stimulation pulse.

A blanking MUX is optional but may be desirable. The clocks driving switches 412, 420 to function as modulators cannot be simply shut off because the residual offset voltage on the mixer amplifier would saturate the amplifier in a few milliseconds. For this reason, a blanking MUX may be provided to decouple amplifier 86 from the input signal for a specified period of time during and following application of a stimulation by a cardiac pacemaker or defibrillator, or by a neurostimulator.

To achieve suitable blanking, the input and feedback switches 412, 420 should be disabled while the mixer amplifier continues to demodulate the input signal. This holds the state of integrator 289 within the mixer amplifier because the modulated signal is not present at the inputs of the integrator, while the demodulator continues to chop the DC offsets. Accordingly, a blanking MUX may further include circuitry or be associated with circuitry configured to selectively disable switches 412, 420 during a blanking interval. Post blanking, the mixer amplifier may require additional time to resettle because some perturbations may remain. Thus, the total blanking time includes time for demodulating the input signal while the input switches 412, 420 are disabled and time for settling of any remaining perturbations. An example blanking time following application of a stimulation pulse may be approximately 8 ms with 5 ms for the mixer amplifier and 3 ms for the AC coupling components.

Examples of various additional chopper amplifier circuits that may be suitable for or adapted to the techniques, circuits and devices of this disclosure are described in U.S. patent application Ser. No. 11/700,404, filed Jan. 31, 2007, to Timothy J. Denison, entitled "Chopper Stabilized Instrumentation Amplifier," the entire content of which is incorporated herein by reference. Examples of frequency selective monitors that may utilize a heterodyning, chopper-stabilized amplifier architecture are described in U.S. Provisional Application No. 60/975,372 to Denison et al., entitled "FREQUENCY SELECTIVE MONITORING OF PHYSIOLOGICAL SIGNALS," and filed on Sep. 26, 2007, commonly-assigned U.S. Provisional Application No. 61/025,503 to Denison et al., entitled "FREQUENCY SELECTIVE MONITORING OF PHYSIOLOGICAL SIGNALS, and filed on Feb. 1, 2008, and commonly-assigned U.S. Provisional Application No. 61/083,381, entitled, "FREQUENCY SELECTIVE EEG SENSING CIRCUITRY," and filed on Jul. 24, 2008. The entire contents of above-identified U.S. Provisional Application Nos. 60/975,372, 61/025,503, and 61/083,381 are incorporated herein by reference. Further examples of chopper amplifier circuits are also described in further detail in commonly-assigned U.S. patent application Ser. No. 12/237,868 to Denison et al., entitled, "FREQUENCY SELECTIVE MONITORING OF PHYSIOLOGICAL SIGNALS" and filed on the same date as the present disclosure. U.S. patent application Ser. No. 12/237,868 to Denison et al. is incorporated herein by reference in its entirety.

Various examples of the described systems and devices may include processors that are realized by any one or more of microprocessors, ASICs, FPGA, or other equivalent integrated logic circuitry. The processors may also utilize several different types of storage methods to hold computer-readable instructions for the device operation and data storage. These memory and storage media types may include a type of hard disk, RAM, ROM, EEPROM, or flash memory, e.g. CompactFlash, SmartMedia, or Secure Digital (SD). Each storage option may be chosen depending on the example. While IMD 16 and IMD 124 may contain permanent memory, external programmer 14 may contain a more portable removable memory type to enable easy data transfer or offline data analysis.

Many examples of systems, devices, and techniques (or "methods") have been described. These and other examples are within the scope of the following claims. For example, functions attributed to processor 50 of IMD 16 may be performed by processor 92 of programmer 14 or a processor of another computing device or another medical device. In addition, while DBS is primarily described above, in other examples, other stimulation therapies may be implemented in addition to or instead of DBS to manage at least one of the movement, sleep or speech disorders of patient 12. Example therapies include, but are not limited to, pain therapy, spinal cord stimulation (SCS), peripheral nerve stimulation (PNS), peripheral nerve field stimulation (PNFS), functional electrical stimulation (FES) of a muscle or muscle group, incontinence therapy, gastric stimulation, and pelvic floor stimulation. These and other therapies may be directed toward treating conditions such as chronic pain, incontinence, sexual dysfunction, obesity, migraine headaches, Parkinson's disease, depression, epilepsy, seizures, or any other neurological disease.

In addition, while the above devices (e.g., memory 52) store therapy programs for each of the movement, sleep, and speech states, in other examples, the devices in accordance with the examples of the disclosure may store therapy programs for two of the movement, sleep, and speech states. That is, systems described herein may store therapy programs associated with the movement and speech states or, alternatively, the sleep and speech states, or the movement and sleep states.

The invention claimed is:

1. A method comprising:
   with a processor, determining a patient state of a patient based on received information, wherein the patient state comprises at least one of a movement state, a sleep state or a speech state;
   with the processor, selecting a therapy program or instruction for modifying a baseline therapy program from a plurality of stored therapy programs or instructions for modifying the baseline therapy program based on the determined patient state, wherein the plurality of stored therapy programs or instructions comprises:

a first therapy program or instruction associated with the speech state, and a second therapy program or instruction associated with at least one of the movement state or the sleep state, wherein selecting the therapy program or instruction based on the determined patient state comprises selecting the first therapy program or instruction in response to determining the patient is in the speech state and selecting the second therapy program or instruction in response to determining the patient is in at least one of the movement state or the sleep state; and controlling a medical device to deliver deep brain stimulation therapy to the patient based on the selected therapy program or instruction.

2. The method of claim 1, wherein determining the patient state comprises receiving an indication of the patient state from the patient, the received information comprising the indication.

3. The method of claim 2, wherein receiving an indication from the patient comprises receiving input from the patient indicating the patient state via at least one of an accelerometer, a patient programmer or a voice detector.

4. The method of claim 2, wherein receiving an indication from the patient comprises detecting at least one biosignal from a brain of the patient that results from a volitional patient input.

5. The method of claim 4, wherein detecting at least one biosignal from the brain of the patient comprises:

detecting a bioelectrical signal from the brain of the patient via one or more electrodes; and processing the bioelectrical signal to determine whether the bioelectrical signal includes the biosignal.

6. The method of claim 5, wherein processing the bioelectrical signal comprises evaluating one or more frequency characteristics of the bioelectrical signal.

7. The method of claim 6, wherein the one or more frequency characteristics comprise a strength of the electrical signal within one or more frequency bands.

8. The method of claim 7, wherein the one or more frequency characteristics comprise relative strengths between two or more frequency bands.

9. The method of claim 1, wherein determining the patient state comprises:

receiving, from a sensing module, a bioelectrical signal from a brain of the patient, the received information comprising the bioelectrical signal; and determining whether the bioelectrical signal indicates the patient is in the movement state, speech state or sleep state.

10. The method of claim 9, wherein the bioelectrical signal comprises at least one of an electroencephalogram (EEG) signal, electromyogram (EMG) signal, electrocorticogram (ECoG) signal, a field potential or a single cell recording of the brain of the patient.

11. The method of claim 1, wherein selecting the therapy program or instruction comprises determining an activity level or posture of the patient and selecting the therapy program or instruction based on the determined activity level or posture.

12. A system comprising:

a memory that stores a plurality of therapy programs for deep brain stimulation therapy or instructions for modifying a baseline therapy program for deep brain stimulation therapy, and associates each therapy program or instruction with a patient state, the patient state comprising at least one of a movement state, a sleep state or a speech state, wherein the plurality of therapy programs or instructions comprises:

a first therapy program or instruction associated with the speech state, and a second therapy program or instruction associated with at least one of the movement state or the sleep state; and a processor that determines the patient state of a patient and selects a therapy program or instruction from the plurality of therapy programs or instructions stored by the memory based on the determined patient state, wherein the processor selects the first therapy program in response to determining the patient is in the speech state and selects the second therapy program in response to determining the patient is in at least one of the movement state or the sleep state.

13. The system of claim 12, wherein the processor receives input from a patient indicating the determined patient state.

14. The system of claim 13, further comprising a medical device programmer comprising a user interface, wherein the medical device programmer is configured to receive input from a patient indicating the determined patient state and transmit an indication of the determined patient state to the processor.

15. The system of claim 12, further comprising a biosignal detection module that monitors a bioelectrical signal from a brain of a patient, wherein at least one of the biosignal detection module or the processor determines whether the bioelectrical signal indicates the patient is in the movement state, speech state or sleep state based on the bioelectrical signal from the brain.

16. The system of claim 15, wherein the bioelectrical signal comprises at least one of an electroencephalogram (EEG) signal, electromyogram (EMG) signal, electrocorticogram (ECoG) signal, a field potential or a single cell recording of the brain of the patient.

17. The system of claim 15, wherein the bioelectrical signal is generated by volitional input by the patient.

18. The system of claim 15, wherein the at least one of the biosignal detection module or the processor evaluates one or more frequency characteristics of the bioelectrical signal to determine whether the bioelectrical signal indicates the patient is in the movement state, speech state or sleep state.

19. The system of claim 12, wherein the movement state comprises at least one of intending to initiate movement, initiating movement, attempting to initiate movement or moving, the speech state comprises at least one of intending to initiate speech, initiating speech, attempting to initiate speech or speaking, and the sleep state comprises at least one of intending to initiate sleep, initiating sleep, attempting to initiate sleep or sleeping.

20. The system of claim 12, further comprises a motion sensor, wherein the processor receives input from the motion sensor, determines an activity level or posture of a patient, and selects the therapy program or instruction based on the determined activity level or posture.

21. The system of claim 12, further comprising a therapy module, wherein the processor controls the therapy module to deliver deep brain stimulation therapy to a patient based on the selected therapy program or instruction.

22. A non-transitory computer-readable medium comprising instructions that, when executed by a processor, cause the processor to:

determine a patient state of a patient based on received information, wherein the patient state comprises at least one of a movement state, sleep state or speech state;

select a therapy program or instruction for modifying a baseline therapy program from a plurality of therapy programs or instructions for modifying the baseline therapy program stored by a memory based on the determined patient state, wherein the plurality of stored therapy programs or instructions comprises:
  a first therapy program or instruction associated with the speech state, and
  a second therapy program or instruction associated with at least one of the movement state or the sleep state,
  wherein the instructions, when executed by the processor, cause the processor to select the therapy program or instruction based on the determined patient state by at least selecting the first therapy program or instruction in response to determining the patient is in the speech state and selecting the second therapy program or instruction in response to determining the patient is in at least one of the movement state or the sleep state; and
control a medical device to deliver deep brain stimulation therapy to the patient based on the selected therapy program or instruction.

23. A system comprising:
means for determining a patient state of a patient, wherein the patient state comprises at least one of a movement state, sleep state or speech state; and
means for selecting a therapy program for deep brain stimulation or instruction for modifying a baseline therapy program for deep brain stimulation from a plurality of stored therapy programs or instructions for modifying the baseline therapy program based on the determined patient state, wherein the plurality of stored programs or instructions comprises:
  a first therapy program or instruction associated with the speech state, and
  a second therapy program or instruction associated with at least one of the movement state or the sleep state, and
  wherein the means for selecting selects the therapy program or instruction by at least selecting the first therapy program or instruction in response to determining the patient is in the speech state and selecting the second therapy program or instruction in response to determining the patient is in at least one of the movement state or the sleep state.

24. The system of claim 23, wherein the means for determining the patient state comprises means for receiving input from the patient indicating the patient state.

25. The system of claim 23, wherein the means for determining the patient state comprises means for determining the patient state based on biosignals detected within a brain of the patient.

26. The system of claim 23, further comprising means for delivering deep brain stimulation therapy to the patient according to the selected therapy program or instruction.

27. A method comprising:
with a processor, determining whether a patient is in a movement state;
with the processor, determining whether the patient is in a speech state;
with the processor, selecting, from a plurality of stored therapy programs or instructions for modifying a baseline therapy program, a first therapy program or a first instruction for modifying the baseline therapy program if the patient is in the movement state and selecting, from the plurality of stored therapy programs or instructions for modifying a baseline therapy program, a second therapy program different than the first therapy program or a second instruction different than the first instruction for modifying the baseline therapy program if the patient is in the speech state; and
controlling a medical device to deliver deep brain stimulation therapy to the patient based on the selected therapy program or instruction for modifying the baseline therapy program.

28. The method of claim 27, wherein determining whether the patient is in the movement state and determining whether the patient is in the speech state comprises receiving input from the patient indicating whether the patient is in the movement state or the speech state.

29. The method of claim 27, wherein determining whether the patient is in the movement state and determining whether the patient is in the speech state comprises sensing a bioelectrical signal within a brain of the patient and determining whether the bioelectrical signal indicates the patient is in the movement state or the speech state.

* * * * *